(12) United States Patent  (10) Patent No.: US 7,753,949 B2
Lamphere et al.  (45) Date of Patent: Jul. 13, 2010

(54) VALVE PROSTHESIS SYSTEMS AND METHODS

(75) Inventors: David G. Lamphere, Framingham, MA (US); Tuan Anh Nguyen, Woburn, MA (US); Howard C. Herrmann, Bryn Mawr, PA (US)

(73) Assignees: The Trustees of the University of Pennsylvania, Philadelphia, PA (US); EndoValve, Inc., Princeton, NJ (US)

( * ) Notice: Subject to any disclaimer, the term of this patent is extended or adjusted under 35 U.S.C. 154(b) by 140 days.

(21) Appl. No.: 11/869,972

(22) Filed: Oct. 10, 2007

(65) Prior Publication Data

US 2008/0208332 A1  Aug. 28, 2008

Related U.S. Application Data

(60) Provisional application No. 60/902,988, filed on Feb. 23, 2007.

(51) Int. Cl.
*A61F 2/06*  (2006.01)
*A61F 2/24*  (2006.01)

(52) U.S. Cl. ..................... 623/1.26; 623/2.14
(58) Field of Classification Search ................ 623/2.11, 623/1.24, 1.26, 2.1, 1.15, 2.36–2.42, 2.12–2.35
See application file for complete search history.

(56) References Cited

U.S. PATENT DOCUMENTS

| 3,143,742 | A | * | 8/1964 | Cromie | ....................... 623/2.38 |
| 3,686,740 | A | * | 8/1972 | Shiley | ........................... 29/439 |
| 4,705,516 | A | * | 11/1987 | Barone et al. | .............. 623/2.39 |
| 4,759,759 | A | | 7/1988 | Walker et al. | |

(Continued)

FOREIGN PATENT DOCUMENTS

EP  1281375  2/2003

(Continued)

OTHER PUBLICATIONS

Davies, H., "Catheter-Mounted Valve For Temporary Relief of Aortic Insufficiency," The Lancet, Jan. 30, 1965.

(Continued)

*Primary Examiner*—Alin J Stewart
(74) *Attorney, Agent, or Firm*—McCarter & English, LLP

(57) ABSTRACT

Valve prostheses are disclosed that are adapted for secure and aligned placement relative to a heart annulus. The valve prostheses may be placed in a non-invasive manner, e.g., via trans-catheter techniques, and may be positioned/repositioned until proper alignment and positioning is achieved. The valve prosthesis may include a resilient ring, a plurality of leaflet membranes mounted with respect to the resilient ring, and a plurality of positioning elements movably mounted with respect to the flexible ring, each of the positioning elements defining a first tissue engaging region and a second tissue engaging region spaced from the first tissue engaging region. The positioning elements are adapted to substantially completely invert by rotating relative to the resilient ring between a first position in which each of the first and second tissue engaging regions is inwardly directed for facilitating positioning of the valve prosthesis within a delivery catheter, and a second position in which each of the first and second tissue engaging regions is outwardly directed for engaging tissue. The valve prosthesis may also include a valve skirt mounted with respect to the resilient ring.

40 Claims, 31 Drawing Sheets

U.S. PATENT DOCUMENTS

| | | | |
|---|---|---|---|
| 5,197,979 A * | 3/1993 | Quintero et al. | 623/1.26 |
| 5,336,258 A * | 8/1994 | Quintero et al. | 623/2.1 |
| 5,554,185 A | 9/1996 | Block et al. | |
| 5,855,601 A | 1/1999 | Bessler et al. | |
| 5,984,959 A * | 11/1999 | Robertson et al. | 623/2.11 |
| 6,042,554 A * | 3/2000 | Rosenman et al. | 623/2.11 |
| 6,074,418 A * | 6/2000 | Buchanan et al. | 623/2.11 |
| 6,287,339 B1 * | 9/2001 | Vazquez et al. | 623/2.4 |
| 6,425,916 B1 | 7/2002 | Garrison et al. | |
| 6,458,153 B1 | 10/2002 | Bailey et al. | |
| 6,551,344 B2 | 4/2003 | Thill | |
| 6,605,102 B1 | 8/2003 | Mazzocchi et al. | |
| 6,676,698 B2 * | 1/2004 | McGuckin et al. | 623/1.24 |
| 6,682,559 B2 | 1/2004 | Myers et al. | |
| 6,786,925 B1 * | 9/2004 | Schoon et al. | 623/2.38 |
| 6,790,229 B1 * | 9/2004 | Berreklouw | 623/2.1 |
| 6,846,325 B2 | 1/2005 | Liddicoat | |
| 6,893,459 B1 * | 5/2005 | Macoviak | 623/2.11 |
| 6,896,690 B1 | 5/2005 | Lambrecht | |
| 6,951,571 B1 * | 10/2005 | Srivastava | 623/1.24 |
| 6,974,476 B2 * | 12/2005 | McGuckin et al. | 623/2.36 |
| 7,041,132 B2 * | 5/2006 | Quijano et al. | 623/2.11 |
| 7,097,659 B2 * | 8/2006 | Woolfson et al. | 623/2.4 |
| 7,311,730 B2 * | 12/2007 | Gabbay | 623/2.38 |
| 7,316,712 B2 | 1/2008 | Peredo | |
| 7,320,704 B2 | 1/2008 | Lashinski et al. | |
| 7,329,279 B2 * | 2/2008 | Haug et al. | 623/2.11 |
| 7,374,571 B2 * | 5/2008 | Pease et al. | 623/2.12 |
| 7,429,269 B2 * | 9/2008 | Schwammenthal et al. | 623/2.14 |
| 7,442,204 B2 * | 10/2008 | Schwammenthal et al. | 623/1.24 |
| 7,481,838 B2 * | 1/2009 | Carpentier et al. | 623/2.18 |
| 7,524,330 B2 * | 4/2009 | Berreklouw | 623/1.36 |
| 7,569,071 B2 * | 8/2009 | Haverkost et al. | 623/1.24 |
| 7,611,535 B2 * | 11/2009 | Woolfson et al. | 623/2.38 |
| 2001/0002445 A1 | 5/2001 | Vesely | |
| 2001/0044656 A1 * | 11/2001 | Williamson et al. | 623/2.11 |
| 2002/0055774 A1 | 5/2002 | Liddicoat | |
| 2002/0133226 A1 | 9/2002 | Marquez et al. | |
| 2002/0138138 A1 | 9/2002 | Yang et al. | |
| 2002/0173843 A1 | 11/2002 | Peredo | |
| 2003/0036791 A1 | 2/2003 | Phillip et al. | |
| 2003/0125805 A1 | 7/2003 | Johnson et al. | |
| 2004/0024451 A1 | 2/2004 | Johnson et al. | |
| 2004/0034411 A1 * | 2/2004 | Quijano et al. | 623/2.11 |
| 2004/0044406 A1 | 3/2004 | Woolfson et al. | |
| 2004/0092858 A1 | 5/2004 | Wilson | |
| 2004/0097979 A1 | 5/2004 | Svanidze | |
| 2004/0122516 A1 | 6/2004 | Fogarty et al. | |
| 2004/0127981 A1 | 7/2004 | Rahdert | |
| 2004/0127982 A1 | 7/2004 | Machold | |
| 2004/0138745 A1 | 7/2004 | Macoviak | |
| 2004/0186563 A1 | 9/2004 | Iobbi | |
| 2004/0210304 A1 | 10/2004 | Seguin | |
| 2004/0225353 A1 | 11/2004 | McGuckin, Jr. | |
| 2004/0260393 A1 | 12/2004 | Rahdert | |
| 2005/0010287 A1 | 1/2005 | Macoviak et al. | |
| 2005/0033398 A1 | 2/2005 | Seguin | |
| 2005/0043760 A1 | 2/2005 | Fogarty et al. | |
| 2005/0055089 A1 | 3/2005 | Macoviak | |
| 2005/0075584 A1 | 4/2005 | Cali | |
| 2005/0137697 A1 | 6/2005 | Salahieh et al. | |
| 2005/0182486 A1 * | 8/2005 | Gabbay | 623/2.11 |
| 2005/0216079 A1 | 9/2005 | Macoviak | |
| 2005/0261759 A1 | 11/2005 | Lambrecht | |
| 2005/0267573 A9 | 12/2005 | Macoviak et al. | |
| 2006/0020327 A1 | 1/2006 | Lashinski et al. | |
| 2006/0020332 A1 | 1/2006 | Lashinski et al. | |
| 2006/0020333 A1 | 1/2006 | Lashinski et al. | |
| 2006/0020334 A1 | 1/2006 | Lashinski et al. | |
| 2006/0025854 A1 | 2/2006 | Lashinski et al. | |
| 2006/0025855 A1 | 2/2006 | Lashinski et al. | |
| 2006/0089671 A1 | 4/2006 | Goldfarb et al. | |
| 2006/0161249 A1 * | 7/2006 | Realyvasquez et al. | 623/2.11 |
| 2006/0253191 A1 | 11/2006 | Salahieh et al. | |
| 2006/0271081 A1 | 11/2006 | Realyvasquez | |
| 2007/0010877 A1 | 1/2007 | Salahieh et al. | |
| 2007/0016286 A1 * | 1/2007 | Herrmann et al. | 623/2.11 |
| 2007/0260305 A1 * | 11/2007 | Drews et al. | 623/2.11 |
| 2007/0265701 A1 * | 11/2007 | Gurskis et al. | 623/2.11 |
| 2007/0288089 A1 * | 12/2007 | Gurskis et al. | 623/2.4 |
| 2008/0015687 A1 | 1/2008 | Lashinski et al. | |
| 2008/0033543 A1 * | 2/2008 | Gurskis et al. | 623/2.11 |
| 2008/0208328 A1 * | 8/2008 | Antocci et al. | 623/2.11 |
| 2008/0208332 A1 * | 8/2008 | Lamphere et al. | 623/2.38 |
| 2008/0221672 A1 * | 9/2008 | Lamphere et al. | 623/2.12 |
| 2008/0281411 A1 * | 11/2008 | Berreklouw | 623/2.11 |

FOREIGN PATENT DOCUMENTS

| | | |
|---|---|---|
| WO | WO 98/10719 | 3/1998 |
| WO | WO 00/44311 | 8/2000 |
| WO | WO 03/088873 | 10/2003 |
| WO | WO 2004/043293 | 1/2004 |
| WO | WO 2004/019811 | 3/2004 |
| WO | WO 2004/028558 | 4/2004 |
| WO | WO 2004/030568 | 4/2004 |
| WO | WO 2004/030569 | 4/2004 |
| WO | WO 2004/030570 | 4/2004 |
| WO | WO 2005/112827 | 1/2005 |
| WO | WO 2005/009285 | 2/2005 |
| WO | WO 2005/046528 | 5/2005 |

OTHER PUBLICATIONS

Bonhoeffer, et al., "Precutaneous Insertion of the Pulmonary Valve," J. of the Am. College of Cardionogy, 2002, 39(10), 1664-1669.

Cribier, et al., "Precutaneous ranscatheter implantation of an Aortic Valve Prostheses for Calcific Aortic Stenosis," Circulation, 2002, 3006-3008.

Block, P.C., "Precutaneous Mitral Valve Repair for Mitral Regurgitation," J. of Interventional Cardiology, 2003, 16(1) 93-96.

PCT International Search Report dated Feb. 9, 2005.

PCT International Search Report dated Aug. 8, 2008 (PCT/US08/50096).

PCT International Search Report dated Aug. 8, 2008 (PCT/US08/54410).

PCT International Search Report dated Aug. 12, 2008.

European Search Report dated Mar. 28, 2007.

* cited by examiner

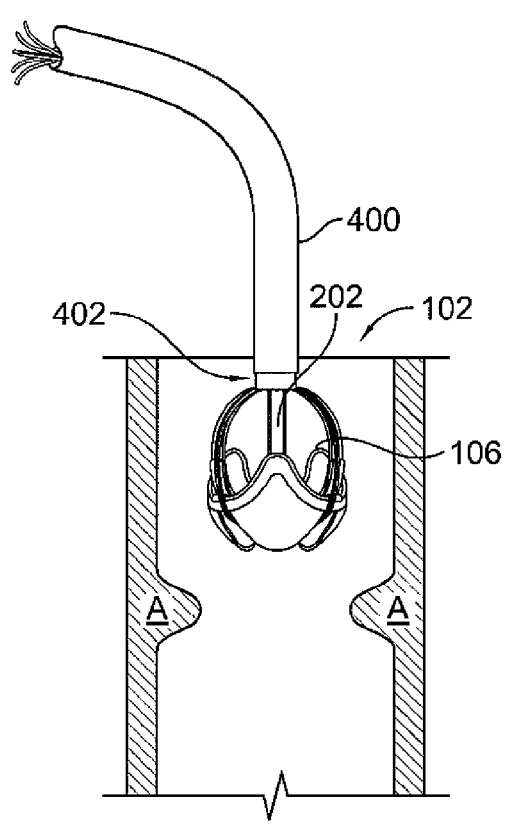 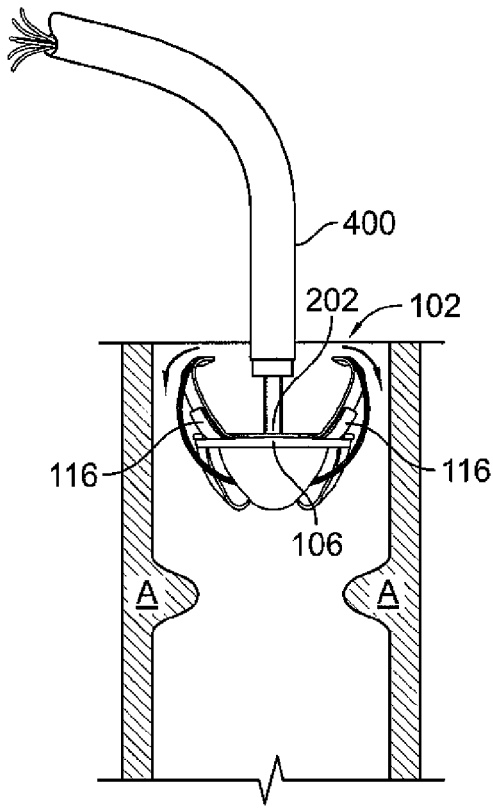
FIG. 4A          FIG. 4B
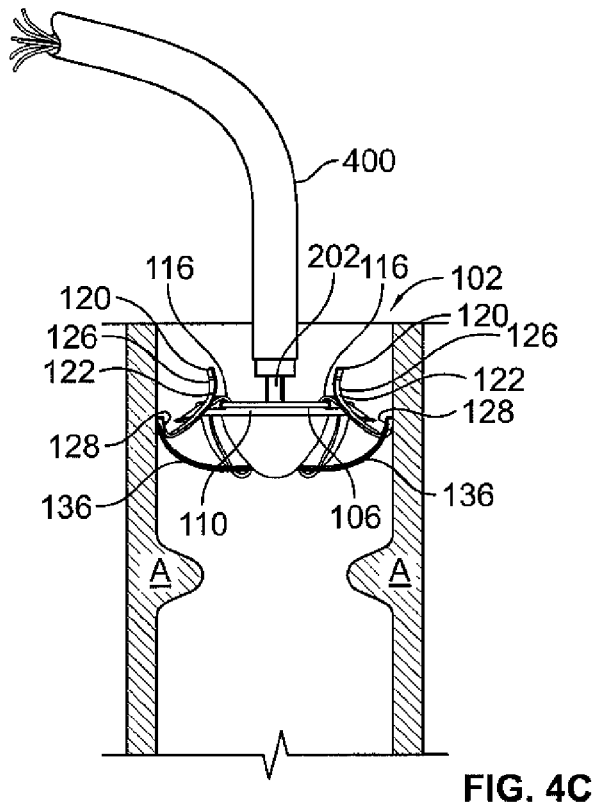
FIG. 4C

VALVE PROSTHESIS SYSTEMS AND METHODS

CROSS-REFERENCE TO RELATED APPLICATIONS

The present application claims the benefit of provisional patent application entitled "Valve Prosthesis System" that was filed on Feb. 23, 2007 and assigned Ser. No. 60/902,988. The entire contents of the foregoing provisional application are incorporated herein by reference.

BACKGROUND

1. Technical Field

The present disclosure is directed to advantageous valve prosthesis systems and associated methods/systems for placement of a heart valve prosthesis and, more particularly, to a mitral valve prosthesis that is adapted for secure and aligned placement relative to a heart annulus and associated methods/systems for placement thereof.

2. Background Art

Heart valve regurgitation occurs when the heart valve does not close completely as a result of disease or injury. Mitral regurgitation due to ischemic and degenerative (prolapse) disease has been shown to contribute to left ventricular dilation and dysfunction due to remodeling, and is associated with increased rates of cardiac events and death. Currently, malfunctioning heart valves may be replaced with biologic or mechanical prostheses through open-heart surgery with the attendant significant risk of death, stroke, infection, bleeding, and complications due to the use of general anesthesia and cardiopulmonary bypass.

Based on the success of percutaneous balloon valvuplasty for mitral stenosis, investigators have explored other alternative methods to treat valvular heart disease without surgery. For example, Cribier et al. describe a balloon-expandable stent to which a biologic valve prosthesis is sewn. (See, "Percutaneous Transcatheter Implantation of an Aortic Valve Prosthesis for Calcific Aortic Stenosis," Circulation, Dec. 10, 2002, pages 3006-3008.) The Cribier device is utilized to treat calcific aortic stenosis. Bonhoeffer et al. describe a similar stent approach with a bovine venous jugular) valve inserted to treat pulmonic valve disease. (See, "Percutaneous Insertion of the Pulmonary Valve," Journal of the American College of Cardiology, Vol. 39, No. 10, May 15, 2002, pages 1664-1669.) Others are developing repair techniques for mitral valve disease that involve placing a clip on the mitral leaflets (U.S. Pat. No. 6,629,534), cinching the mitral annulus from the coronary sinus (U.S. Pat. No. 6,537,314), or deploying an inflatable heart valve that is mechanically held in place (U.S. Pat. No. 5,554,185).

Norred (U.S. Pat. No. 6,482,228) discloses a percutaneous aortic valve replacement in which a heart valve prosthesis having ribs and a circular elastomeric canopy is folded for insertion into a catheter for delivery to the implantation region without surgery. Once in the ascending aorta, the body and leaflets of the heart valve prosthesis are opened like an umbrella by pulling on a central column of suture-like members. Hinge joints are used to create a miniature umbrella. However, the aortic valve prosthesis is anchored using a stent system that is extended in the ascending aorta to anchor the valve in the aortic channel above the biologic aortic valve. The suture-like members used to open the umbrella structure are deployed as part of the stent system. Such a design is not amenable to placement of the heart valve prosthesis at the location of the biologic valve.

Other stented heart valve prostheses are described in the art in which the anchoring system is a passive one that requires either balloon expandable stents or a self-expanding stent design. For example, such stented designs are described in U.S. Pat. No. 6,454,799, US 2002/0138138, U.S. Pat. No. 6,582,462, U.S. Pat. No. 6,458,153, U.S. Pat. No. 6,425,916, and U.S. Pat. No. 5,855,601. It will be appreciated that once these stented heart valve prostheses are deployed, they cannot be repositioned, refolded, or easily removed. Furthermore, the rigidity of the stent as it is deployed in calcified positions may allow for regurgitation around the outside of the stent, as has been seen in the early aortic valve deployments which utilize this design. It is also difficult to position these designs as one has to inflate a balloon in a moving column of blood while the heart is beating and one only gets one chance to accurately deploy it.

An additional difficulty occurs when deploying a stented heart valve in an annulus that is not thickened by calcium. The stent design lends itself slightly better to the aortic position where the height of the annulus has been increased and the width thickened by the presence of calcium in calcific aortic stenosis. However, when calcium is not present, as in other causes of aortic valve disease and in the mitral position, the stent may be difficult to anchor on the relatively thin annulus. Furthermore, the nature by which the stent folds on a balloon and then expands with plastic deformability limits the ratio of its initial to final size such that it will, by necessity, have a fairly large profile making percutaneous insertion via catheter more difficult in a valve annulus with a large diameter that has not been reduced by calcium deposition.

Herrmann et al. (US 2007/0016286) disclose a percutaneously inserted bistable heart valve prosthesis that may be folded inside a catheter for delivery to the patient's heart for implantation. The heart valve has an elastic annular ring, a body member having a plurality of legs, each leg connecting at one end to the annular ring, claws that are adjustable from a first position to a second position by application of external force so as to allow ingress of surrounding heart tissue into the claws in the second position, and leaflet membranes connected to the annular ring, the body member and/or the legs. The disclosed leaflet membranes having a first position for blocking blood flow therethrough and a second position for allowing blood flow therethrough. The heart valve is designed such that upon removal of the external force, the claws elastically revert to the first position so as to grip the heart tissue positioned within the claws, thereby holding the heart valve in place. The body member and claws may be integrated into a one-piece design. The heart valve so designed may be used as a prosthesis for the mitral valve, aortic valve, pulmonary valve, or tricuspid valve by adapting the annular ring to fit in a respective mitral, aortic, pulmonary, or tricuspid valve opening of the heart.

Machold et al. (US 2004/0127982) disclose an implant that is sized and configured to attach to the annulus of a dysfunctional heart valve. In use, the implant extends across the major axis of the annulus above and/or along the valve annulus. The implant reshapes the major axis dimension and/or other surrounding anatomic structures and is intended to restore a more functional anatomic shape and tension. Machold et al. contemplate a pair of struts that are joined by a rail and that carry other structures to enhance the anchorage and stabilization of the implant in the heart valve annulus. The anchoring mechanisms may be located below the plane of the annulus to engage infra-annular heart tissue adjoining the annulus in the ventricle and/or may be located at or above the plane of the annulus, to engage tissue on the annulus or in the atrium. Machold et al. further disclose that the struts may be used to simply locate the implant in the valve, imparting little or no force on their own. In this arrangement, the annulus reshaping forces of the Machold design emanate from the rail(s) above the commissures.

Under image guidance, the Machold et al. strut on the leading end of the implant is freed from a sheath and seated retrograde in the posterior commissure of the valve annulus. Anchoring structures or mechanisms associated with the strut are also placed into contact with adjoining tissue below and/or above the plane of the annulus. As shown in FIG. 25B, the delivery catheter maintains force on the leading strut within the posterior commissure as the sheath is withdrawn in line with the coaptation line in a posterior-to-anterior direction along the coaptation line. Similar structures for positioning an implant relative to an annulus are disclosed by Vazquez et al. (U.S. Pat. No. 6,287,339)

Despite efforts to date, a need remains for an improved heart valve prosthesis design that allows a low profile for insertion via a catheter but, in the absence of a balloon or stent, transforms to a large profile once deployed. A heart valve prosthesis design is also desired that can be deployed, folded, removed, and then redeployed so as to increase the safety as well as the preciseness of prosthesis deployment. Still further, a need remains for heart valve prosthesis design(s) that may be effectively aligned and/or oriented relative to the heart and, most desirably, is substantially self-aligning and/or self-orienting with respect thereto. Reliable and effective deployment systems and methods for such advantageous heart valve prostheses are also needed.

These and other needs are addressed by the disclosed prosthesis designs and deployment systems/methodologies, as will be apparent from the detailed description which follows.

SUMMARY

Advantageous valve prosthesis systems and methods/systems for placement of valve prostheses are disclosed herein. In exemplary embodiments of the present disclosure, a mitral valve prosthesis is provided that is adapted for secure and aligned placement relative to a heart annulus. The disclosed valve prosthesis systems may be placed in a non-invasive manner, e.g., via trans-catheter techniques, and may be positioned/repositioned until proper alignment and positioning is achieved.

An exemplary valve prosthesis includes a resilient ring, a plurality of leaflet membranes mounted with respect to the resilient ring, and a plurality of positioning elements movably mounted with respect to the flexible ring, each of the positioning elements defining a first tissue engaging region and a second tissue engaging region spaced from the first tissue engaging region. The positioning elements are advantageously adapted to substantially completely invert by rotating relative to the resilient ring between a first position in which each of the first and second tissue engaging regions is inwardly directed for facilitating positioning of the valve prosthesis within a delivery catheter, and a second position in which each of the first and second tissue engaging regions is outwardly directed for engaging tissue.

The tissue engaging regions may include or define various features and/or structures. Thus, in an exemplary embodiment, the tissue engaging regions define a tissue engaging arc. In further exemplary embodiments, the tissue engaging regions may define a plurality of tissue engaging spikes, a plurality of tissue engaging teeth or a combination thereof. The positioning elements are generally resilient and adapted to resiliently deflect to engage tissue disposed between the first and second tissue engaging regions. The positioning elements may define a set of spaced jaws that are adapted to move with respect to each other, and the first and second tissue engaging regions may be defined by respective opposing jaw portions directed toward each other for engaging tissue disposed therebetween.

In further exemplary embodiments of the present disclosure, one or more of the tissue engaging regions may define a resilient coil that is adapted to be uncoiled as against a coiling bias to permit an outwardly directed end of the uncoiled coil to engage tissue. A third tissue engaging region may be defined by the positioning elements, and such third tissue engaging region may define a plurality of tissue engaging holes, a plurality of tissue engaging barbs/spikes, or a combination thereof.

The disclosed resilient ring generally includes multiple instances of a hoop segment that define a hoop plane and are separated by a corresponding number of gaps within the hoop plane. Coupling segments may be provided that extend vertically relative to the hoop plane, the coupling segments advantageously defining a spring having two leaves joined at a bend region for imparting an elastic force on the hoop segments. Suture-accommodating notches may be provided for use in securing leaflet membranes with respect to the resilient ring. The resilient ring typically defines a circular or elliptical peripheral geometry.

The positioning elements are typically biased in favor of rotating away from the first position and toward the second position within a plane defined by the inversion. Such inversion generally involves, at least in part, rotation outward and away from the first position, and toward and into the second position, in an overturning motion with respect to the flexible ring. A hub may be disposed substantially centrally with respect to the resilient ring, and a plurality of legs may be directed radially with respect to the resilient ring. The legs are generally mounted with respect to the hub and a positioning element. The legs may include an intermediate joint and corresponding leg lengths extending from the joint for allowing the leg to collapse against itself to facilitate the positioning element to assume the first position. Indeed, the legs may include intermediate joints and corresponding leg lengths extending therefrom for forming a spring to bias the positioning element outward and away from the first position and toward the second position when the positioning element is in the first position. The legs may also form springs to bias the positioning element away from the second position and back toward the first position when the positioning element is in the second position.

A joint may be defined between the hub and the leg for forming a second spring to bias the positioning element away from the second position and back toward the first position when the positioning element is in the second position. In exemplary embodiments, the hub is disposed at an elevation below that of the resilient ring when the positioning element is in the first position and, upon the positioning element rotating away from the first position and into the second position, the hub shifts upward to an elevation even with or above that of the resilient ring.

The disclosed legs may include an intermediate joint and corresponding leg lengths extending from the joint for forming a spring to bias the positioning element either outward and away from the first position and toward the second position, or away from the second position and back toward the first position, depending on whether the positioning element is in the first position or the second position, respectively. Each positioning element is generally adapted to invert by rotating away from the first position and toward and into the second position in a first direction to define an inversion plane, and is further adapted to be rotated further within the inversion plane in the first direction from the second position to a third position in which a distal one of the first and second tissue engaging elements is directed substantially downward for dilating obstructing tissue during a process of advancing the valve prosthesis downward into an anatomical annulus for implantation with respect thereto. In such exemplary embodiments, the positioning elements are typically biased in favor of rotating away from the third position and toward the second position within a plane defined by the inversion when the positioning element is in the third position.

Each positioning generally includes a pair of apertures for permitting the positioning element to be releasably engaged by a filament looped through the apertures of the pair thereof. The filament may be used by a practitioner to urge/cause the positioning element to rotate within a plane defined by the inversion. The leaflet membranes are generally fabricated from xenographic materials. The valve prosthesis is adapted to be implanted with respect to an anatomical annulus such that the first tissue engaging region engages tissue associated with a proximal portion of the anatomical annulus, and the second tissue engaging portion engages tissue associated with a distal portion of the anatomical annulus.

The disclosed valve prosthesis may also include a valve skirt that is mounted with respect to the resilient ring. The valve skirt typically extends to an elevation below that of the resilient ring and may also extend to an elevation above that of the resilient ring. The valve skirt may define a variable thickness, e.g., a tapering thickness.

The disclosed valve prosthesis is advantageously adapted for trans-catheter delivery. Thus, in exemplary embodiments, the flexible ring and each positioning element are adapted to be collapsed to an extent sufficient to permit the same to be lodged together in a catheter lumen, e.g., a lumen of 26 French or less.

Additional advantageous features, structures and functions associated with the disclosed valve prosthesis will be apparent from the description of exemplary embodiments which follows, particularly when read in conjunction with the accompanying figures.

BRIEF DESCRIPTION OF THE FIGURES

To assist those of ordinary skill in the art in making and using the disclosed valve prosthesis system and associated deployment systems/methods, reference is made to the accompanying figures wherein:

FIGS. 4A, 4B, 4C, 4D, 4E, 4F, 4G, 4H, and 4I are schematic views illustrating percutaneous placement of a heart valve prosthesis relative to an annulus according to an exemplary embodiment of the present disclosure;

DESCRIPTION OF EXEMPLARY EMBODIMENT(S)

Advantageous valve prosthesis systems and deployment systems/methods are provided according to the present disclosure. The disclosed systems and methods permit surgeons/clinicians to improve heart valve function without invasive surgical intervention. Indeed, the disclosed valve prosthesis systems permit a heart valve prosthesis to be percutaneously delivered to a desired anatomical location. Once located in the desired anatomical region/locale, the disclosed valve prosthesis system facilitates secure and aligned placement of a heart valve prosthesis relative to a heart annulus. Percutaneous delivery of the disclosed heart valve prosthesis as disclosed herein provides for efficient and effective clinical placement of a heart valve prosthesis. The disclosed heart valve prosthesis and associated delivery techniques offer numerous clinical benefits, including enhanced valve function without the need to remove existing valve leaflets, an ability to effectively and efficiently deliver a valve prosthesis percutaneously, and an ability to position and reposition a valve prosthesis relative to an annulus to ensure proper orientation relative to anatomical features.

Figure 1:
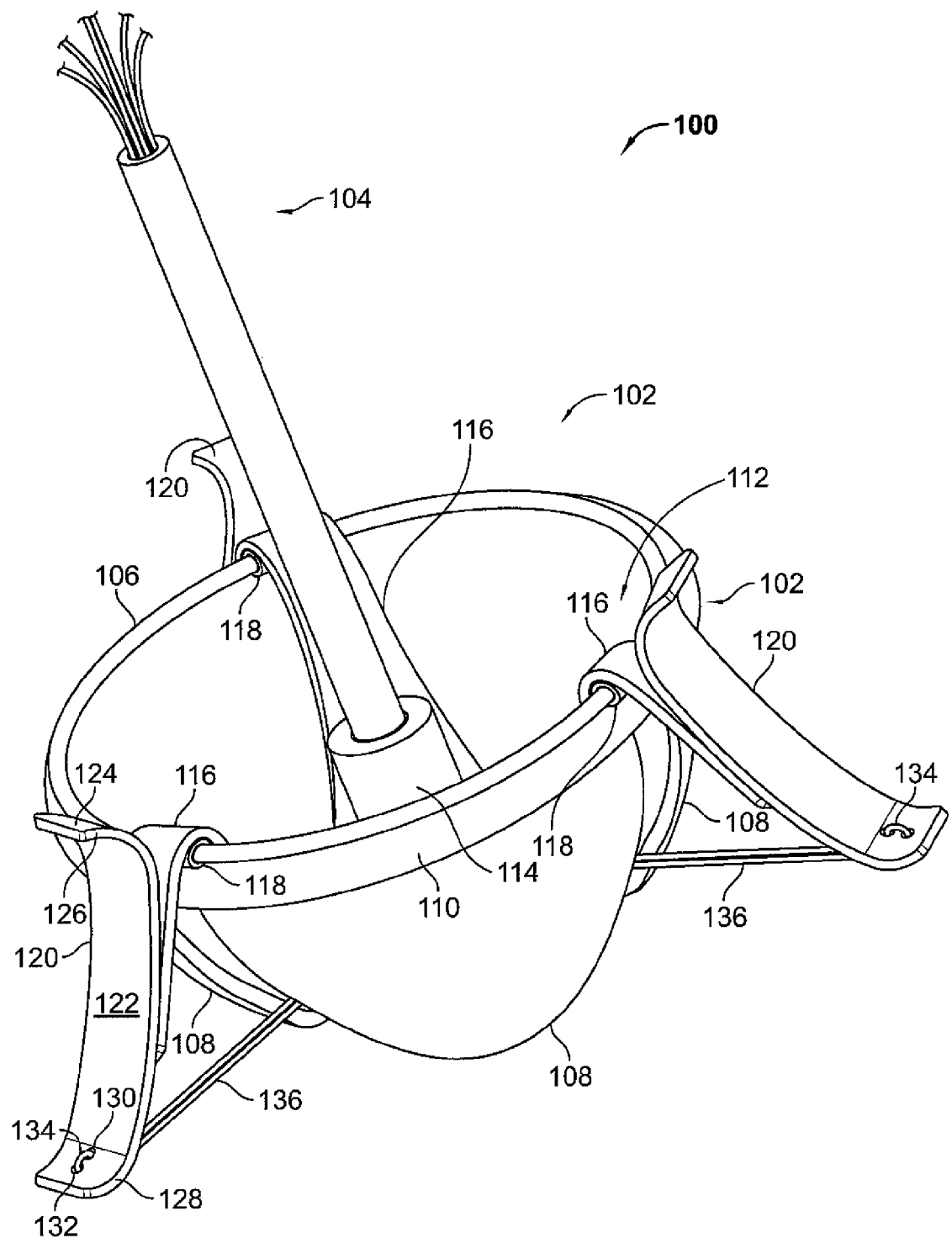
FIG. 1 is a downward perspective of an exemplary valve prosthesis system according to the present disclosure.

With initial reference to FIG. 1, an exemplary valve prosthesis system 100 is schematically depicted. The valve prosthesis system 100 includes a heart valve prosthesis 102 and a delivery structure 104. The valve prosthesis 102 includes a flexible ring 106. Mounted with respect to the flexible ring 106 are a plurality of leaflet membranes 108, a valve skirt 110, and a resilient element 112. The resilient element 112 may include a hub 114 and a plurality of legs 116, each of the legs 116 extending from the hub 114 (e.g., in a regular radial arrangement, as shown in FIG. 1) and being movably mounted with respect to the flexible ring 106 via individual ones of a corresponding plurality of mounting elements 118. The valve prosthesis 102 may further include a corresponding plurality of positioning elements 120, each such positioning element 120 being attached to one of the legs 116 of the resilient element 112.

As shown in the exemplary embodiment of FIG. 1, the valve prosthesis 102 may include three (3) leaflet membranes 108, each leaflet membrane 108 assuming an inwardly bowed orientation when mounted with respect to the flexible ring 106. More or fewer of the leaflet membranes 108 may be employed without departing from the spirit or scope of the present disclosure, provided the desired blood flow functionality is achieved. The leaflet membranes 108 may be fabricated from xenograft tissue, e.g., the valve leaflets may be fabricated from standard biologic or artificial prosthetic material, such as cryo- or chemically-preserved bovine pericardium or porcine heart valve tissue. Synthetic membrane materials may also be employed in the fabrication of the leaflet membranes 108, e.g., fiber-reinforced matrix materials. The leaflet membranes 108 may be secured with respect to the flexible ring 106 through conventional means, e.g., creation of an annulus and/or cuff that surrounds, in whole or in part, the flexible ring 106 such that each of the plurality of leaflet membranes 108 extends downwardly with respect to the flexible ring 106.

With further reference to FIG. 1, the valve skirt 110 may extend to a full extent of the flexible ring 106, e.g., to a full extent of the circumference of the flexible ring 106. The valve skirt 110 may be formed from a single, contiguous structure, or may be defined by a plurality of adjacent and/or overlapping elements that, together, extend along the circumference of flexible ring 106. According to exemplary embodiments of the present disclosure, the valve skirt 110 may be sutured with respect to the flexible ring 106. Alternatively, a cuff may be formed at an edge of the valve skirt 110, such cuff being adapted to receive the flexible ring 106 therewithin. The cuff may extend along the entire edge of the valve skirt 110 or may be defined at discrete intervals along the length of the valve skirt 110, such that the valve skirt 110 is mounted with respect to the flexible ring 106 at spaced intervals. The valve skirt 110 may be fabricated from a variety of substantially flexible and/or pliable materials, e.g., xenographic tissue or a synthetic material that is compatible with blood flow, e.g., a non-thrombogenic material. Indeed, in an exemplary embodiment of the present disclosure, the valve skirt 110 and the leaflet membranes 108 may be fabricated as integral/contiguous structures, e.g., from a desired xenographic and/or synthetic material, and such integral/continuous structure may be advantageously mounted with respect to the flexible ring 106 such that the functionalities of both elements (i.e., leaflet membrane functionality and valve skirt functionality) are achieved.

The thickness of the valve skirt 110 may be substantially uniform from edge-to-edge or may vary along its length. For example, in an exemplary embodiment of the present disclosure, it is contemplated that the valve skirt 110 would be thicker in a region thereof adjacent the flexible ring 106 and thinner in a region thereof relatively more distant from the flexible ring 106, thereby enhancing the flexibility of the valve skirt 110 in the latter region to provide more effective sealing functionality relative to adjacent anatomical structures/tissue. The thicker region adjacent the flexible ring 106 may serve to reduce the likelihood of the valve skirt 110 disengaging from the flexible ring 106.

Although the exemplary embodiment of FIG. 1 depicts the valve skirt 110 extending in a single direction relative to the flexible ring 106, i.e., downward, it is contemplated according to the present disclosure that the valve skirt 110 may extend both upwardly and downwardly relative to the flexible ring 106. In some such implementation of the valve skirt 110, the attachment means for securing the valve skirt 110 relative to the flexible ring 106 would not necessarily be located at an edge thereof. Rather, such attachment means, e.g., cuff(s) and/or suturing, may be positioned along an intermediate line/region of the valve skirt 110. In this way, a first portion of the valve skirt 110 would be free to extend above the flexible ring 106, and a second portion of the valve skirt 110 would be free to extend below the flexible ring 106. Both portions of the valve skirt 110, i.e., the portions above and below the flexible ring 106, would advantageously function to seal the valve prosthesis 102 relative to a patient's anatomy when the valve prosthesis 102 is deployed relative thereto, as described in greater detail below. Of note, a portion of the valve skirt 110 extending above the flexible ring 106 may include a notch or discontinuity to accommodate structures associated with the positioning elements 120, as described in greater detail below. The valve skirt 110 may have a downward length that is effective to achieve a desired level of sealing relative to surrounding anatomical structures. For Example, the valve skirt 110 may have a downward length of about five (5) millimeters to about fifteen (15) millimeters relative to the flexible ring 106. Similar dimensions are contemplated for the upward extending portion of the valve skirt 110 in implementations wherein the valve skirt 110 extends both above and below the flexible ring 106.

For greater security/stability, the valve skirt 110 may be tacked or otherwise secured in at least some manner relative to the resilient element 112 (e.g., to one or more of the legs 116 of the resilient element 112). In an alternative embodiment, the valve skirt 110 may be positioned radially outward of the positioning elements 120.

As shown in FIG. 1, the resilient element 112 may include three (3) legs 116 mounted in a circumferentially-spaced manner with respect to the flexible ring 106 via the mounting elements 118. Each leg 116 may be configured or adapted to include or assume an arcuate shape or bend in the vicinity of the flexible ring 106. The legs 116 may be spaced by about 120° relative to each other, although an alternative number and/or spacing of the legs 116 may be employed without departing from the spirit or scope of the present disclosure. The mounting elements 118 may be of any suitable shape, design, configuration, and/or attachment technique relative to the legs 116 to permit rotational and/or overturning motion of the legs 116 relative to the hub 114, and/or relative to the flexible ring 106. For example, the mounting elements 118 may be substantially C-shaped, and/or tube shaped. The mounting elements 118 may, for example, be affixed to respective undersides of the legs 116 (e.g., within an arcuate or bent portion thereof) through an appropriate mounting technique, e.g., a tack weld.

Returning to the potential interplay between the legs 116 of the resilient element 114 and the valve skirt 110, the mounting elements 118 may overlay the valve skirt 110 to the extent that the valve skirt 110 is secured to the flexible ring 106 in such circumferential region. Further, the valve skirt 110 may be tacked, adhered or otherwise joined to the underside of one or more of the legs 116 where the same extend over the valve skirt 110.

With further reference to FIG. 1, each of the positioning elements 120 may be shaped, configured, and/or otherwise adapted to engage tissue, and/or to position the valve prosthesis 102 relative to tissue. For example, each positioning element 120 may define an outer surface 122, an inner surface 124 opposite the outer surface 122, an upper arcuate region 126, and a lower arcuate region 128 opposite the upper arcuate region 126. Each of the positioning elements 120 may be coupled (e.g., fixedly joined) to a corresponding leg 116 of the resilient element 112, e.g., through a weld between the inner surface 124 of the positioning element 120 a corresponding outer surface of the leg 116. The positioning elements 120 may be dimensioned such that the upper arcuate regions 126 thereof extend above the flexible ring 106 (e.g., when the valve prosthesis 102 assumes the orientation depicted in FIG. 1). The upper and lower arcuate regions 126, 128 of the positioning elements 120 may be spaced by a distance that facilitates positioning of the valve prosthesis 102 relative to a heart annulus, as described in greater detail below. For example, the upper and lower arcuate regions 126, 128 may be spaced by between about seven (7) millimeters and about twenty-five (25) millimeters. The positioning elements 120 and the legs 116 may be fabricated from a material that permits at least some degree of flexibility/deformation (e.g., elastic deformation), such as stainless steel or Nitinol of an appropriate thickness/gauge. Other materials for the positioning elements 120 and/or the legs 116 are possible.

The lower arcuate regions 128 of the positioning elements 120 may include a pair of spaced apertures 130, 132. The delivery structure 104 may include a plurality of filaments or cords 134, each cord 134 being threaded through a positioning element 120 via the pair of spaced apertures 130, 132 formed therein, such that separate lengths 136 of the cord 134 extend away from the apertures 130, 132 and radially inwardly toward the hub 114 of the resilient element 112. As may be more clearly seen in FIG. 2, the hub 114 of the resilient element 112 may include one or more lumen(s) 200 (e.g., a centrally-located lumen 200), the delivery structure 104 may include a delivery tube 202 having one or more corresponding lumens 204 (e.g., an axially located lumen), and the lengths 136 of the cords 134 may pass from the respective lower arcuate regions 128 of the positioning elements 120 toward the hub 114, into and through the lumen 200 thereof, and into and through the lumen 204 of the delivery tube 202. Such lengths 136 of the cords 134, and/or such routing of such lengths 136 of such cords 134 from the lower arcuate regions 128 of the positioning elements 120 and via the hub 114 and/or the delivery tube 202, may facilitate deployment of the valve prosthesis 102 relative to an annulus and/or associated heart tissue.

The delivery tube 202 may be flexible, and the lumen or lumens 204 may accommodate passage of a plurality of lengths 136 of cords 134. In the exemplary embodiment of FIGS. 1 and 2, three (3) positioning elements 120 are associated with the valve prosthesis 102 and each positioning element 120 interacts with a separate cord 134. Thus, the respective lumen(s) 200, 204 of the hub 114 and the delivery tube 200 may be appropriately sized and/or of an appropriate number to accommodate least six (6) separate lengths 136 of cords 134, based on the looping of each cord 134 through a pair of spaced apertures 130, 132 formed at or near the respective lower arcuate regions 128 of the positioning elements 120.

Figure 2:
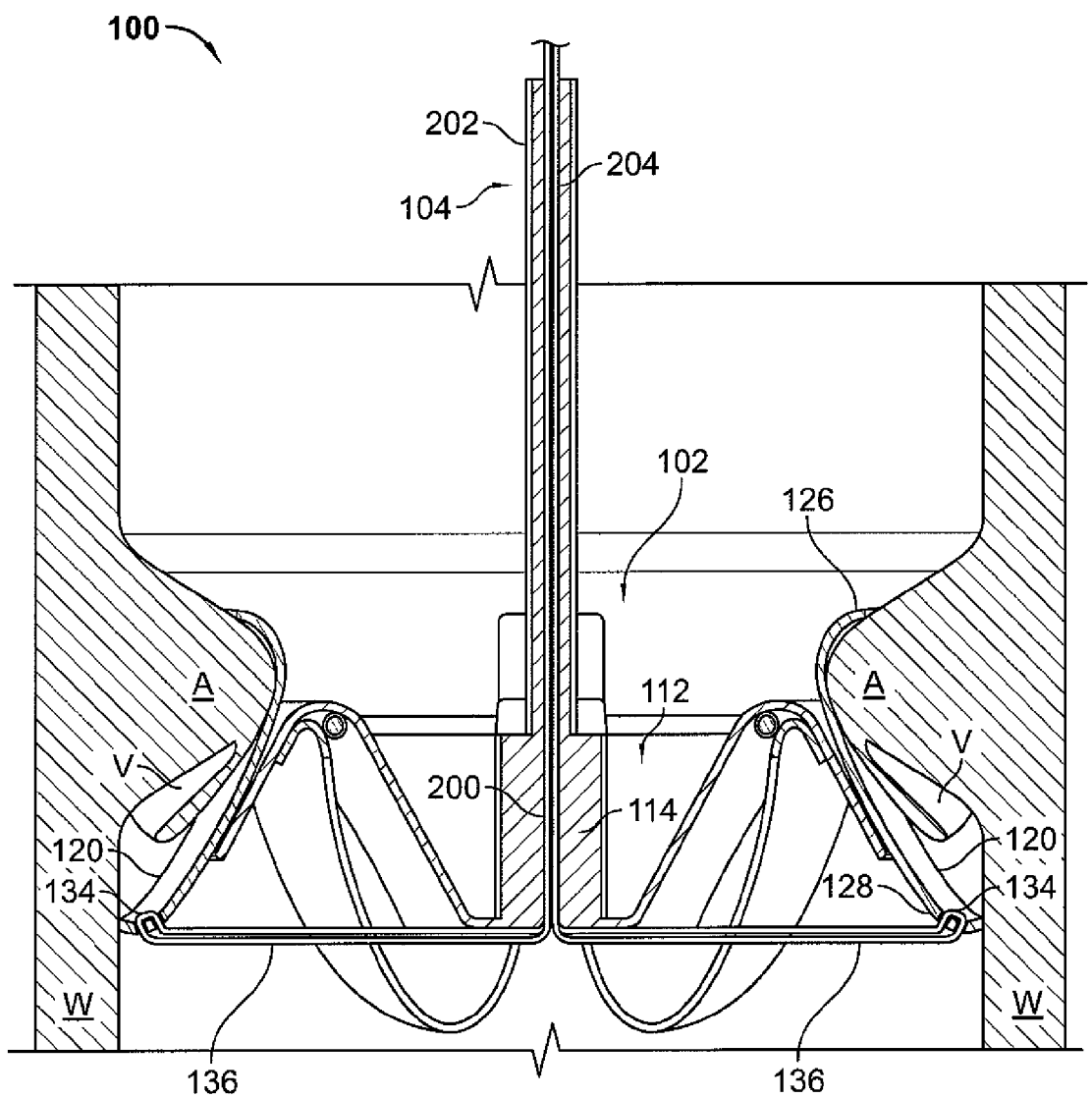
FIG. 2 is a partially-sectional side view of an exemplary valve prosthesis system according to the present disclosure positioned relative to a heart annulus.

As is also apparent from the cross-sectional view of FIG. 2, the legs 116 of the resilient element 112 may cooperate with the hub 114 thereof and/or with the flexible ring 106 to provide stability to the valve prosthesis 102, e.g., during the deployment process, and/or during the useful life of the valve prosthesis 102 in situ. The structural interaction between the legs 116 and the flexible ring 106, and/or between the legs 116 and the hub 114, permits a surgeon/clinician to utilize the lengths 136 of the cords 134 and the delivery structure 104 to remotely operate the valve prosthesis 102 (e.g., to remotely move/rotate the legs 116 relative to the flexible ring 106 and/or relative to the hub 114). Each of the legs 116 may, for example, include one or more joints along its respective length (e.g., one or more living hinges at or near a mid-point thereof) to facilitate collapse of valve prosthesis 102 for catheter-based delivery thereof. In embodiments in accordance with the present disclosure, one or more such joints may store energy so as to facilitate the delivery of a spring force to expand the flexible ring 106 to a full diameter thereof (or at least a substantial fraction thereof), or assist in an otherwise substantially self-powered expansion thereof, upon deployment of the valve prosthesis 102 in situ. In embodiments in accordance with the present disclosure, one or more such joints may further store energy so as to urge the positioning elements 120 radially outward (e.g., toward secure engagement with corresponding tissue, and/or radially outward from a compressed shape associated with intra-catheter delivery). According to at least some exemplary embodiments of the present disclosure, three (3) legs 116 may extend from the hub 114, such that the resilient element 112 assumes a 'tripod'-type shape for expanding and/or supporting the valve prosthesis 102 (e.g., helping the flexible ring 106 to assume and/or maintain a shape consistent with the intended function of the valve prosthesis 102, and/or to urge the positioning elements 120 radially outward) during deployment and/or while implanted in situ.

With further reference to FIG. 2, the valve prosthesis 102 of the valve prosthesis system 100 is depicted in alignment and engagement with an heart valve annulus "A" and a heart wall "W" of a patient. The valve prosthesis 102 is further shown displacing heart valve leaflet structure "V" (e.g., the valve prosthesis 102 is implanted within the annulus A for purposes of providing the valve function for which the valve leaflet structure V is no longer well suited). The annulus A is depicted in an enlarged and symmetric fashion for ease of description. The actual geometric and dimensional details of the relevant anatomical structures are well known to persons skilled in the art. As shown in FIG. 2, each of the upper arcuate regions 126 of the respective positioning elements 120 may be positioned advantageously so as to engage a corresponding part of an upper portion of the annulus A. In this fashion, at least, the positioning elements 120 may be employed in cooperation with each other to align the valve prosthesis 102 relative to the annulus A. As also shown in FIG. 2, each of the lower arcuate regions 128 may be positioned advantageously so as to engage a corresponding part of the wall W below the annulus A. In this fashion, at least, the positioning elements 120 may be employed in cooperation with each other to stabilize and secure the valve prosthesis 102 relative to the overall anatomical environment.

In the event the surgeon/clinician is or becomes dissatisfied with the position/orientation of valve prosthesis 102 relative to the annulus A or the wall W, or has or develops some other concern or uncertainty with respect to the deployment of the valve prosthesis 102, he/she may deflect the lower arcuate regions 128 of the positioning elements 120 inward by pulling or otherwise manipulating or moving the respective lengths 136 of the cords 134 a sufficient extent radially inwardly and/or upwardly through the hub 114 and the delivery tube 202 to cause the lower arcuate regions 128 of the positioning elements 120 to disengage from the wall W. The surgeon/clinician may then reposition the structure of the valve prosthesis 102 relative to the overall anatomical environment by pulling, pushing, or otherwise manipulating or moving the delivery tube 202 to a desired extent with respect to the delivery catheter (not separately shown). Such manipulation may, for example, be translated to the valve prosthesis 102 via the hub 114 and the legs 116 of the resilient element 112. In accordance with embodiments of the present disclosure, after delivering the valve prosthesis 102 to the position with respect to the annulus A shown in FIG. 2, the surgeon/clinician may elect to pull the valve prosthesis 102 at least partially back upward, causing the lower arcuate regions 128 of the positioning elements to engage a corresponding part of a lower portion of the annulus A, and/or to engage the heart valve leaflet structure V, which in at least some instances results in the valve prosthesis 102 to be lodged and/or anchored in a particularly secure fashion within the annulus A.

Once satisfied with the position of the valve prosthesis 102 relative to the annulus A and/or the wall W, the surgeon/clinician may withdraw the cords 134 from the valve prosthesis 102 through the delivery tube 202 by pulling outward on one length 136 thereof to a sufficient extent while leaving the other length 136 loose. The surgeon/clinician may further withdraw the remainder of the delivery structure 104 from the valve prosthesis 102 by separating the delivery tube 202 from the hub 114 of the resilient element 112. Means for disconnecting the delivery tube 202 from the hub 114 may take a variety of forms, e.g., a screw thread arrangement at the end of the delivery tube 202 that may be disengaged from a corresponding socket associated with the hub 114. Still further (e.g., alternative) connection and/or disconnection means are possible, including bayonet lock mechanisms, detent engagement mechanisms, and the like, at least some of which are further described hereinbelow.

Tissue-engaging features, e.g., barbs, tacks or the like, may be formed on, in, and/or through one or more tissue-engaging surfaces of the respective positioning elements 120. For example, such features may be formed on the outer surface 122 of the positioning elements 120, e.g., within the upper and/or lower arcuate regions 126, 128. Additionally, surface treatments and/or adjunct structures may be associated with the positioning elements 120 to promote tissue in-growth, thereby further enhancing the stability/security of an implanted valve prosthesis according to the present disclosure. For example, a biologic coating and/or a material or fabric that promotes tissue in-growth, e.g., DACRON™ material, may be applied to a desired portion/region of the respective outer surfaces 122 of the positioning elements 120.

The disclosed valve prostheses and valve prosthesis systems and methods have applicability in a variety of anatomical regions, e.g., as a prosthesis for the mitral valve, aortic valve, pulmonary valve, or tricuspid valve. Embodiments of the disclosed valve prostheses have particular applicability for mitral valve applications. Depending on the desired clinical application, the valve prosthesis system 100 and/or the valve prosthesis 102 may be sized and dimensioned to accommodate such use by adapting the annular ring to fit in the requisite anatomical space, e.g., a mitral, aortic, pulmonary, or tricuspid valve opening of the heart.

Figures 3A, 3B:
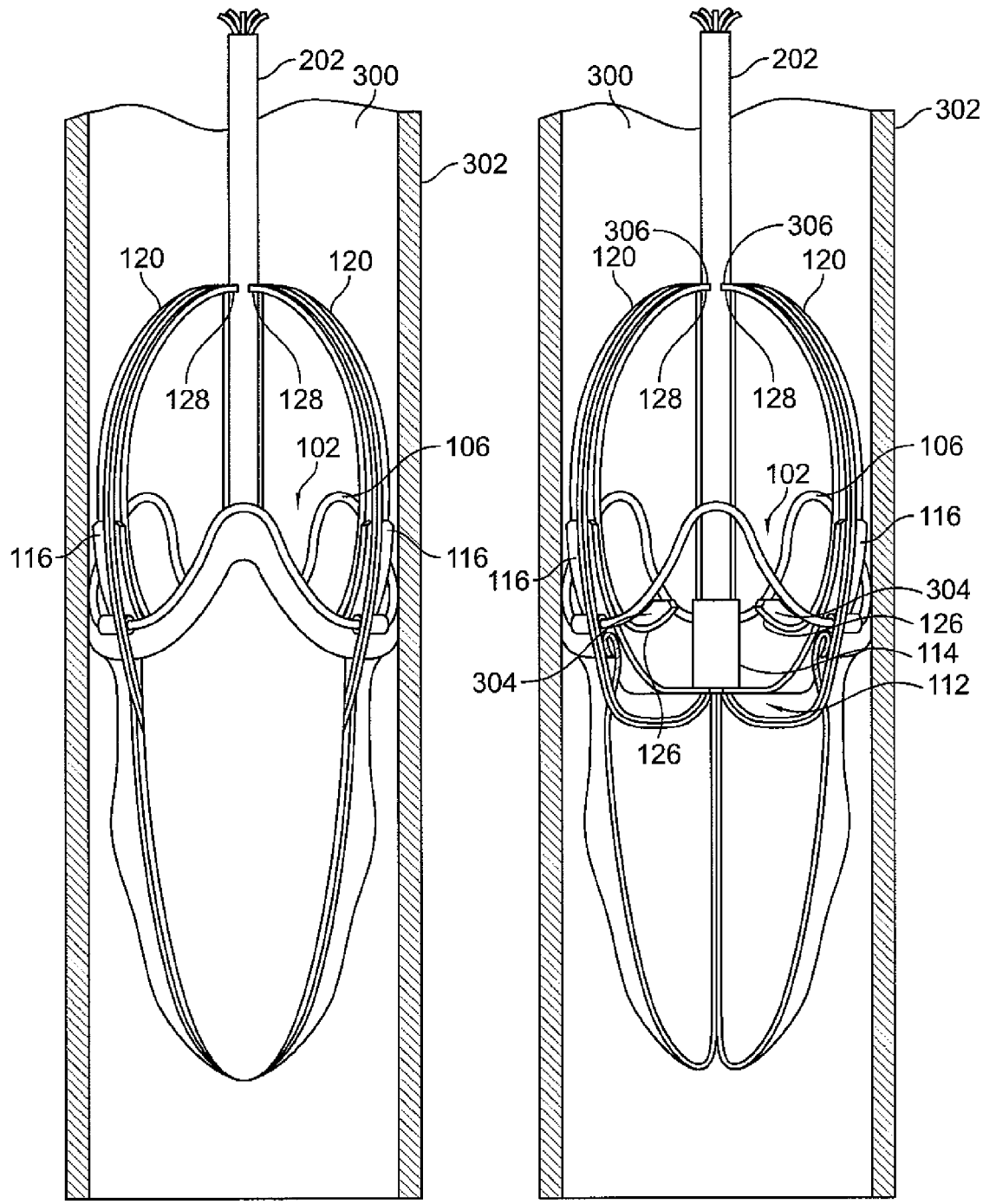
FIG. 3A is a side view of an exemplary prosthesis system according to the present disclosure, wherein an exemplary heart valve prosthesis is positioned within an exemplary delivery structure.
FIG. 3B is a partially-sectional side view of the exemplary prosthesis system of FIG. 3A, also shown positioned within the exemplary delivery structure.

Turning to FIGS. 3A and 3B, the heart valve prosthesis 102 may assume a collapsed configuration within a lumen 300 of a catheter 302. Additionally, the positioning elements 120 may be substantially inverted, e.g., rotated approximately 180° relative to the flexible ring 106 to which they are mounted and relative to the hub 114 of the resilient element 112, as compared to the relative positions or orientations the positioning elements 120 may tend to occupy with respect to such structure (e.g., as shown in FIG. 1) when not being subjected to the application of opposing outside forces. The flexible ring 106 may also be substantially deformed and the legs 116 of the resilient element 112 may be deflected so as to permit the valve prosthesis 102 to fit within the catheter 302. In this inverted orientation, the upper and lower arcuate regions 126, 128 associated with the respective positioning elements 120 may be inwardly directed toward the delivery tube 202. In an exemplary embodiment of the present disclosure, the upper and lower arcuate portions 126, 128 of the respective positioning elements 120 may be associated with and/or terminate in respective tips 304, 306, and such tips 304, 306 may feature cut-outs (not shown in FIGS. 3A and 3B), e.g., arcuate notches, such cut-outs being adapted to cooperate with a substantially cylindrical geometry of the delivery tube 202 when the positioning elements 120 are in the substantially inverted orientations depicted in FIGS. 3A and 3B.

Figure 4D:
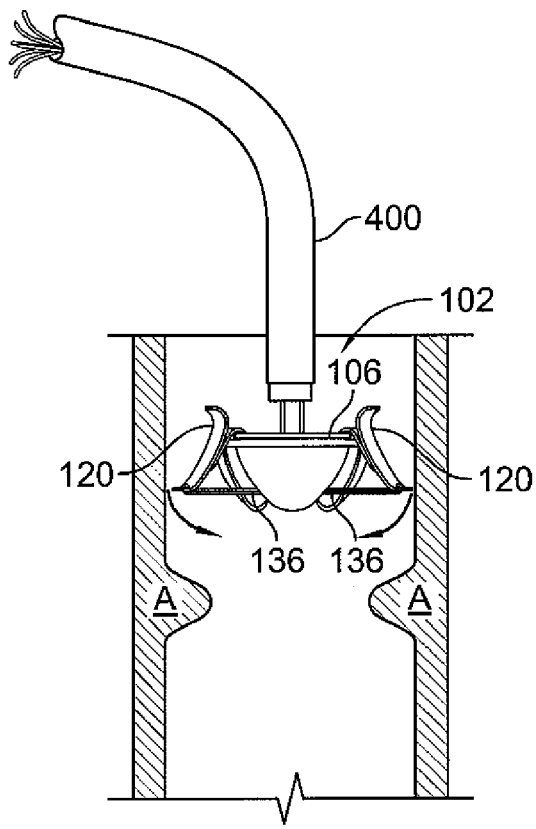

Turning to FIGS. 4A-4I, an exemplary sequence of steps for percutaneously delivering and positioning the disclosed valve prosthesis 102 in a desired anatomical location are schematically depicted. As shown in FIGS. 4A-4C, the valve prosthesis 102 may be navigated to the desired anatomical location, e.g., adjacent a mitral valve, aortic valve, pulmonary valve, or tricuspid valve, within a delivery catheter 400 having a distal end 402. In accordance with embodiments of the present disclosure, the valve prosthesis 102 may be delivered to the mitral valve cavity transseptally or by direct venous or arterial delivery to the aortic valve, pulmonary valve, or tricuspid valve cavities. In exemplary embodiments, the valve prosthesis may be navigated to a desired location using a guide wire (not shown) that cooperates with a corresponding guide wire lumen (not shown) formed in or otherwise present within the delivery catheter 400. The valve prosthesis 102 may be advanced through the delivery catheter 400 along an associated guide wire in a collapsed/inverted orientation (by being pushed, for example, by the delivery tube 202) to the implantation position (e.g., left atrium for mitral valve) where the valve prosthesis 102 is deployed adjacent the diseased valve for subsequent implantation therein. Alternatively, the valve prosthesis 102 may be pre-positioned within the delivery catheter 400 at or near the distal end 402, and both the valve prosthesis 102 and the distal end 402 of the delivery catheter 400 may be so advanced in unison along an associated guide wire.

Once a distal end 402 of the delivery catheter 400 has been delivered to within the necessary proximity of the desired anatomical location, e.g., annulus "A", the delivery tube 202 may be extended relative to the delivery catheter 400 to push the valve prosthesis 102 outward of the catheter via a corresponding opening in the distal end 402. Upon the valve prosthesis 102 exiting the distal end 402, resilient properties of several components of the valve prosthesis 102, particularly the flexible ring 106 and the legs 116 of the resilient element 112 (FIG. 2), may cause at least the flexible ring 106 to automatically resume its non-deformed/uncompressed shape (e.g., as seen in FIG. 4B as well as all later figures in the sequence of FIGS. 4A-4I), which may be, for example, a circle, an ellipse, or the like. As best seen in FIG. 4C, upon the surgeon/clinician allowing the valve prosthesis 102 to emerge from the delivery catheter 400, yet without any further positive action on the part of the surgeon/clinician, the valve prosthesis 102 may tend eventually to fully relax, and assume a generally non-deformed orientation, wherein the positioning elements 120 are seen to have overturned or become inverted by rotating both outwardly and downwardly past the horizontal (e.g., so that the outer surfaces 122 thereof face generally outward again, and the upper and lower arcuate regions 126, 128 thereof are, once again, outwardly directed). The valve skirt 110 may be appropriately substantially downwardly oriented and positioned for performing an advantageous sealing function (e.g., as against valve prolapse) upon being positioned in a desired anatomical position.

Figure 4E:
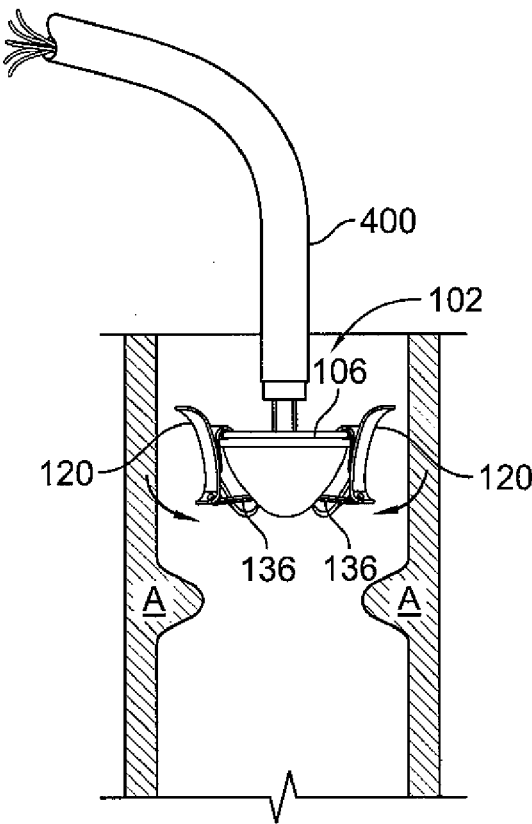
Figure 4F:
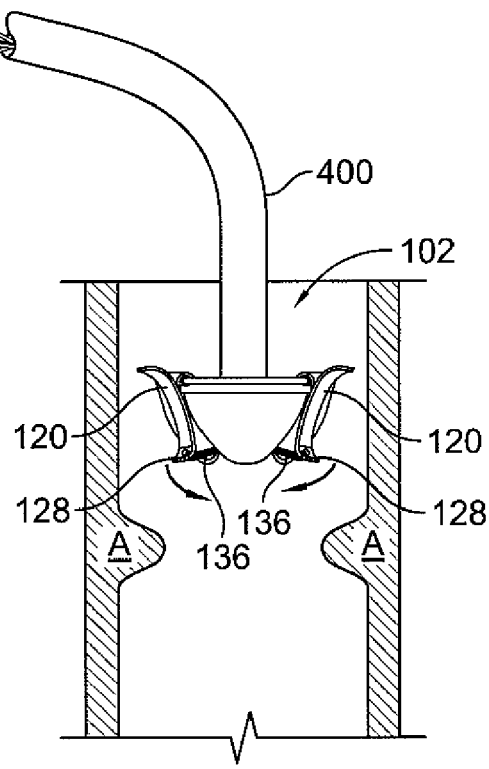
Figure 4G:
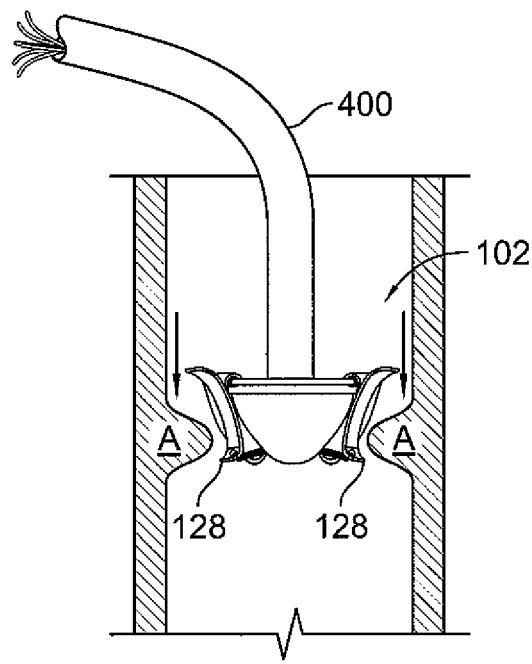
Figure 4H:
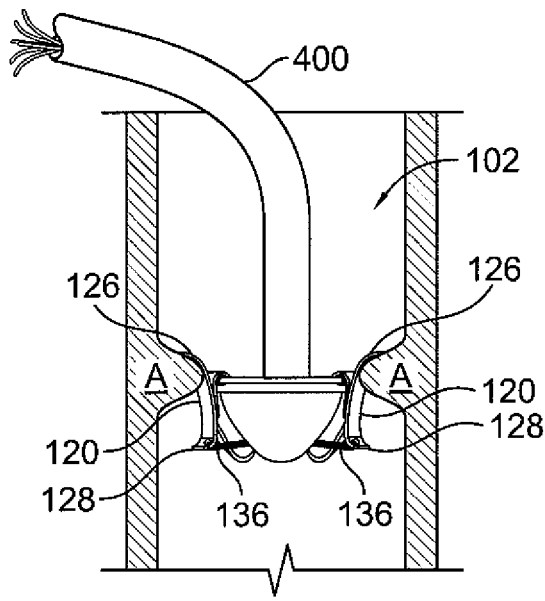

From the orientation of the valve prosthesis 102, and more particularly, of the positioning elements 120 thereof, shown in FIG. 4C, the surgeon/clinician may deflect the lower arcuate regions 128 of the positioning elements 120 inward by pulling the respective lengths 136 of the cords 134 (FIG. 2) a sufficient extent radially inward toward, and/or upward through, the hub 114 (FIG. 2) and the delivery tube 202 in such a way as to continue (see FIG. 4D) an overturning or inverting motion of the positioning elements 120 relative to the flexible ring 106 and the hub 114 (FIG. 2), progressing through sequential orientations as depicted in FIGS. 4D and 4E and arriving at the particularly notable orientation depicted in FIG. 4F. For example, in accordance with embodiments of the present disclosure, the surgeon/clinician may be permitted to accomplish such deflection of the positioning elements 120 by grasping or otherwise seizing respective proximal ends (not shown) of the lengths 136 of the plurality of cords 134 (FIG. 2) disposed outside the delivery catheter 400 and outside the patient's body and pulling such ends outward of the delivery catheter 400 and the patient's body. Such withdrawal of the lengths 136 of the cords 134 results in the lower arcuate regions 128 of the positioning elements 120 being pulled radially inwardly, e.g., to a point where the tips 306 of the lower arcuate regions 128 extend at least partially downwardly toward the diseased valve. As shown in FIGS. 4G and 4H, such downwardly-directed and relatively more closely spaced lower arcuate regions 128 may be utilized in the manner of a probe or 'plow' to deflect the patient's leaflet membranes (see, e.g., valve structure V in FIG. 2) and/or otherwise facilitate advancing the valve prosthesis 102 downward into the patient's diseased valve such that the valve prosthesis 102 is able to be positioned at an appropriate implantation elevation and an appropriate lateral position relative to the annulus A, As best shown in FIG. 4H, the upper arcuate regions 126 of the respective positioning elements 120 may be cooperatively adapted to be contained within a common plane, e.g., in the manner of a "top hat", so as to facilitate positioning/alignment of the valve prosthesis 102 relative to the annulus A. The circumferentially interrupted aspect exhibited by of the valve prosthesis 102 and collectively defined by the positioning elements 120 may facilitate both inversion of the positioning elements 120 during percutaneous introduction, and effective alignment and tissue engagement/stability upon final implantation and in situ valve function. For example, upon each of the plurality of upper arcuate regions 126 substantially engaging a corresponding part of the upper portion of the annulus A, the valve prosthesis 102 may be generally aligned in a desirable fashion.

Figure 4I:
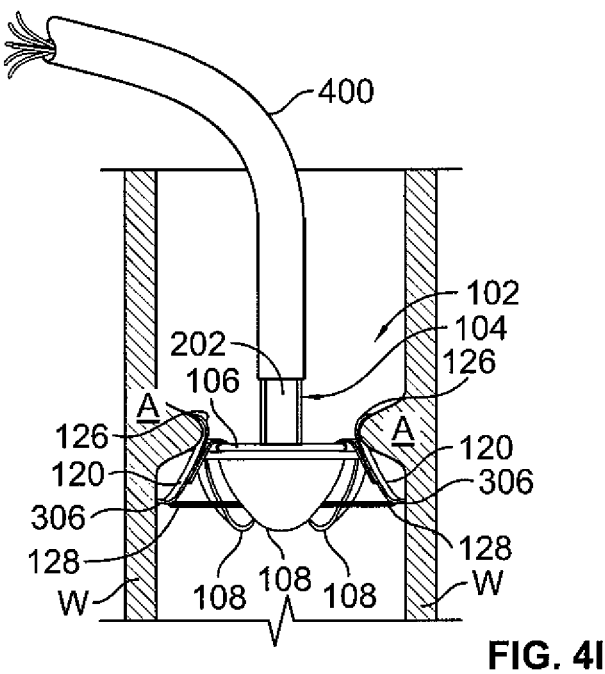

The valve prosthesis 102 may now be further positioned and/or spatially oriented relative to the annulus A in the manner desired by the surgeon/clinician, e.g., as viewed through conventional imaging instrumentation. (Of note, the positioning elements 120 (and particularly, the upper arcuate regions 126 thereof) may be substantially radio-opaque to facilitate imaging identification thereof to confirm proper positioning and spatial orientation of the valve prosthesis 102 relative to the annulus A.) For example, at such time the surgeon/clinician may begin to relax an accumulated degree of tension within the lengths 136 of the plurality of cords 134 (FIG. 2), and thereby begin to allow a corresponding accumulation of energy/spring force contained in the legs 116 (FIG. 2) of the resilient element 112 (FIG. 2) and/or in the positioning elements 120 to cause the lower arcuate regions 128 of the positioning elements 120 to, once again, begin to rotate radially outwardly. Also for example, and as seen in FIG. 4I, the lower arcuate regions 128 may be allowed to rotate radially outward to an extent sufficient to permit the respective tips 306 thereof to contact and/or engage the cardiac tissue comprising the wall W. Having retracted to an extent sufficient to permit such tissue engagement, the legs 116 of the resilient element 112 and/or the positioning elements 120 may still retain sufficient energy/spring force to further cause the respective tips 306 to collectively press against and/or become substantially embedded in place with respect to the wall W. Such collective spring force may be sufficient to permit the lower arcuate regions 128 of the positioning elements 120 to offer a degree of resistance against vertically upward pullout or displacement of the valve prosthesis 102, e.g., a degree of resistance at least comparable to a naturally strong degree of resistance against vertically downward displacement thereof offered by the upper arcuate elements 126 positioned across and/or against the annulus A.

As also seen in FIG. 4I, upon the valve prosthesis 102 being determined to be properly positioned and oriented relative to the annulus A, the cords 134 (FIG. 2) may be withdrawn from the positioning elements 120. Thereafter, the remainder of the delivery structure 104 may be disconnected and/or separated from the valve prosthesis 102 (e.g., the delivery tube 202 may be disconnected from the hub 114 (FIG. 2), thereby leaving the valve prosthesis 102 in an appropriate position relative to the patient's diseased heart valve to serve as a functional replacement thereof. The positioning elements 120 may serve to maintain the native leaflet membranes (see valve structure V in FIG. 2) in an open position, and each of the leaflet membranes 108 and the valve skirt 110 mounted with respect to the flexible ring 106 may function to ensure appropriate directional control of blood flow therethrough.

The disclosed valve prosthesis and associated delivery structures/methods offer numerous advantages relative to existing systems. For example, the positioning elements associated with the disclosed valve prosthesis valve include upper and lower arcuate regions that may advantageously function to engage the annulus as well as the wall of the ventricular chamber below the annulus, thereby securely aligning and stabilizing the valve prosthesis (e.g., in a re-deployable manner) relative thereto. In addition, the invertible and collapsible aspects of the valve prosthesis (e.g., for purposes of catheter introduction and the automatic expansion of the valve prosthesis upon exiting the catheter) may facilitate efficient percutaneous delivery and in situ manipulation of the disclosed valve prosthesis system. Further, the disclosed valve skirt may enhance sealing functionality of the disclosed valve prosthesis when positioned in situ as compared to that which might otherwise be the case (e.g., without such a skirt and/or the annular sealing function provided thereby). Still further, the "top-hat" geometry and/or functionality of the upper arcuate regions of the positioning elements may advantageously function to accurately and securely position the valve prosthesis relative to an annulus and associated anatomical structures.

It will be appreciated that the disclosed design and implantation methodology may not require extensive surgery, and that the disclosed positioning elements may function to provide stable and well aligned implantation, central blood flow, and/or a stable platform for the leaflet membranes. Moreover, positioning may be more precise than with a balloon expandable device, such as a stent. Additionally, and also unlike a stent, the positioning may potentially be repeated (e.g., until the desired implantation position and/or orientation is achieved). The heart valve prosthesis described herein may also allow anchoring relative to the valve annulus in states of the diseased valve in which a stent may not encounter sufficient tissue to which to adhere (e.g., as is commonly the case with respect to mitral valve disease).

In accordance with exemplary embodiments of the present disclosure, the heart valve prosthesis may be placed squarely at the site of a diseased heart valve, as distinct from certain existing heart valve prosthesis implementations characterized by the use of stents configured for placement in the connecting blood vessels adjacent to and/or near the diseased heart valve, and, as such, are designed to be disposed in spaced relation therewith, whether during or after implantation, or during in situ operation. As a result, the ability of the operator or surgeon to reposition and/or re-anchor the heart valve prosthesis in order to more accurately position the heart valve prosthesis in the opening of the diseased heart valve, such as may be provided in accordance with embodiments of the present disclosure, may be of increased significance.

Figure 5:
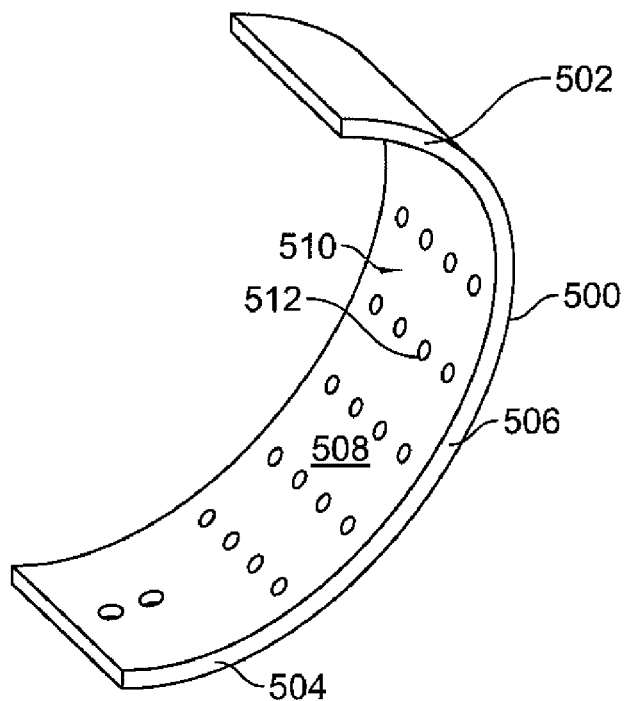
FIGS. 5, 6, and 7 are schematic perspective views of variations of a positioning element according to the present disclosure.
Figure 6:
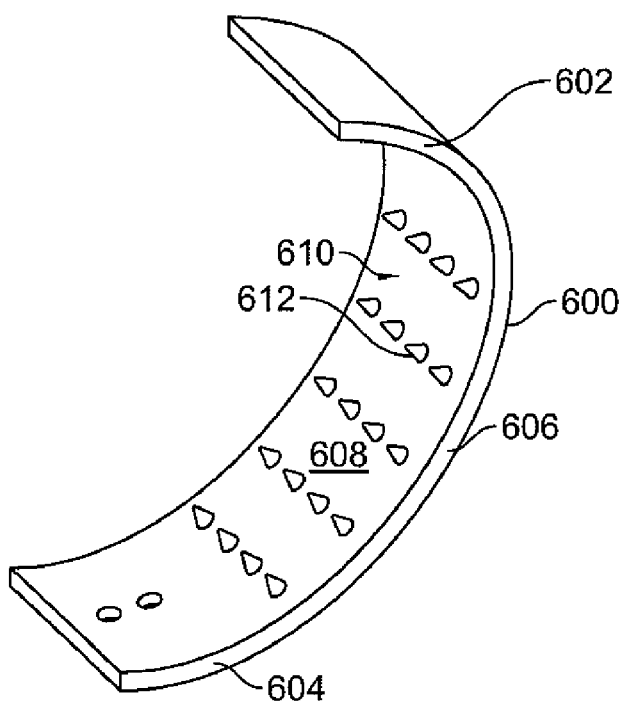
Figure 7:
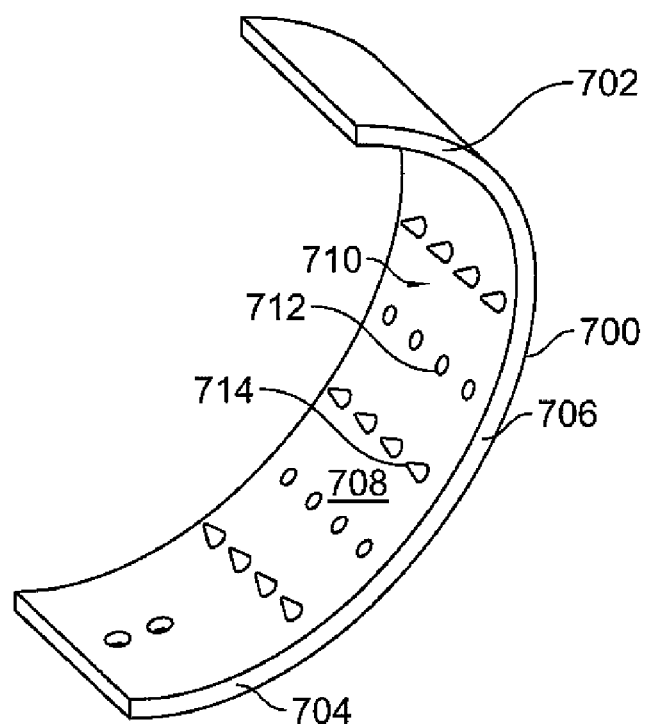

The positioning elements 120 of the present disclosure may be implemented by one or more of a plurality of variations, including those depicted in FIGS. 5-7. More particularly, a positioning element 500 depicted in FIG. 5 is one such variation of the positioning element 120. The positioning element 500 may include upper and lower arcuate regions 502, 504, an intermediate region 506 disposed therebetween, and an outer surface 508. An array 510 of holes 512 may be formed in the outer surface 508 in a vicinity of the intermediate region 506 to encourage in-growth of tissue, increasing positional and orientational stability in situ. Referring now to FIG. 6, a positioning element 600 is another such variation of the positioning element 120. The positioning element 600 may include upper and lower arcuate regions 602, 604, an intermediate region 606 disposed therebetween, and an outer surface 608. An array 610 of spikes or spurs 612 may be provided, extending from the outer surface 608 in a vicinity of the intermediate region 606 to facilitate secure engagement of tissue, similarly increasing positional and orientational stability in situ. A positioning element 700 depicted in FIG. 7 is yet another variation of the positioning element 120. The positioning element 700 may include upper and lower arcuate regions 702, 704, an intermediate region 706 disposed therebetween, and an outer surface 708. An array 710 of holes 712 may be formed in, and spikes or spurs 714 may be provided so as to extend from, the outer surface 708 in a vicinity of the intermediate region 706 to facilitate both in-growth of tissue and secure engagement of tissue, also increasing positional and orientational stability in situ. While the holes 512 and 712 and the spurs 612 and 714 are shown in FIGS. 5-7 as appearing in the respective intermediate regions 506, 606, 706 of the respective positioning elements 500, 600, 700, such features may alternatively, and/or in addition, be positioned in one or both of the upper 502, 602, 702 and lower 504, 604, 704 arcuate regions thereof.

Figure 8:
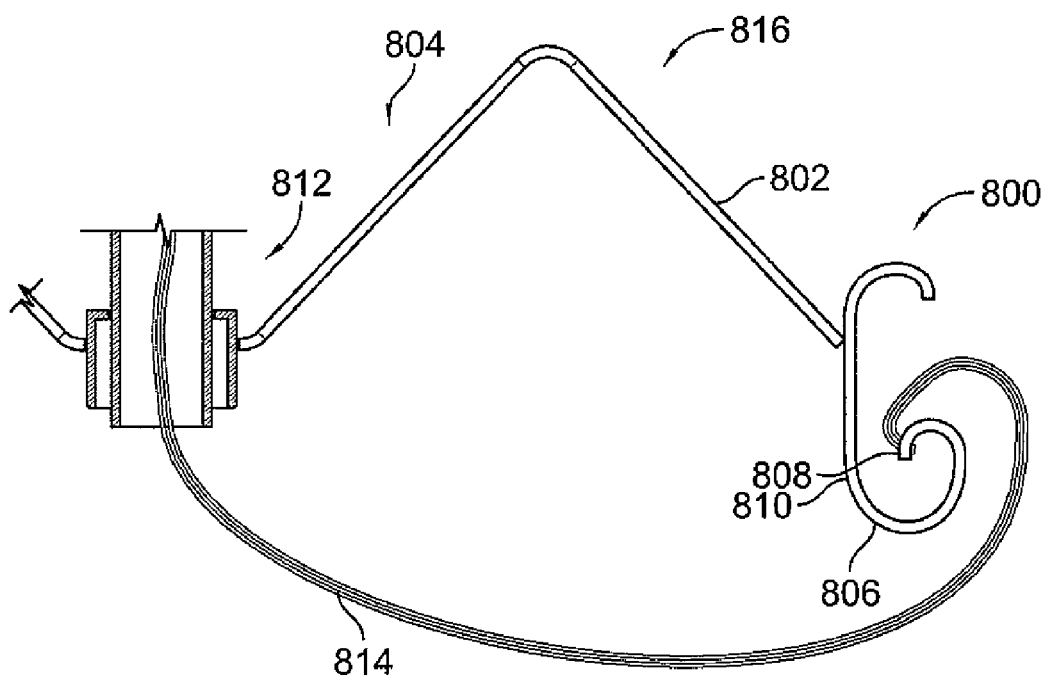
FIGS. 8, 9, 10, 11 and 12 are schematic side elevational and perspective views of variations of a prosthetic heart valve in accordance with the present disclosure.

Another variation of the positioning element 120 is embodied by the positioning element 800 of FIG. 8. A leg 802 of a resilient element 804 may support the positioning element 800, which may in turn include a lower arcuate region 806 having a tissue-engaging tip 808 that, in a retracted state of the lower arcuate region 806, may be coiled or 'rolled up' so as to extend inward toward an intermediate region 810 of the positioning element and/or downward toward itself A deployment structure 812 may include a cord 814 attached to the lower arcuate region 806 (e.g., near the tip 808 thereof) to uncoil the lower arcuate region 806 so as to permit the tip 808 to be redirected outward so as to be capable of engaging with a the cardiac tissue comprising a patient's heart wall (not shown). A surgeon/clinician may be permitted to pull outward on the cord 814 during positioning of the positioning element 800, and once the tip 808 has begun to engage the cardiac tissue, to release the cord 814, allowing an accumulated energy/spring force inherent in the lower arcuate region 806 (e.g., the same having a coil-spring configuration) to impinge with additional force upon the cardiac tissue. Multiple instances of the positioning element 800 may be provided in a valve prosthesis 816 (not otherwise shown) such that at least some balancing of reaction forces can be achieved, and an upper arcuate region 818 of the positioning element 800 may have a similar coiled configuration (not separately shown) to that of the lower arcuate region 806.

Figure 9:
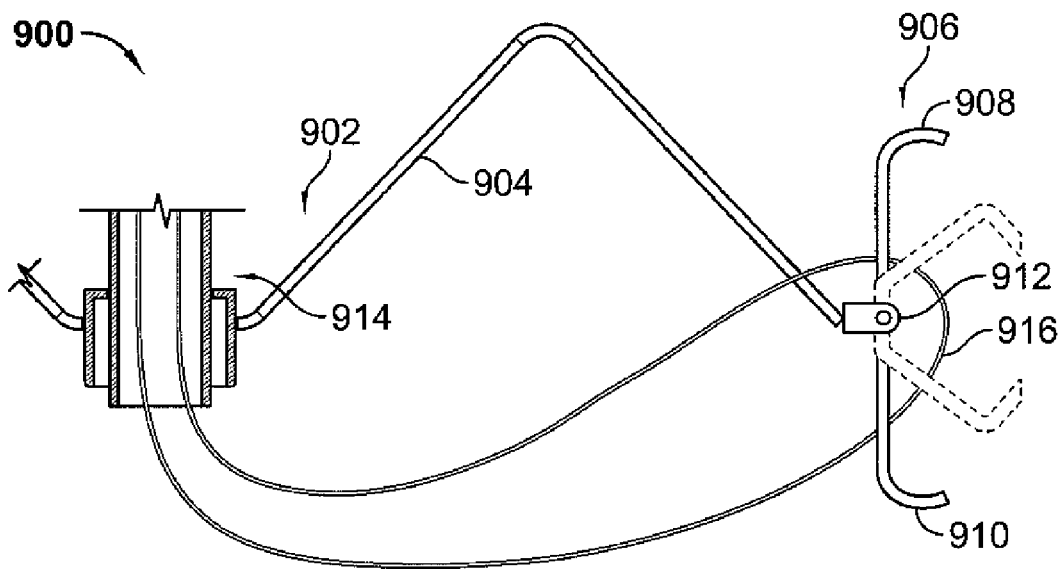

A modified version of the valve prosthesis 102 is embodied by the valve prosthesis 900, the latter being shown partially and schematically in FIG. 9. The valve prosthesis 900 may include a resilient element 902 having a leg 904 generally similar to the legs 116 associated with the above-described resilient element 112. The leg 904 may support a claw 906 having an upper jaw 908, a lower jaw 910, and a hinge 912 disposed between the upper and lower jaws 908, 910. The valve prosthesis 900 may further include a torsional spring (not shown) for biasing the upper and lower jaws 908, 910 of the claw 906 in favor of closure toward each other, and securely engaging the cardiac tissue of a patient's heart wall. A deployment structure 914 may include a cord 916 attached to the upper and lower jaws 908, 910. A surgeon/clinician may be permitted to pull outward on the cord 916 to hold the claw 906 open during positioning of the claw 906. Once the claw 906 has begun to engage the cardiac tissue (e.g., an annulus A as shown in FIG. 2), the surgeon/clinician may be permitted to release the cord 916, allowing the spring bias to act on the upper and lower jaws 908, 910 and thereby allowing the claw 906 to affix itself to the cardiac tissue. Multiple instances (not shown) of the claw 906 may be provided in the valve prosthesis 900.

Figure 10:
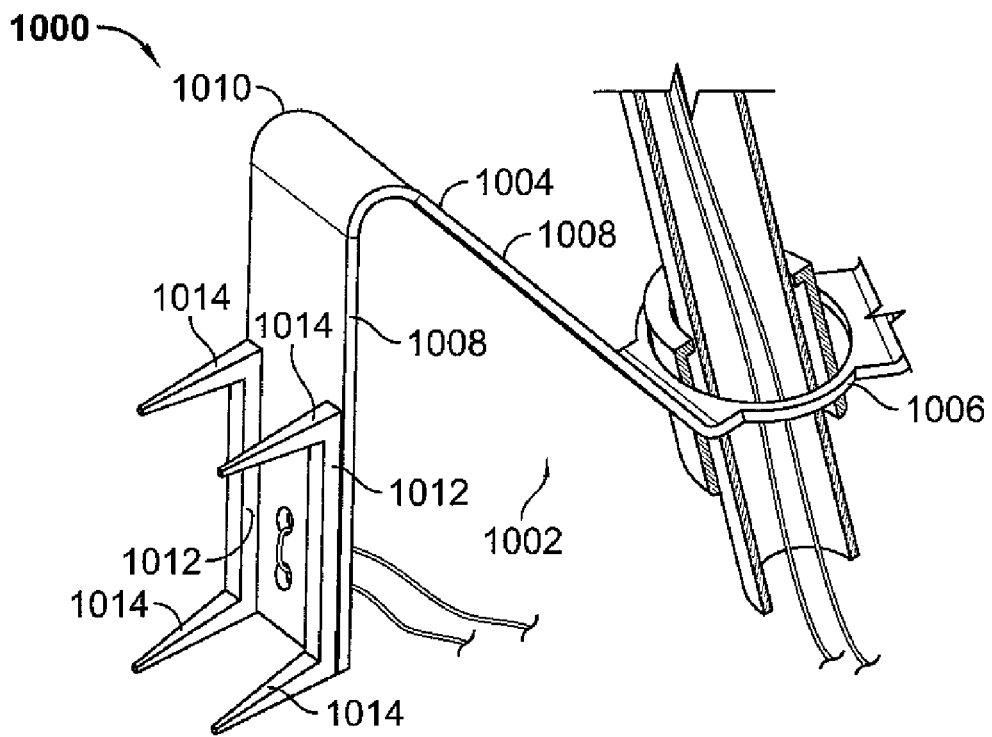
Figure 11:
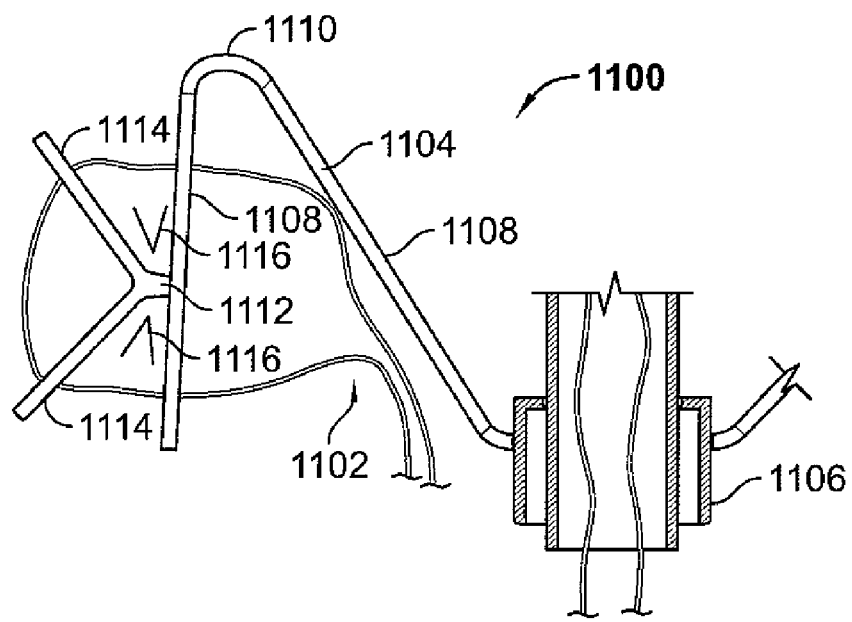
Figure 12:
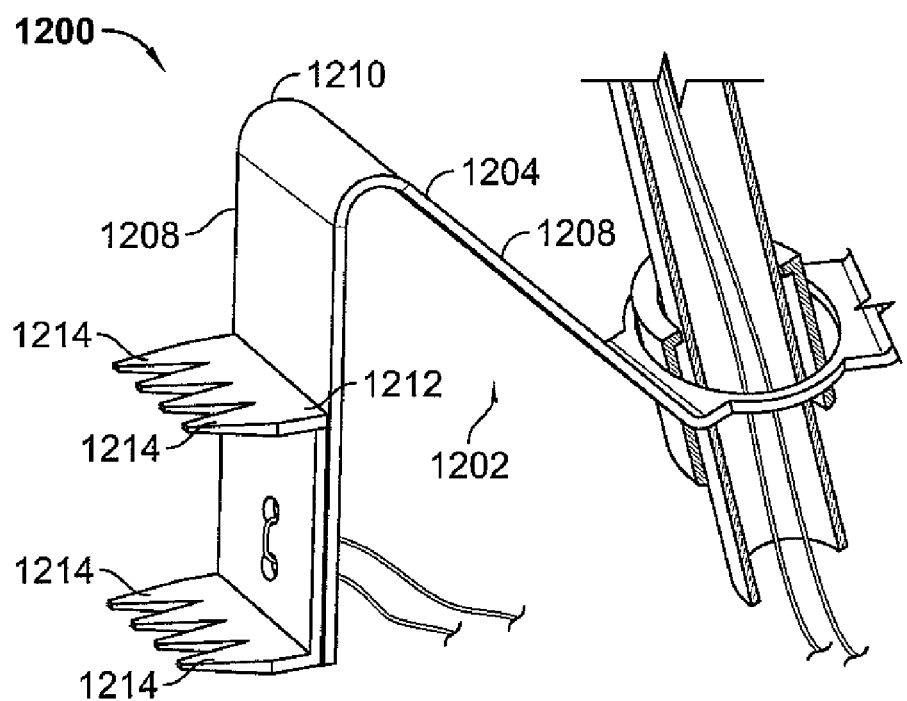

Respective alternative modified versions of the valve prosthesis 102 are further embodied by the valve prostheses 1000, 1100, and 1200, shown partially and schematically in FIGS. 10, 11 and 12, respectively. The valve prosthesis 1000 of FIG. 10 may include a resilient element 1002 having multiple instances of a leg 1004 extending from a hub 1006. The leg 1004 may itself be a spring, and may include at least two leaves 1008 joined at an arcuate or bend region 1010. The valve prosthesis 1000 may further include one or more engaging elements 1012, each of which may include a plurality of prongs 1014 for piercing and/or otherwise invasively engaging cardiac tissue as appropriate to secure the valve prosthesis 1000 in place relative to a diseased heart valve, and/or relative to an annulus associated therewith. The engaging element 1012 may be supported by one of the leaves 1008 of the leg 1004, and the valve prosthesis 1000 may include a plurality of sets of two engaging elements 1012 (e.g., having two prongs 1014 each) as shown in FIG. 10.

The valve prosthesis 1100 of FIG. 11 may include a resilient element 1102 having multiple instances of a leg 1104 extending from a hub 1106. The leg 1104 may itself be a spring, and may include at least two leaves 1108 joined at an arcuate or bend region 1110. The valve prosthesis 1100 may further include one or more engaging elements 1112, each of which may include two arms 1114 extending outward from a common point of connection in a V shape. The valve prosthesis 1100 may further include biasing springs (indicated schematically at reference numeral 1116) for urging the arms 1114 of the engaging elements 1112 together for purposes of closing the engaging element 1112 about an annulus associated with a patient's diseased heart valve. The engaging element 1112 may be supported by one of the leaves 1108 of the leg 1104, and the valve prosthesis 1100 may include a plurality of such engaging elements 1112.

The valve prosthesis 1200 of FIG. 12 may include a resilient element 1202 having multiple instances of a leg 1204 extending from a hub 1206. The leg 1204 may itself be a spring, and includes at least two leaves 1208 joined at an arcuate or bend region 1210. The valve prosthesis 1200 may further include one or more engaging elements 1212, each of which may include a plurality of teeth 1214 for engaging cardiac tissue as appropriate to secure the valve prosthesis 1200 relative to a diseased heart valve. The engaging element 1212 may be directly affixed to one of the leaves 1208 of the leg 1204 (e.g., the valve prosthesis 1200 may include a plurality of engaging elements 1212 having two rows of teeth 1214 each as shown in FIG. 12). In some embodiments (not separately shown), the engaging element 1212 may be hinged at a central location between the two rows of teeth 1214 such that the engaging element 1212 may be movable to at least some degree relative to the leg 1204. Accordingly, in at least some such embodiments, the engaging element 1212 may be utilized in the manner of a toothed claw otherwise structurally and functionally similar to the claw 906 described above with reference to FIG. 9.

Figure 13:
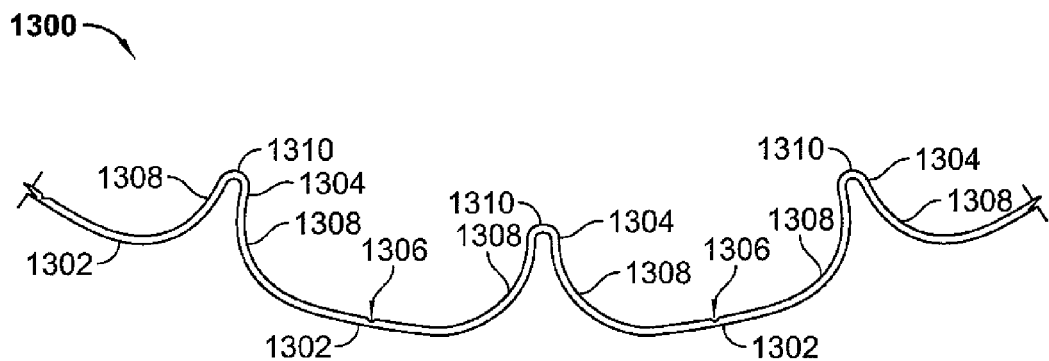
FIGS. 13 and 14 are respective side and views of a flexible ring according to the present disclosure.
Figure 14:
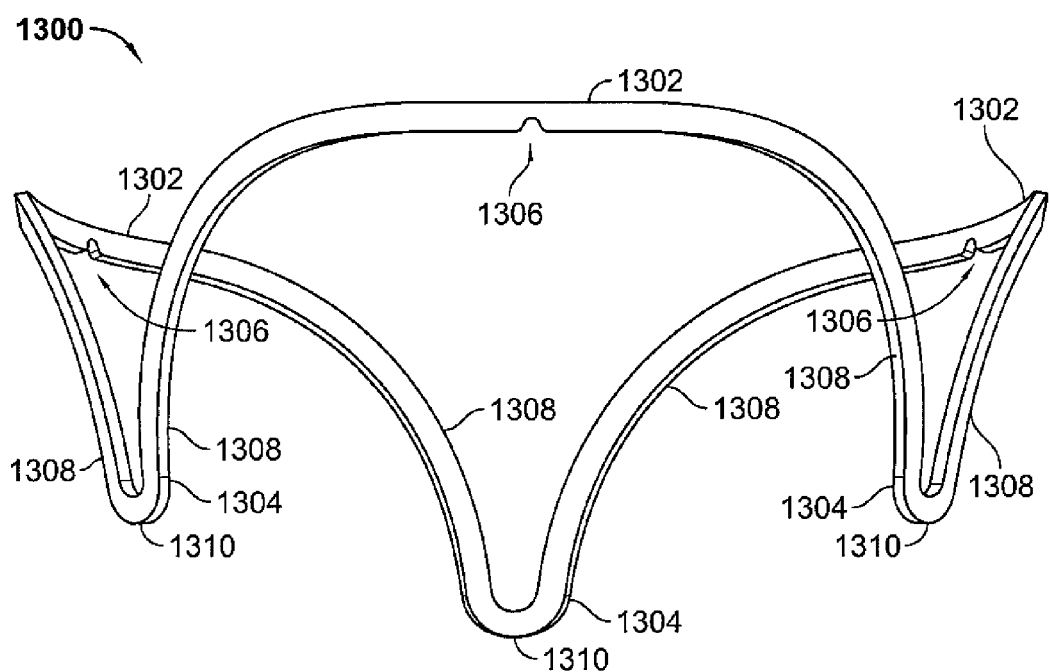

A variation of the above-discussed flexible ring 106 is embodied by a flexible ring 1300 illustrated in FIGS. 13 and 14. The flexible ring 1300 may be resilient such that it may tend (e.g., absent any substantial compressive forces) to expand outward to assume a three-dimensional shape (e.g., the three-dimensional shape shown FIG. 14), in which the flexible ring 1300 may have a not insubstantial vertical height, in addition to a characteristic lateral width or diameter. More particularly, the flexible ring 1300 may include multiple instances of a hoop segment 1302. The hoop segments 1302 may be contained within a common horizontal plane (e.g., upon the flexible ring 1300 being expanded out to its maximum width and height) wherein the hoop segments may be separated by and/or coupled via a corresponding number of instances of a coupling segment 1304 extending vertically relative to the common horizontal plane, constituting at least a portion of the height extent of the flexible ring 1300. Each hoop segment 1302 may further include a notch 1306 to facilitate secure coupling of one or more of a valve skirt similar to the above-described valve skirt 110, at least one leaflet membrane similar to the above-described leaflet membranes 108, and/or an associated annulus or cuff similar to that described above. For example, such coupling may be obtained via a knotted suture (not shown) at least partially lodged within the notch 1306 so as to restrict relative movement of the valve skirt, leaflet membrane, and/or cuff relative to and/or about a circumference of the flexible ring 1300. Each of the coupling segments 1304 may comprise a spring having two leaves 1308 joined at an arcuate or bend region 1310, whereby the flexible ring 1300 may be particularly amenable to being radially compressed and/or to assume a compact shape suitable for compressing a corresponding valve prosthesis (not separately shown) of which the flexible ring 1300 is a part, and/or passing such a prosthesis through a narrow-gauge catheter (not shown). More particularly, because the flexible ring 1300 may include intermittent breaks in its circumference in the plane of the hoop segments 1302 (e.g., associated with the coupling segments 1304), its geometry may further contribute to an elastic radial compressibility exhibited by the flexible ring 1300. The bend regions 1310 of the coupling segments 1304 may further serve as anchoring points functionally similar to the notches 1306. For example, such notches 1306 may be used as anchoring points for securing, and/or limiting a length extent of, commisure seams (not shown in FIGS. 13-14; see, e.g., corresponding structure illustrated and described below with reference to FIGS. 16-20) formed between corresponding leaflet membranes (not shown) of a heart valve prosthesis (not shown) incorporating the flexible ring 1300 in accordance with embodiments of the present disclosure.

Figure 15:
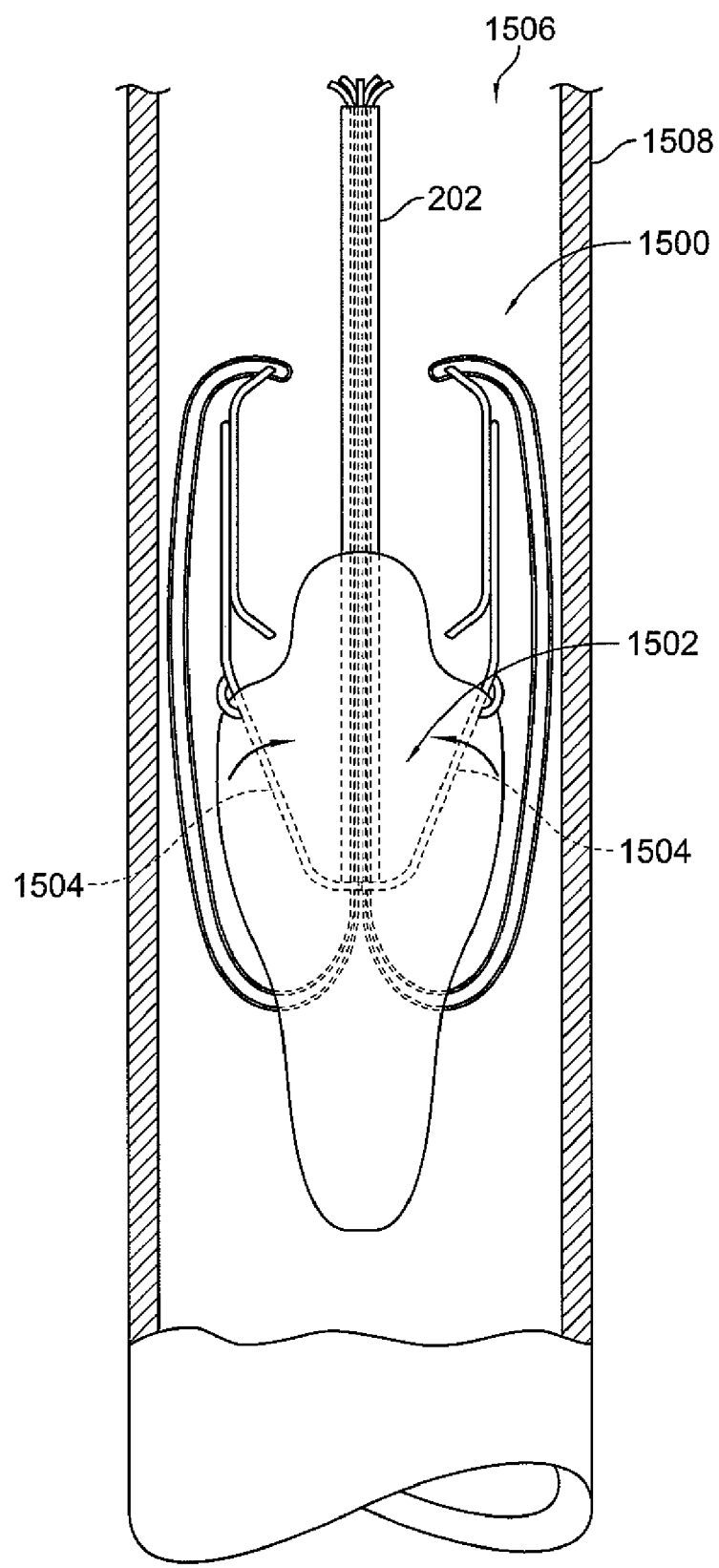
FIG. 15 is a schematic side view of an exemplary valve prosthesis contained within a delivery catheter in accordance with the present disclosure.

A variation of the valve prosthesis 102 in accordance with the present disclosure is embodied by a valve prosthesis 1500 illustrated in FIG. 15. The resilient element 1502 of the valve prosthesis 1500 may be structurally and functionally similar to the above-described resilient element 112. The legs 1504 of the resilient element 1502 may flex inwardly toward the delivery tube 202. For example, the legs 1504 may be adapted to flex inwardly toward the delivery tube 202 in a manner that facilitates an enhanced degree of radial compression of the valve prosthesis 1500. Such flexure of the legs 1504 may further permit the valve prosthesis 1500 to pass along a lumen 1506 of a catheter 1508 exhibiting a smaller internal diameter than would otherwise be the case.

A modified version of the valve prosthesis system 100 in accordance with the present disclosure is embodied by a valve prosthesis system 1600 illustrated in various stages of operation in FIGS. 16, 17, 18, 19, and 20. The valve prosthesis system 1600 may include a valve prosthesis 1602 that is a modified version of the valve prosthesis 102 including substantially all structural and functional features thereof, with at least some exceptions as discussed below. The valve prosthesis 1602 may include a resilient element 1604 having multiple instances of a leg 1606 extending radially outward from a hub 1608, and multiple instances of a leaflet membrane 1610. Commissures 1612 between the leaflet membranes 1610 may be partially closed, or at least limited in length via respective sutured seams 1614 formed between the leaflet membranes 1610. For example, the sutured seams 1614 may extend from a flexible ring 1616 of the valve prosthesis 1602, or from a location in spaced relation below the flexible ring 1616 (e.g., as in embodiments of the valve prosthesis (not specifically shown) in which each of the leaflet membranes 1610 forms a portion of a larger membrane structure of unitary construction), downward to a point coinciding with respective free ends or distal edges of the leaflet membranes 1610. The valve prosthesis system 1600 may further include a delivery structure 1618 that, in addition to having cables 1620 and a delivery tube 1622 structurally and functionally similar to corresponding aspects of the delivery structure 104, further includes a tower 1624 extending downward from the hub 1608.

Among other functions that may be provided thereby, the tower 1624 may at least participate in defining a central axis 1625 of the valve prosthesis system 1600, and may further introduce an axial (e.g., vertical or lengthwise) separation between an elevation (e.g., generally indicated at 1626 in FIG. 20) at which the legs 1606 meet the hub 1608 and an elevation (e.g., generally indicated at 1628 in FIG. 20) at which the cables 1620 extend, and/or are deployed, outward from the central axis 1625. As shown in FIGS. 16-20, such an arrangement may have the advantage of displacing and/or routing the cables 1620 generally away from an elevation (e.g., generally shown at 1630 in FIG. 18) occupied by the leaflet membranes 1610, and/or by the sutured seams 1614 disposed therebetween. More particularly, such an arrangement may advantageously reduce and/or eliminate a risk of the cables 1620 abrading or cutting the leaflet membranes 1610 and/or the sutures of the sutured seams 1614 during a process of deploying, adjusting a position of, and/or otherwise implanting the valve prosthesis 1602. Such a risk does not necessarily exist with respect to any particular embodiment of a heart valve prosthesis in accordance with the present embodiment. For example, embodiments in accordance with the present disclosure of the heart valve prosthesis 102 shown and described herein with reference to FIGS. 1, 2, 3A-3B, and 4A-4I exist in which such a risk is either remote, or for all practical purposes, non-existent. Nevertheless, it is contemplated that such a risk may exist with respect to at least some heart valve prosthesis embodiments in accordance with the present disclosure, including, for example, embodiments in which the particular dimensions of, or the particular materials specified for, the sutures of the sutured seams 1614, and/or the leaflet membranes 1610, are optimized for purposes of providing maximum functionality and/or durability in situ, but wherein such optimization unfortunately has the effect of leaving such components at increased risk of damage from frictional interaction with the cables 1620 during prosthesis implantation. In such circumstances, at least, the use of a tower 1624, or of another component structurally and/or functionally similar thereto, to introduce an appropriate axial separation between the cables 1620 and the leaflet membranes 1610, and/or between the cables 1620 and the sutured seams 1614, may provide a particular advantage.

Figure 20:
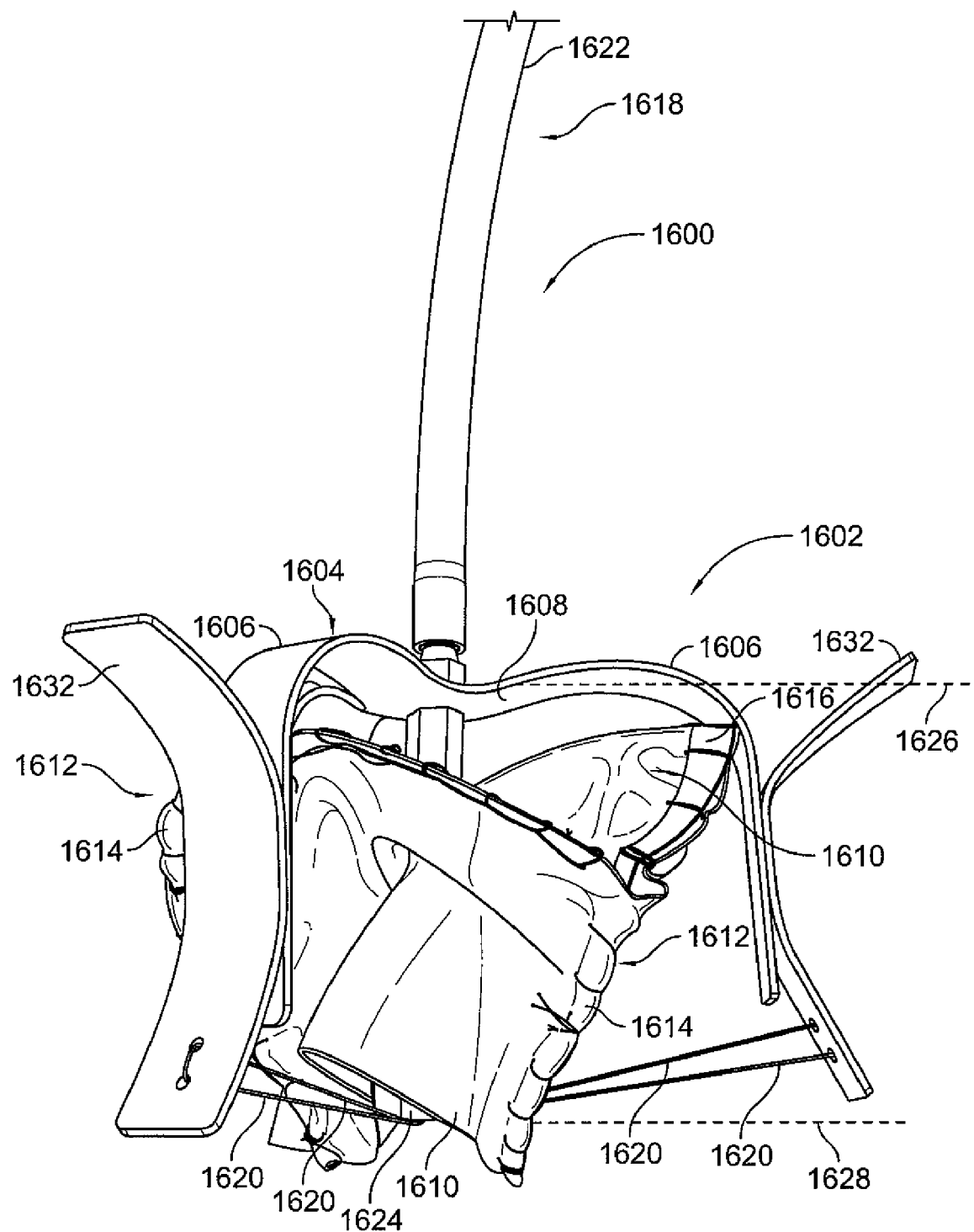

As is particularly evident in FIG. 20, such an arrangement may further permit additional energy and/or spring force to be built up within the resilient element 1604 by imparting significant flexure to the resilient element 1604 where the legs 1608 meet the hub 1606. For example, and as sequentially illustrated in FIGS. 16-20, a sufficient amount of flexure may be imparted thereby to the resilient element 1604 to cause the hub 1606 to be raised to an elevation substantially entirely above those of the respective positioning elements 1632 during a corresponding process of deployment from a catheter 1634, in which the positioning elements 1632 may be overturned or inverted relative to the flexible ring 1616 and the hub 1608 in preparation for placement of the valve prosthesis 1602 with respect to a patient's diseased heart valve. Such elevated placement of the hub 1608 relative to the positioning elements 1632 may further persist in the final in situ configuration of the valve prosthesis 1602 within the diseased heart valve (not specifically shown), such that an elevation of the hub 1608 may be and/or remain even with or above that of the corresponding annulus A (see FIG. 2 for comparison). Still further, in such circumstances, the legs 1608 may assume a final configuration relative to the hub 1606 such that: i) the legs 1608 either effectively no longer extend vertically upward from the hub 1608; or ii) an extent to which the legs 1608 continues to so extend upward from the hub 1606 is substantially reduced; and/or iii), the legs 1608 have substantially completely been overturned relative to the flexible ring 1616 so as to extend substantially completely downwardly from the hub 1608. Any one or all of these arrangements of the legs 1608 of the resilient element 1604 relative to the hub 1606 thereof and/or relative to the flexible ring 1616 may have the advantageous effect of reducing an occurrence of or an extent of eddies or turbulence in the flow of blood past or through the resilient element 1604. In such circumstances, a risk of undue tissue damage in the associated blood flow volume may be reduced. More particularly, to the extent such eddies and/or turbulence may be attenuated as described above, an extent and/or magnitude of a shear force characteristic of the flow of blood through the heart valve prosthesis 1602, and potentially associated with and/or causing such tissue damage, may be beneficially adjusted, limited, and/or reduced.

Figure 21:
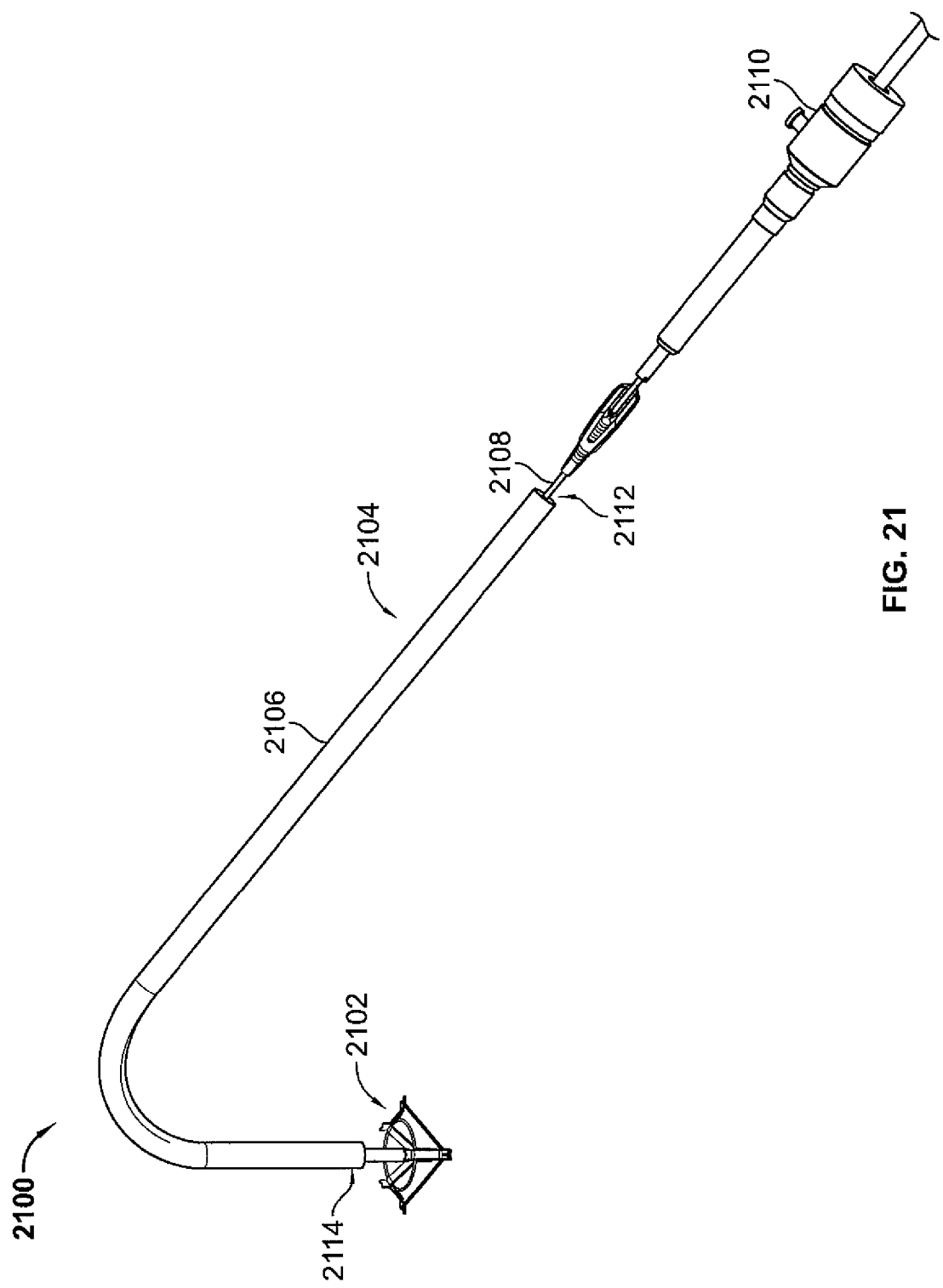
FIG. 21 is a schematic perspective view of a variation of a valve prosthesis system in accordance with the present disclosure.

A variation of the valve prosthesis system 100 is embodied by a valve prosthesis system 2100 illustrated in FIG. 21. The valve prosthesis system 2100 may include a valve prosthesis 2102 and a delivery structure 2104. The valve prosthesis 2102 may be a variation of the above-discussed valve prosthesis 102, and the delivery structure 2104 may be a variation of the above-discussed delivery structure 104. The delivery structure 2104 may include an outer catheter 2106, a guide wire 2108, and a tool 2110 for allowing a surgeon/clinician to move the valve prosthesis 2102 within and relative to the outer catheter 2106 along the guide wire 2108. For the sake of convenience, the valve prosthesis 2102 is shown twice in FIG. 21, once in a folded/compressed configuration (e.g., suitable for insertion into the outer catheter 2106 at a receiving end 2112 thereof), and once in an expanded configuration (e.g., after deployment from the outer catheter 2106 at a discharging end 2114 thereof).

Figure 22:
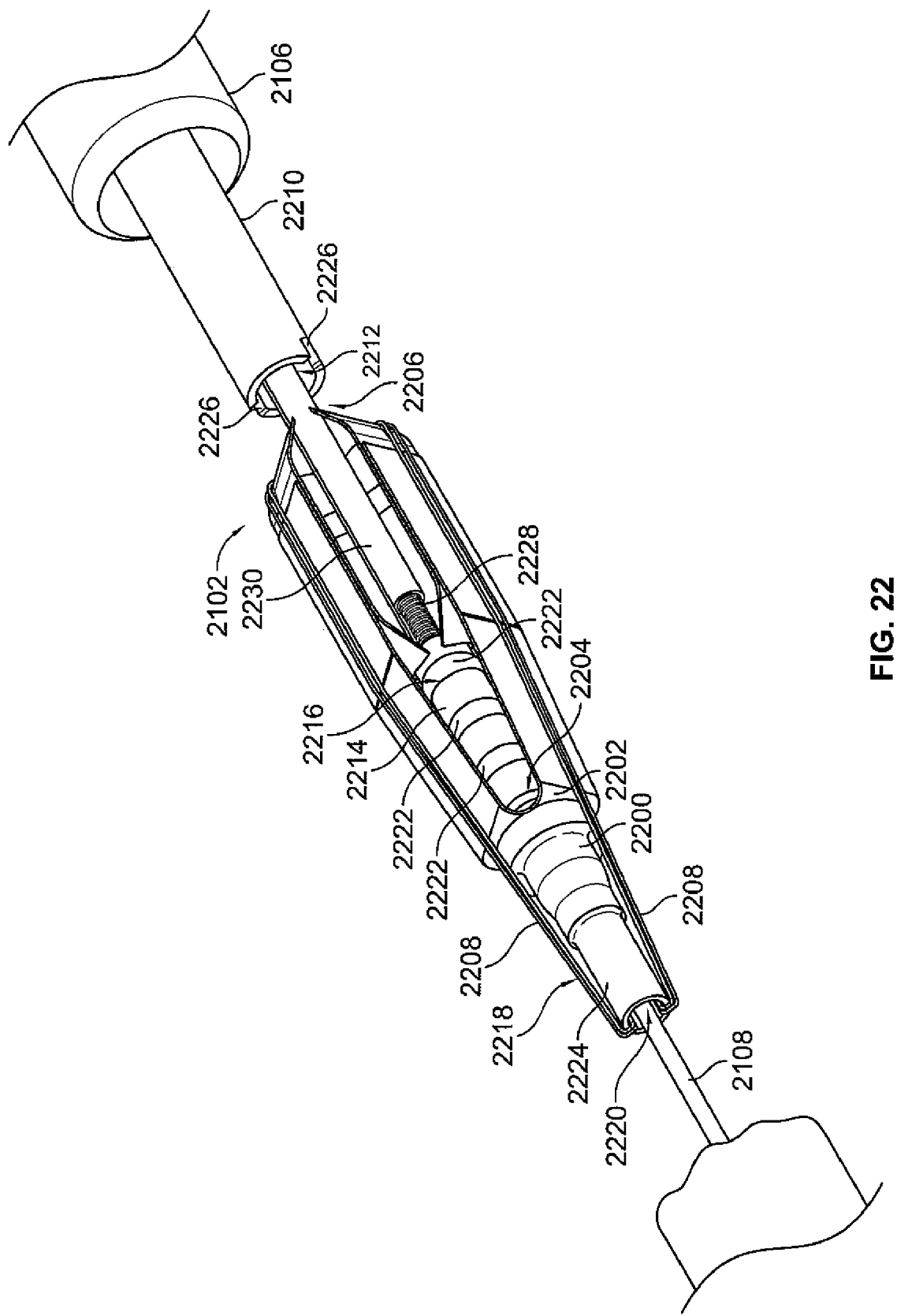
FIG. 22 is a schematic perspective view of a folded/compressed valve prosthesis of the valve prosthesis system of FIG. 21.

Referring now to FIG. 22, the valve prosthesis 2102 is shown in the folded/compressed configuration shown in FIG. 21 for movement within the outer catheter 2106 along the guide wire 2108. The valve prosthesis 2102 may include a sleeve 2200 extending downward to at least some extent from a hub 2202 of a resilient element 2204. The delivery structure 2104 may further include a cable guide tube 2206 for accommodating the guide wire 2108 and a set of deployment cables 2208, and a delivery tube 2210 including a central lumen 2212.

Figure 16:
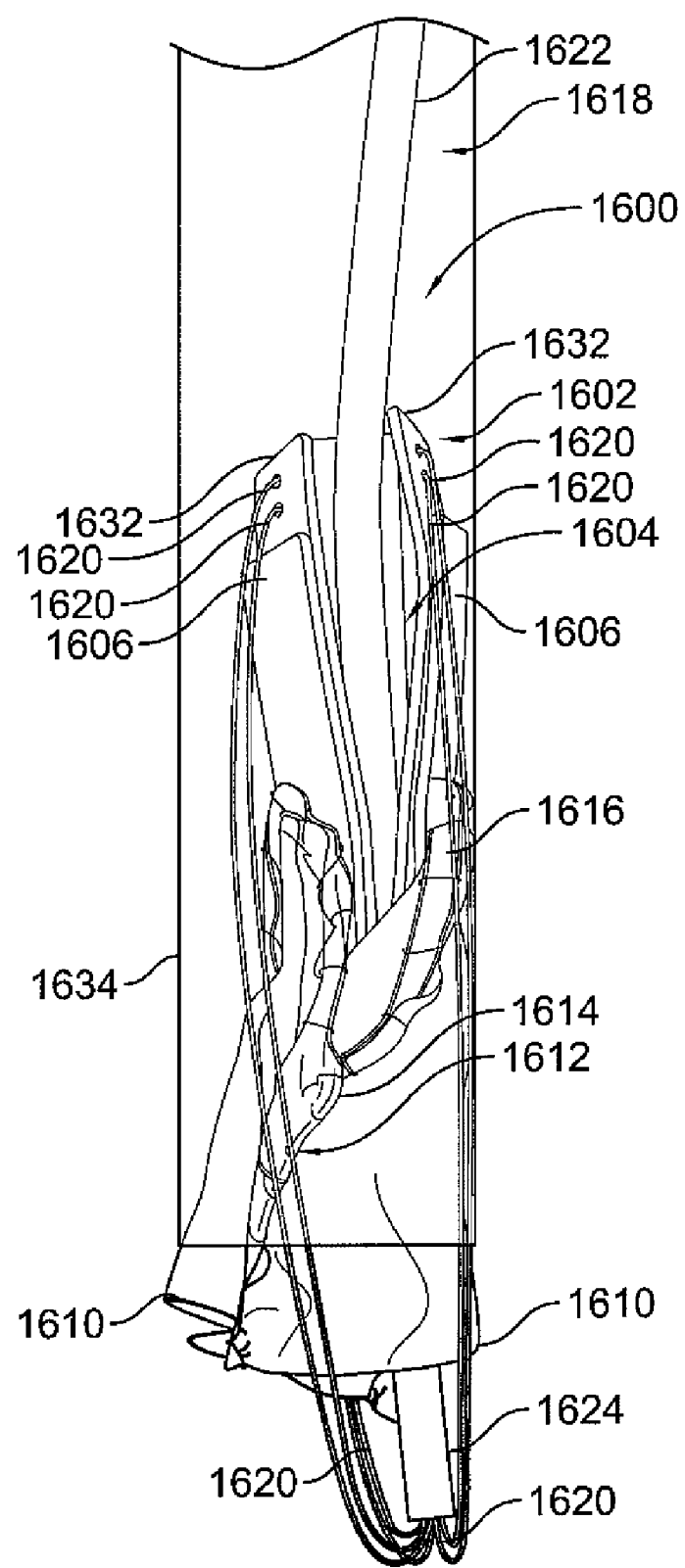
FIGS. 16, 17, 18, 19 and 20 are sequential side views of an exemplary valve prosthesis being outwardly deployed from within a delivery catheter in accordance with the present invention.
Figure 17:
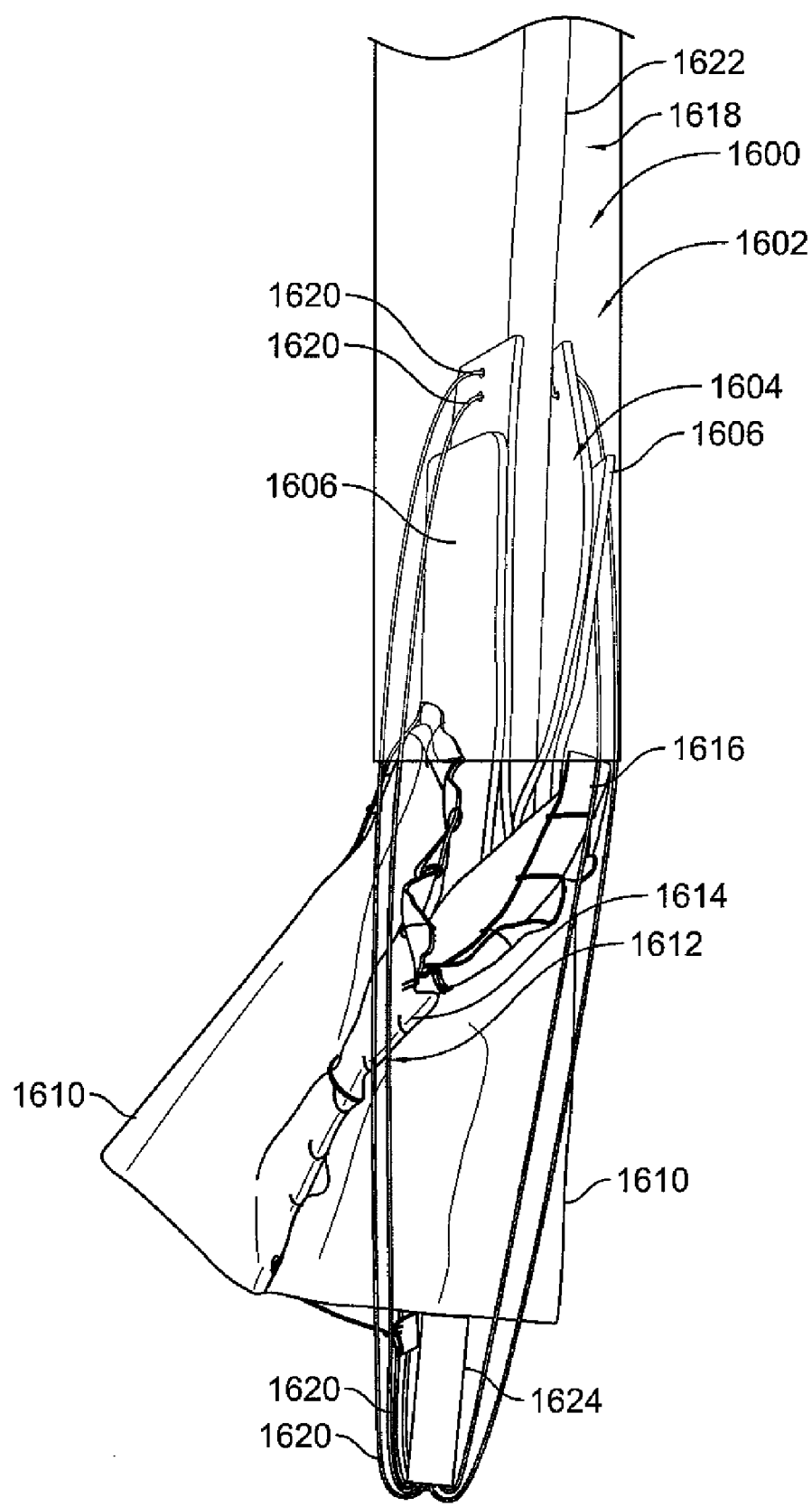
Figure 18:
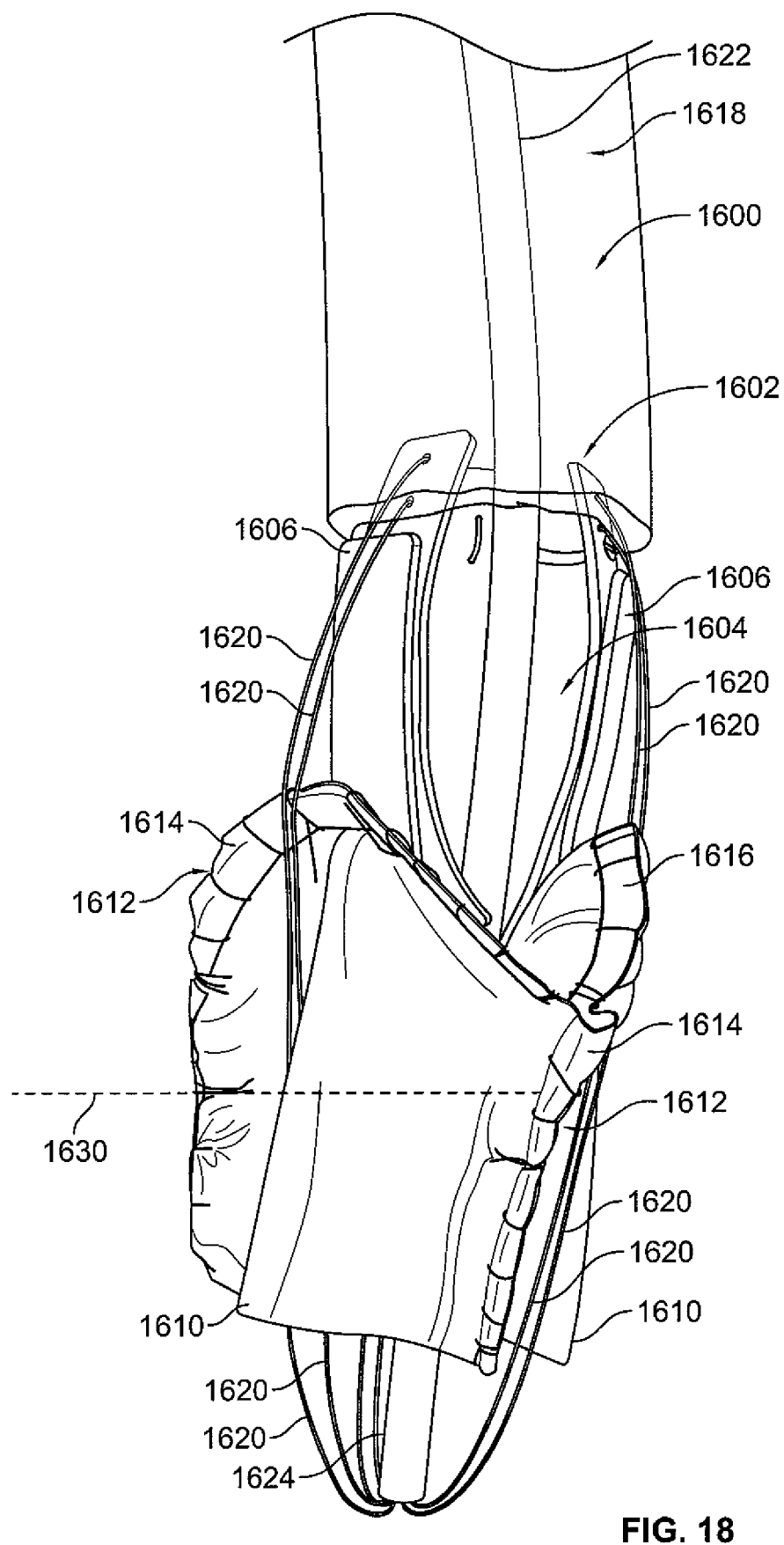
Figure 19:
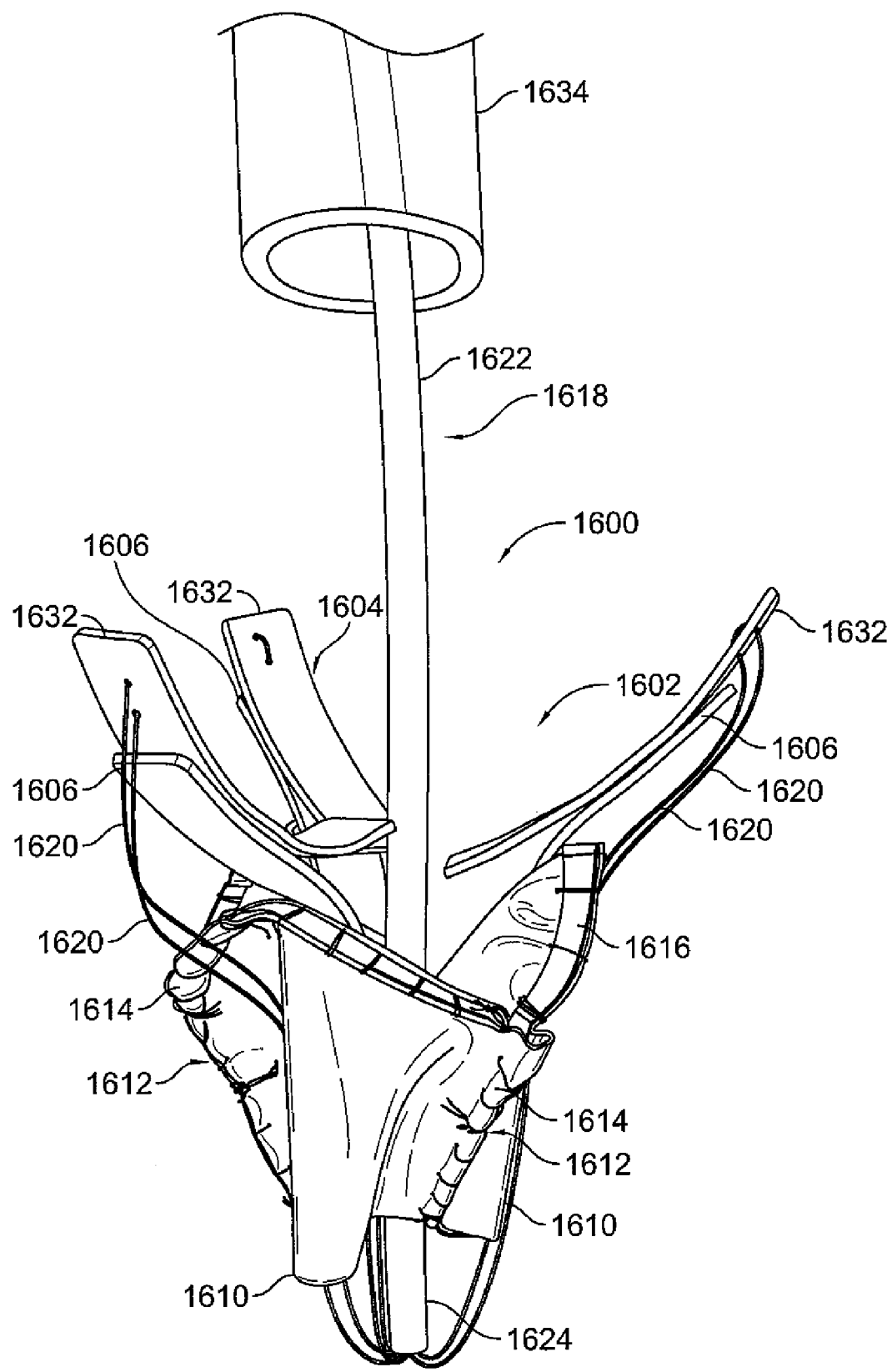

The delivery structure 2104 may still further include a fitting 2214. The fitting 2214 may extend entirely through the hub 2202 and the sleeve 2200 such that at least an upper portion 2216 of the fitting 2214 is disposed above the hub 2202, and at least a lower portion 2218 of the fitting 2214 is disposed below the sleeve 2200. The fitting 2214 may include a central lumen 2220 via which the guide wire 2108 and the deployment cables 2208 may pass through the fitting 2214 (and, thereby, through the hub 2202). The upper portion 2216 of the fitting 2214 may be sized and shaped (e.g., via external circumferential ribs 2222) for press-fit insertion within the central lumen 2212 of the delivery tube 2210, and/or to receive a corresponding end of the cable guide tube 2206 for press-fit termination thereof within the central lumen 2220. The lower portion 2218 of the fitting 2214 may form a tower 2224. The tower 2224 may be a variation of the above-described tower 1624 (FIG. 16).

The delivery tube 2210 and the fitting 2214 may be keyed to each other to prevent relative rotation therebetween. For example, an end of the delivery tube 2210 adjacent the hub 2202 may include one or more slots 2226, and the fitting 2214 may include one or more complementary radially-protruding tabs (not separately shown) to mate with the slots 2226 upon the fitting 2214 being press-fit within the central lumen 2212 of the delivery tube 2210. Other anti-rotation solutions and/or features are possible.

The cable guide tube 2200 may have multiple components, including an internal length of metal tubing 2228, and an external length of shroud-type tubing 2230. The internal length of metal tubing may be thin-walled and braided for stiffness and/or resistance to kinking. The external length of shroud-type tubing may be sized, shaped and configured to facilitate formation of a press-fit termination within the central lumen 2220 of the fitting 2214.

Figure 23:
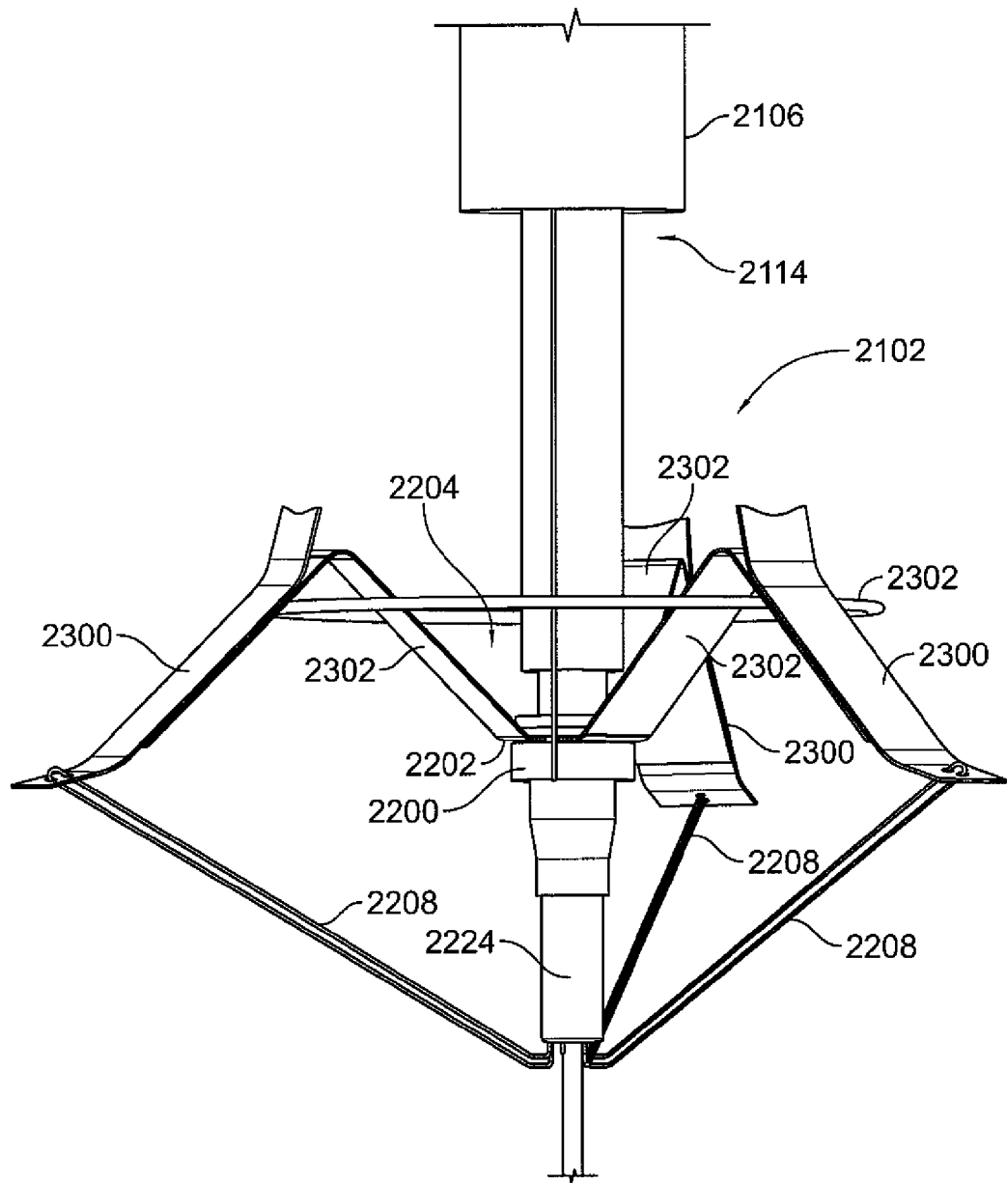
FIG. 23 is a side view of a deployed valve prosthesis of the valve prosthesis system of FIG. 21.

In FIG. 23, the valve prosthesis 2102 is shown after having emerged from the discharging end 2114 of the outer catheter 2106, and after the surgeon/clinician has permitted the positioning elements 2300 to overturn relative to a flexible ring 2302 and/or relative to the hub 2202 (e.g., via an internally-generated spring force), and/or has utilized the tool 2110 (FIG. 21) and the cables 2208 to cause or assist in causing the positioning elements 2300 to overturn relative thereto. As described above with reference to the valve prosthesis 1602 of FIGS. 16-20, the tower 2224 may beneficially extend a point of radial distribution of the cables 2208 axially downward to an elevation below that at which a plurality of legs 2302 of the resilient element 2204 meet the hub 2202 thereof. In embodiments, the sleeve 2200, which may be funnel-shaped and swaged to the hub 2202, may facilitate this function by providing lateral support to the cable deployment tower 2224.

Figure 24:
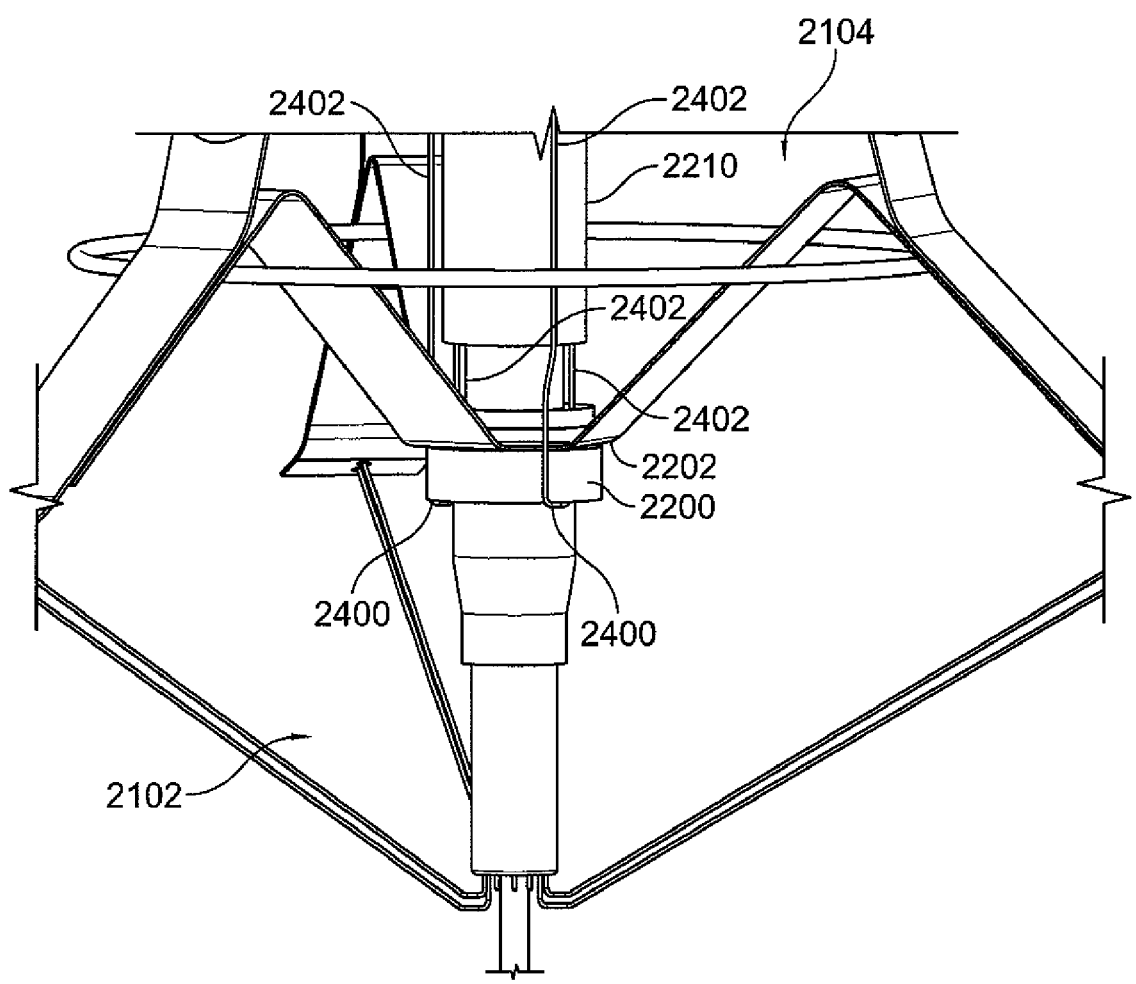
FIG. 24 is a cutaway detail view of the deployed valve prosthesis of FIG. 23.

Referring now to FIG. 24, the delivery structure 2104 may further include one or more additional cables 2400. The cables 2400 may function to axially secure the delivery tube 2210 to the hub 2202, and/or to the sleeve 2200, until such time as the valve prosthesis 2102 is determined to be properly positioned and oriented relative to the patient's diseased heart valve. More particularly, each instance of a cable 2400 may form a corresponding loop around a portion of the sleeve 2200, and include lengths 2402 passing upward therefrom. For example, one such length 2402 may pass through the central lumen 2212 (FIG. 22) of the delivery tube 2210, and the other such length 2402 may pass upward within a space (not separately shown) between the delivery tube 2210 and the outer catheter 2106 (FIG. 21). Such cables 2400 may further be withdrawn from the delivery structure 2104 when no longer needed (e.g., upon the valve prosthesis 2102 being determined to be properly positioned and oriented relative to the patient's diseased heart valve). The delivery tube 2210 and the hub 2202 may now no longer axially secured to each other, and the fitting 2214 and the delivery tube 2210 may remain axially secured to each other. In such circumstances, the surgeon/clinician may elect to withdraw the delivery tube 2210 from the patient's body via the outer catheter 2106 (FIG. 21) by pulling upward and outward on the delivery tube 2210. As the tower 2224 may be part of the fitting 2214, the surgeon/clinician may, by pulling upward on the delivery tube 2210, further withdraw the tower 2224 upward from and out of the hub 2202. The sleeve 2200 may travel outward of the patient's body along with the delivery tube 2210.

Figure 25:
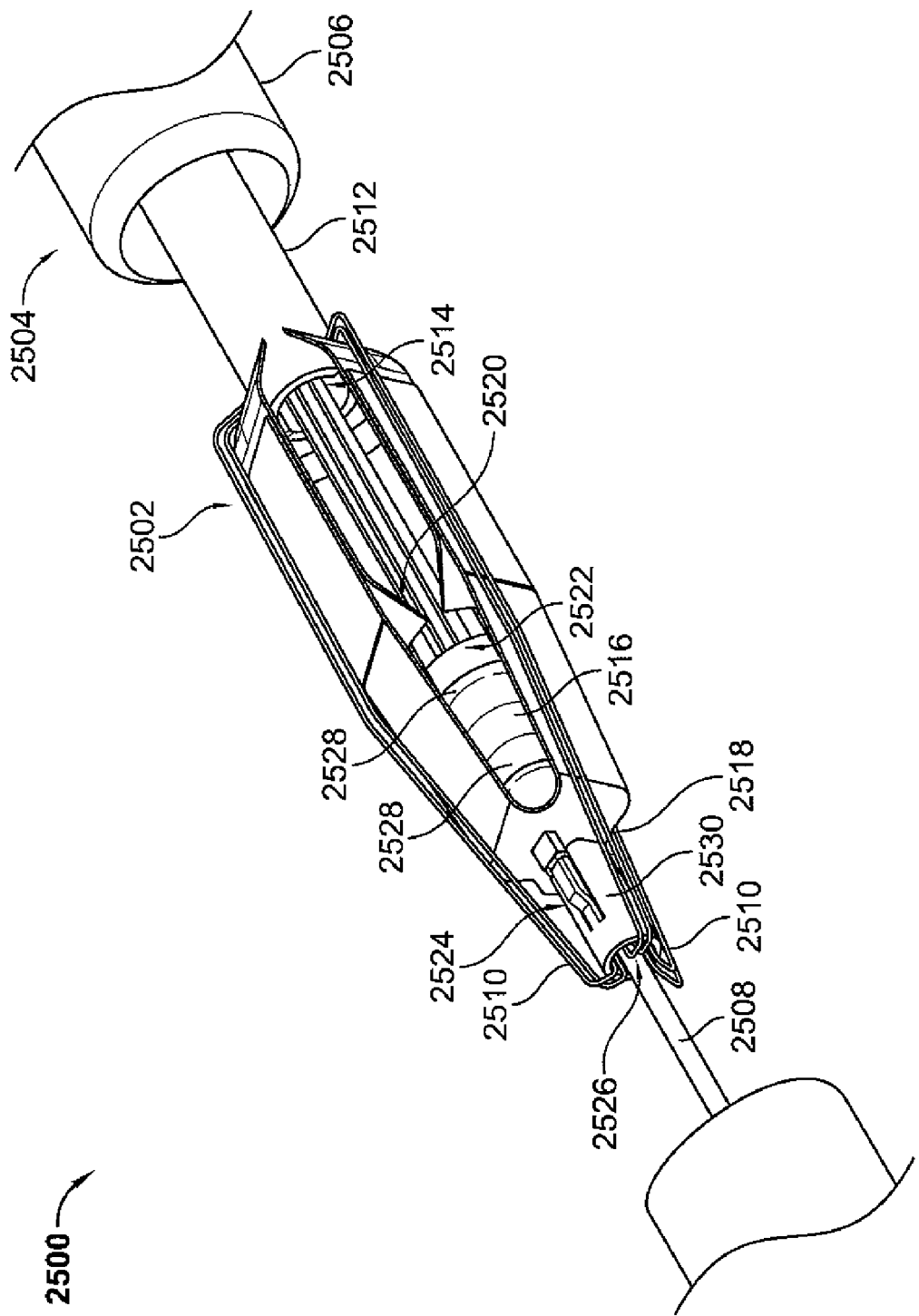
FIG. 25 is a schematic perspective view of a folded/compressed valve prosthesis in accordance with the present disclosure.

Another variation of the valve prosthesis system 100 is embodied by a valve prosthesis system 2500 illustrated in FIG. 25. The valve prosthesis system 2500 may include a valve prosthesis 2502 and a delivery structure 2504. The valve prosthesis 2502 may be a variation of the above-discussed valve prosthesis 102, and the delivery structure 2504 may be a variation of the above-discussed delivery structure 104. The delivery structure 2504 may include an outer catheter 2506 and a guide wire 2508 for allowing a surgeon/clinician to move the valve prosthesis 2502 within and relative to the outer catheter 2506 via an appropriate tool (e.g., tool 2110 of FIG. 1) along the guide wire 2508. The valve prosthesis 2502 is shown in a folded/compressed configuration for movement within the outer catheter 2506 along the guide wire 2508.

The delivery structure 2504 may further include a set of deployment cables 2510, a delivery tube 2512 including a central lumen 2514, and a fitting 2516. The fitting 2516 may extend entirely through a hub 2518 of a resilient element 2520 of the valve prosthesis 2502 such that at least an upper portion 2522 of the fitting 2516 is disposed above the hub 2518, and at least a lower portion 2524 of the fitting 2516 is disposed below the hub 2518. The fitting 2516 may include a central lumen 2526 via which the guide wire 2508 and the deployment cables 2510 may pass through the fitting 2516 (and, thereby, through the hub 2518). The upper portion 2522 of the fitting 2516 may be sized and shaped (e.g., via external circumferential ribs 2528) for press-fit insertion within the central lumen 2514 of the delivery tube 2512. The lower portion 2524 of the fitting 2516 may form a tower 2530. The tower 2530 may be a variation of the above-described tower 1624 (FIG. 16).

Figure 26:
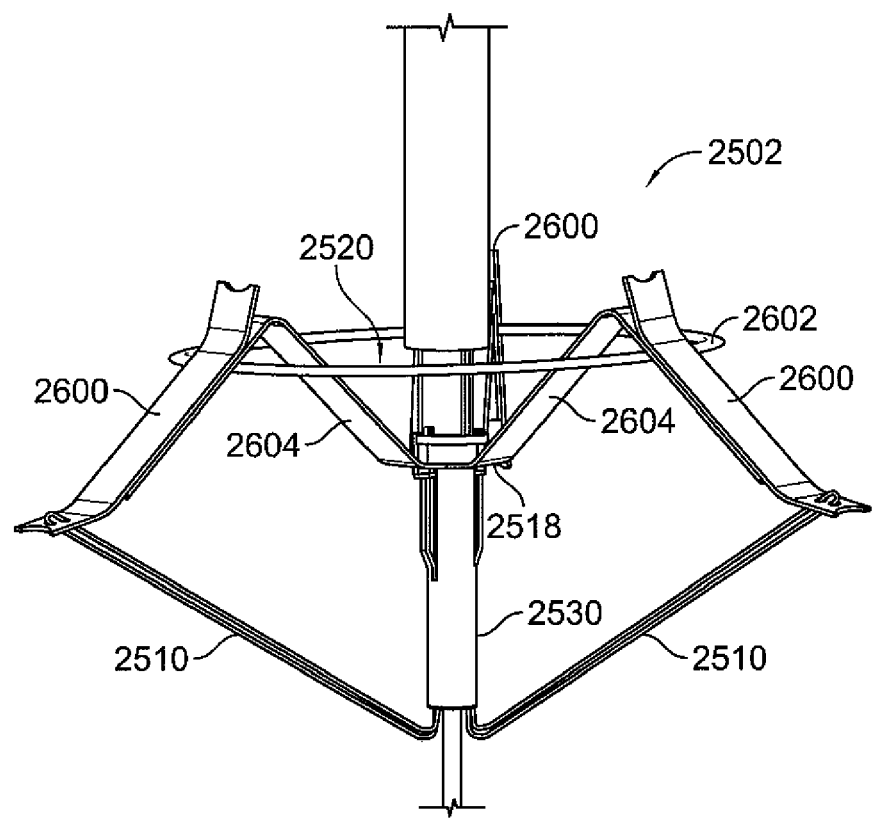
FIG. 26 is a side view of a deployed valve prosthesis of the valve prosthesis system of FIG. 25.

In FIG. 26, the valve prosthesis 2502 is shown after having emerged from the outer catheter 2506 (FIG. 22), and after the surgeon/clinician has permitted the positioning elements 2600 to overturn relative to a flexible ring 2602 and/or relative to the hub 2518 (e.g., via an internally-generated spring force), and/or has utilized an appropriate tool (e.g., tool 2110 of FIG. 21) and the cables 2510 to cause the positioning elements 2600 to overturn or invert relative thereto. As described above with reference to the valve prosthesis 1602 of FIGS. 16-20, the tower 2530 may beneficially extend a point of radial distribution of the cables 2510 axially downward to an elevation below that at which a plurality of legs 2604 of the resilient element 2520 meet the hub 2518 thereof.

Figure 27:
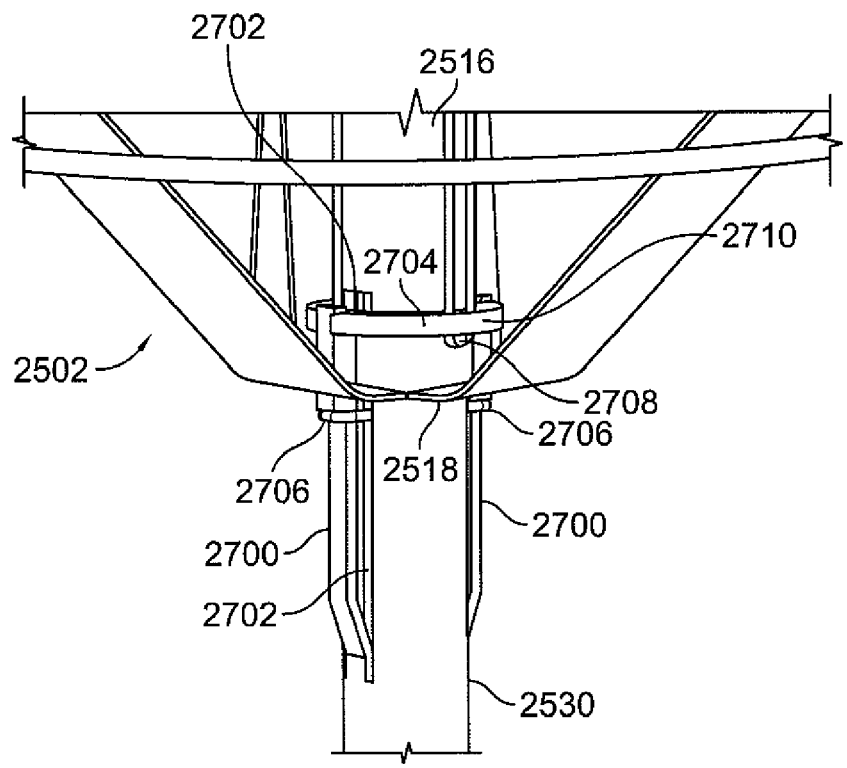
FIG. 27 is a cutaway detail view of the deployed valve prosthesis of FIG. 26.

Referring now to FIG. 27, the fitting 2516 may further includes multiple instances of an outwardly-biased, inwardly deflectable finger 2700 extending from a point on the cable deployment tower 2530 below the hub 2518, through a corresponding cutout in the hub 2518, and upward to a point on the fitting 2516 above the hub 2518. When each such finger 2700 is in its outwardly biased position, corresponding interlocking features (not separately shown) formed in the hub 2518 and the fingers 2700 may cooperate to secure the valve prosthesis 2502 axially relative to the fitting 2516. Each such finger 2700 may be further deflectable radially inwardly into an accommodating cavity 2702 formed in the fitting 2516. The delivery structure 2504 may further include a collar 2704 that may be disposed around the fitting 2516 between each such finger 2700 and its corresponding cavity 2702, such that whenever the collar 2704 is so positioned, the finger 2700 may be prevented from being deflected into its corresponding cavity 2702. The delivery structure 2504 may still further include one or more cables 2706 forming a corresponding loop around each such finger 2700 so as to be useable to pull or retract each such finger 2700 into its corresponding cavity 2702 in the absence of the collar 2704. The delivery structure 2504 may yet further include one or more cables 2708 forming corresponding loops around a flange 2710 of the collar 2704 so as to be useable to pull the collar 2704 upward and away from the fingers 2700 such that the collar 2704 ceases to block inward deflection of the fingers 2700. Accordingly, upon the valve prosthesis 2502 being determined to be properly positioned and oriented relative to the patient's diseased heart valve, a surgeon/clinician may pull or otherwise manipulate the cables 2708 to displace the collar 2704 upward and away from the fingers 2700, and pull or otherwise manipulate the cables 2706 to deflect the fingers 2700 inward toward the cavities 2702, and out of engagement with the hub 2518. The hub 2518 and the fitting 2516 may now no longer being axially secured relative to each other, and the fitting 2516 and the delivery tube 2512 (FIG. 25) may remain axially secured relative to each other. In such circumstances, the surgeon/clinician may elect to withdraw each of the fitting 2516 and the delivery tube 2512 from the patient's body via the outer catheter 2506 by pulling upward on the delivery tube 2512. As the tower 2530 may be part of the fitting 2516, the surgeon/clinician may, by pulling upward on the delivery tube 2512, withdraw the tower 2530 upward from and outward of the hub 2518.

Figure 28:
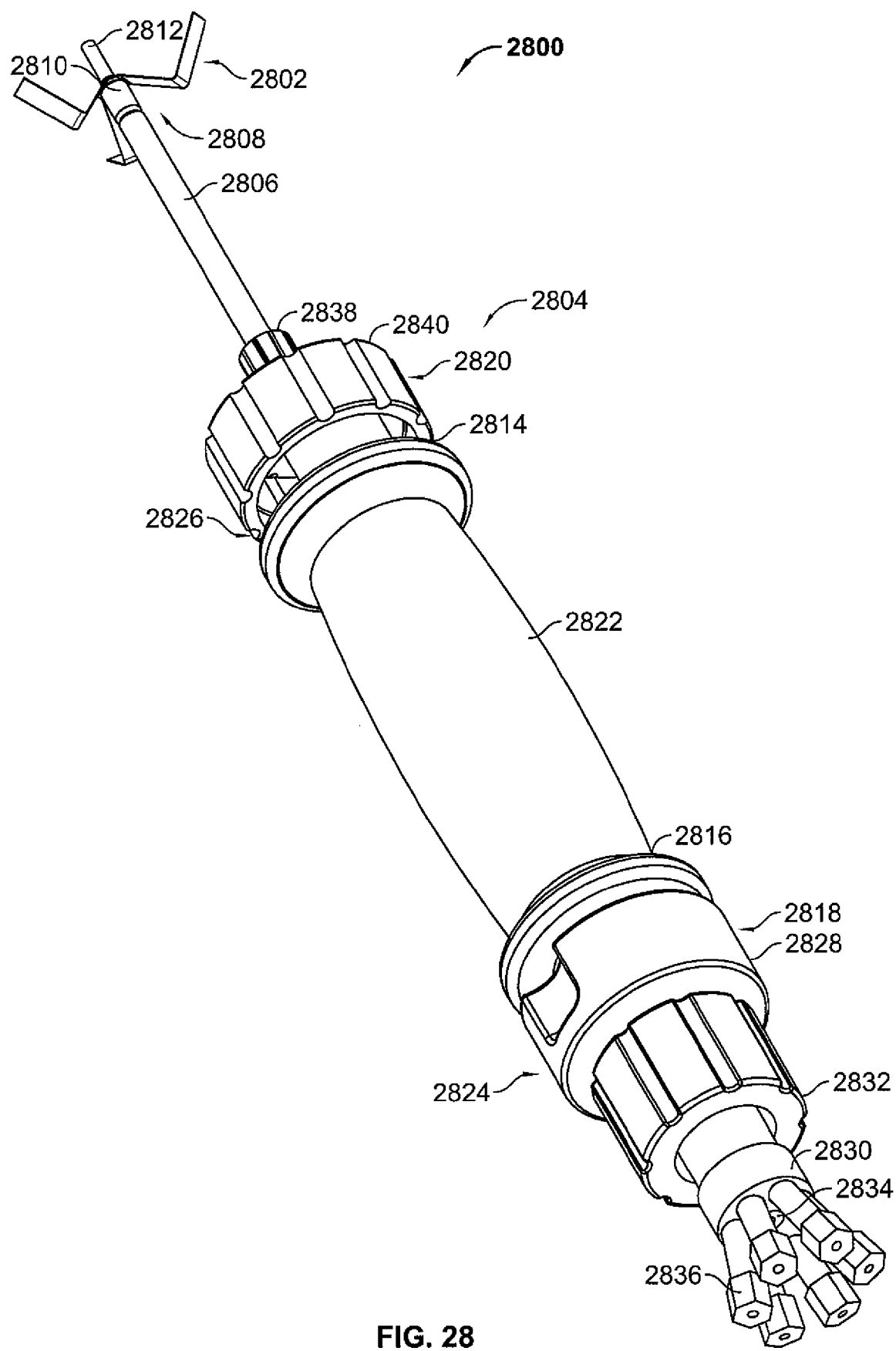
FIG. 28 is a schematic perspective view of a variation of a valve prosthesis system in accordance with the present invention.
Figure 34:
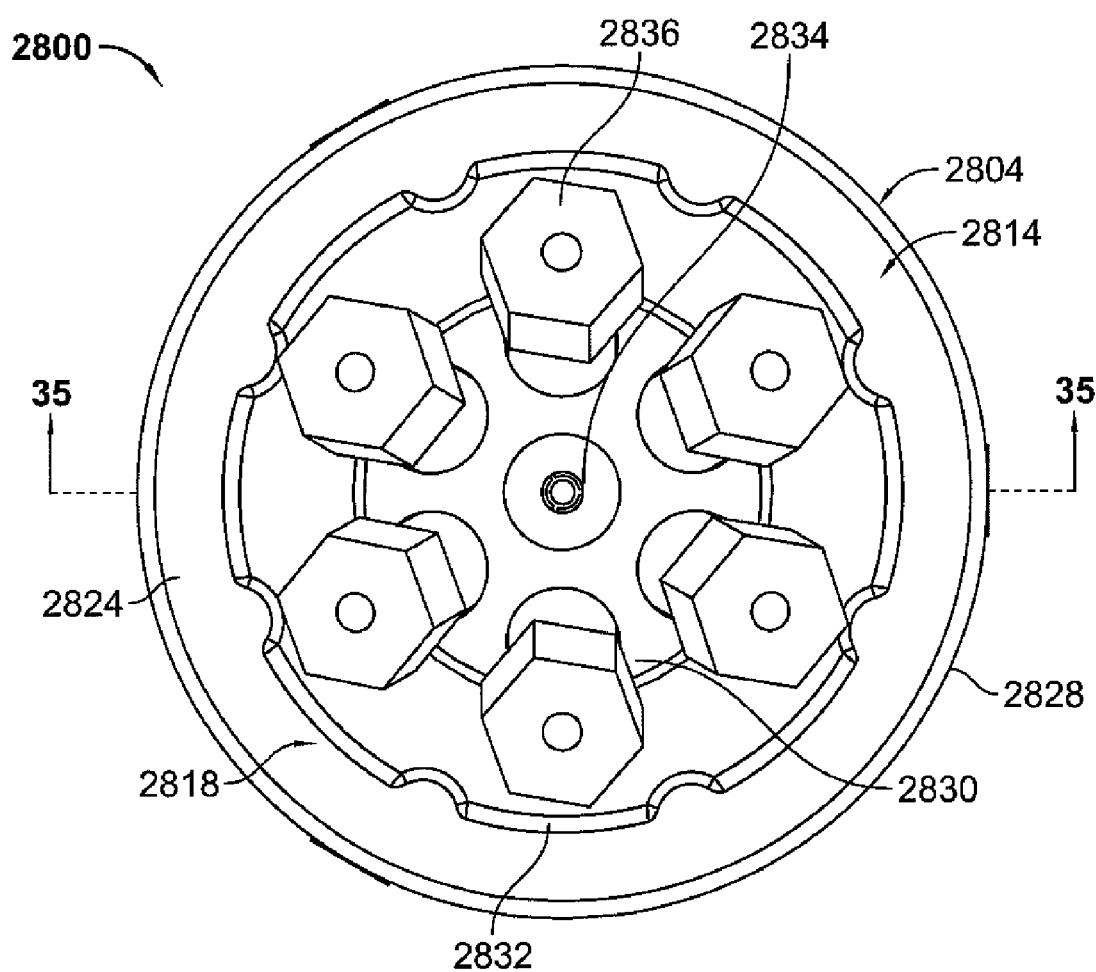
FIG. 34 is an end view of the valve prosthesis system of FIG. 28.

Still another variation of the valve prosthesis system 100 is embodied by a valve prosthesis system 2800 illustrated in FIGS. 28 and 34. The valve prosthesis system 2800 may include a valve prosthesis 2802 and a delivery structure 2804. The valve prosthesis 2802 may be a variation of the above-discussed valve prosthesis 102, and the delivery structure 2804 may be a variation of the above-discussed delivery structure 104.

The delivery structure 2804 may include a release tube 2806 having a distal end 2808 adjacent the valve prosthesis 2802, a locking sleeve 2810 positioned adjacent the valve prosthesis 2802 and coupled to the release tube 2806 at the distal end 2808 thereof, and a tower 2812 extending through and beyond the valve prosthesis 2802. The tower 2818 may be a variation of the above-discussed tower 1624.

The delivery structure 2804 may further include a tool 2814. The tool 2814 may be configured to permit and/or facilitate a surgeon/clinician, among other functions described in more detail hereinafter, to move the valve prosthesis 2802 within and relative to an outer catheter (not shown) along a guide wire (not shown), to deliver and/or deploy the valve prosthesis 2802 adjacent a patient's diseased heart valve, to position the deployed valve prosthesis 2802 relative to such heart valve before and during a prosthesis implantation procedure, and/or to cause the valve prosthesis 2802 to be released after deployment and positioning thereof in situ., allowing the valve prosthesis 2802 to remain in place and the delivery structure 2804 to be entirely withdrawn from the patient's body.

The tool 2814 may include a body 2816 having a proximal end 2818 directed away from the patient and a distal end 2820 directed toward the patient, a gripping handle 2822 disposed between the proximal end 2818 and the distal end 2820, a prosthesis manipulation mechanism 2824 mounted with respect to the body 2816 at the proximal end 2818 thereof, and a prosthesis release mechanism 2826 mounted with respect to the body 2816 at the distal end 2820 thereof. The prosthesis deployment mechanism 2824 may include an actuation arm 2828 movably mounted the body 2816, a cable mount 2830, and an attachment fitting 2832 for attaching the cable mount 2830 to the actuation arm 2828 for movement therewith relative to the body 2816. The cable mount 2830 may include a port 2834 for receiving and/or discharging a guide wire (not shown), and multiple instances of an attachment fitting 2836 for attaching a respective cable (not shown) to the cable mount 2830 for movement therewith relative to the body 2816. The prosthesis release mechanism 2826 may include an attachment fitting 2838 for attaching the release tube 2806 to the tool 2814, and an actuation wheel 2840 movably mounted to the body 2816 for moving the release tube 2806 and the locking sleeve 2810 relative to the body 2816, and/or relative to the valve prosthesis 2802.

Figure 29:
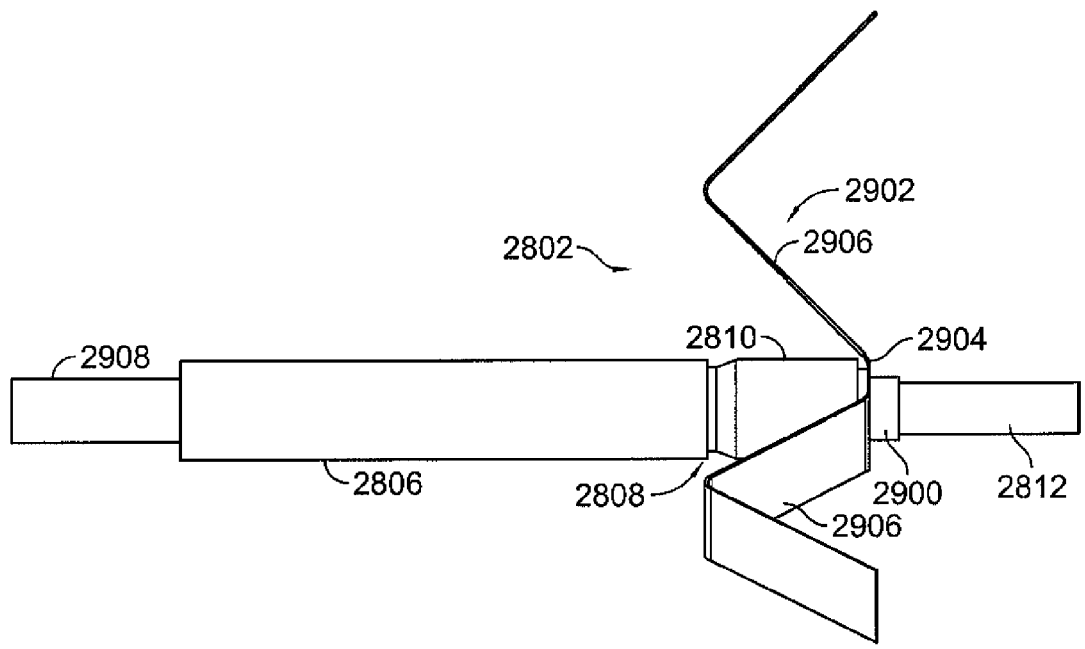
FIG. 29 is a side elevational view of a valve prosthesis of the valve prosthesis system of FIG. 28.
Figure 30:
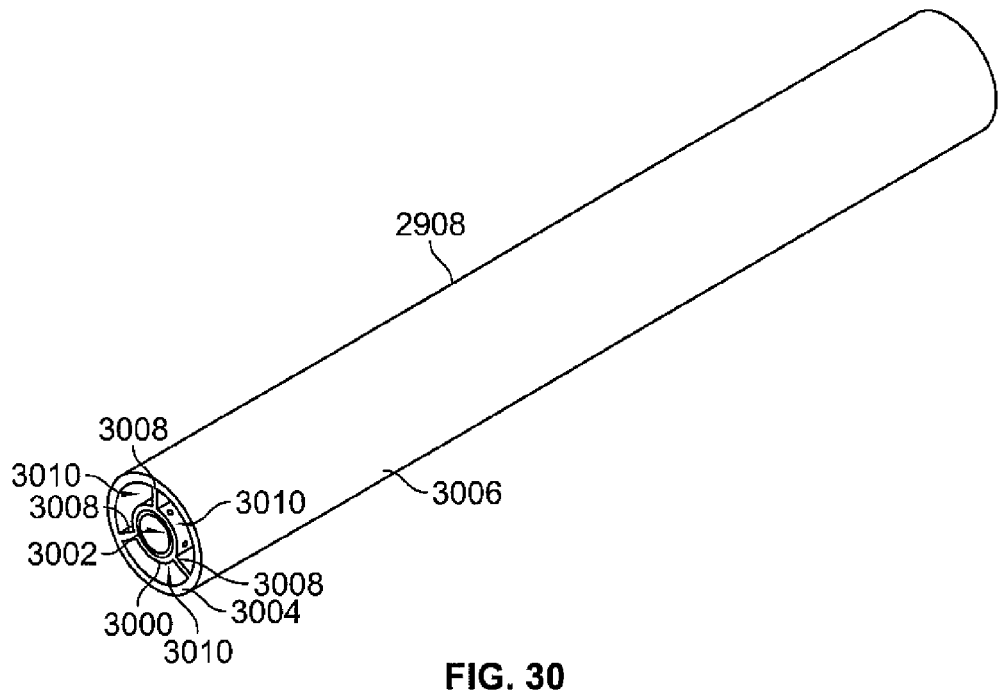
FIG. 30 is a perspective view of a cable guide tube of the valve prosthesis system of FIG. 28.
Figure 31:
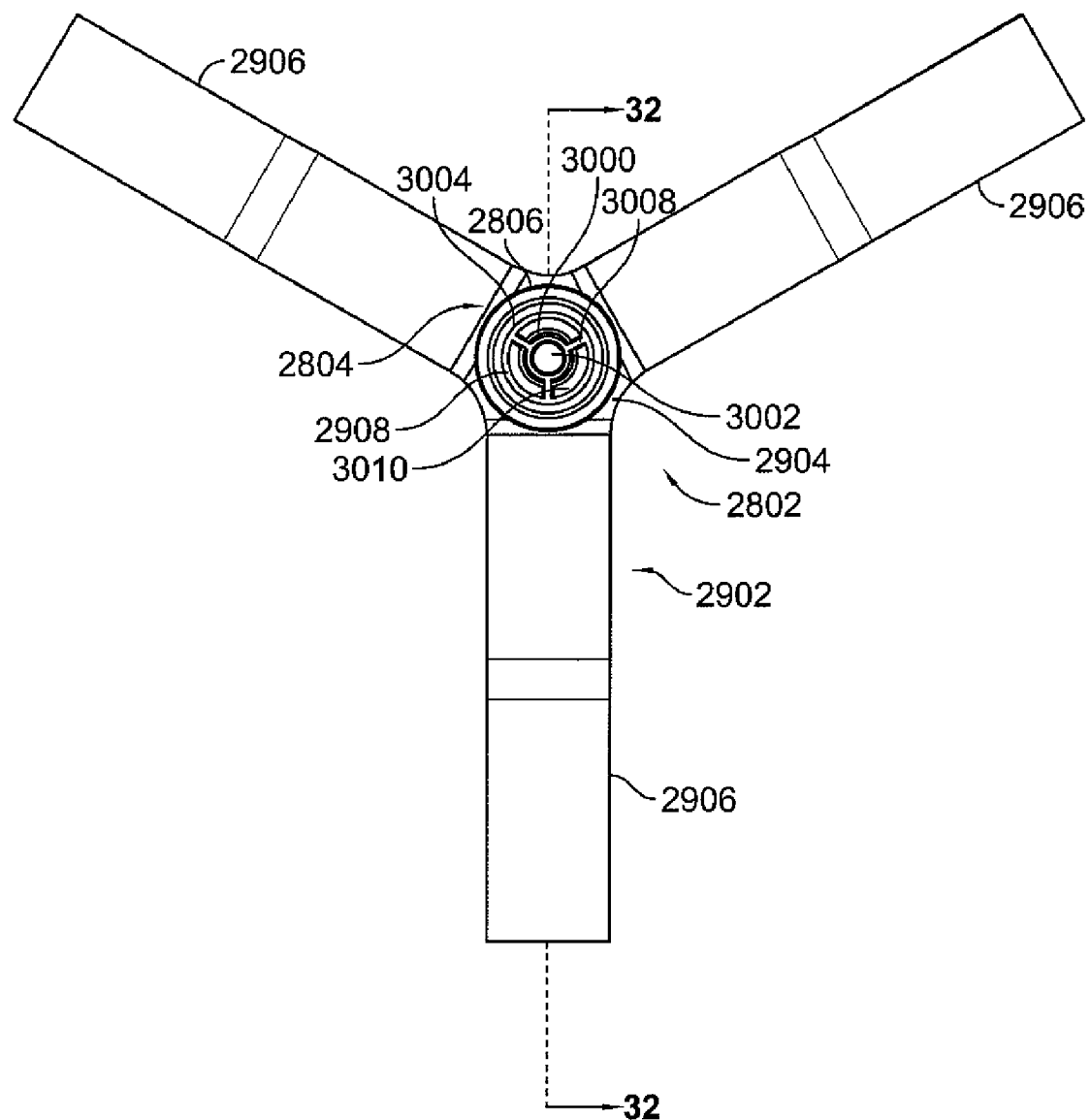
FIG. 31 is an end view of a valve prosthesis of the valve prosthesis system of FIG. 28.

As shown in FIGS. 29 and 31, the valve prosthesis 2802 may include a hub 2900 and a resilient element 2902 coupled to the hub 2900. The resilient element 2902 may include a hub flange 2904 at which the resilient element 2902 may be coupled to the hub 2900 and multiple instances of a leg 2906 that may extend radially outward from the hub flange 2904. One or more of the multiple instances of a leg 2906 may be of unitary construction with the hub flange 2904. In FIGS. 29 and 31, the valve prosthesis 2802 is shown after having emerged from an outer catheter (not shown), and after the surgeon/clinician has utilized the tool 2814 (FIG. 25) to pull corresponding deployment cables (not shown) relative to the valve prosthesis 2802 so as to overturn positioning elements (not shown) relative to a flexible ring (not shown), and/or relative to the hub 2900, and/or relative to the hub flange 2904. In addition to including the release tube 2806, the locking sleeve 2810 attached to the proximal end 2808 of the release tube 2806, and the cable deployment tower 2812 extending through and beyond the hub 2900 and the resilient element 2902 of the valve prosthesis 2802 as discussed above with reference to FIGS. 28 and 34, the delivery structure 2804 includes a cable guide tube 2908 disposed within the release tube 2806. As shown in FIGS. 30 and 31, the cable guide tube 2908 includes an interior wall 3000 defining a central lumen 3002, an exterior wall 3004 defining an outer surface 3006 and, with a series of radially-extending interior walls 3008, defining multiple instances of a peripheral lumen 3010 arranged in a regular pattern around the central lumen 3002.

Figure 32:
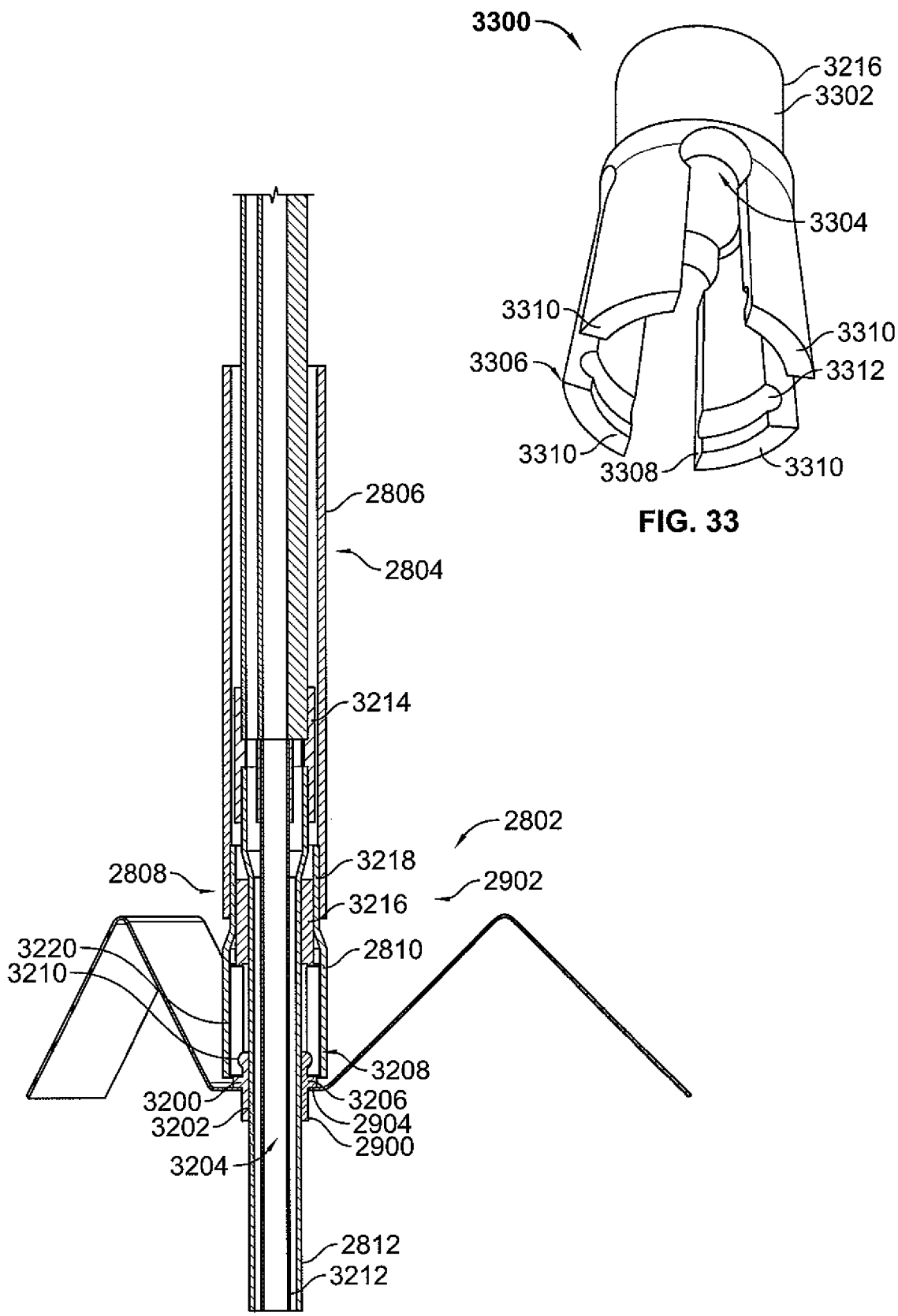
FIG. 32 is a sectional side view of a valve prosthesis of the valve prosthesis system of FIG. 28 taken along section line 32-32 appearing in FIG. 31.

Referring now to FIG. 32, the hub 2900 of the valve prosthesis 2802 includes a body 3200 including a wall 3202. The wall 3202 is cylindrical in shape so as to define a central lumen 3204 passing through the body 3200, the central lumen 3204 being sized and shaped so as to receive and accommodate the cable deployment tower 2812. Each of the hub 2900 and the cable deployment tower 2812 may be fabricated from stainless steel, and the inner diameter of the central lumen 3204 of the hub 2900 and the outer diameter of the cable deployment tower 2812 may be controlled relative to each other such that a relatively precise lateral fit exists between the two parts while also permitting relatively free movement of the cable deployment tower 2812 in the axial direction relative to the hub 2900 for purposes of pulling the cable deployment tower 2812 free of the valve prosthesis 2802 upon the latter being implanted within a patient's diseased heart valve (not shown) (e.g., wherein the only available reaction force is that which is provided by the cardiac tissue with which the valve prosthesis 2802 is engaged).

The wall 3202 of the hub 2900 extends axially to define the central lumen 3204. At an intermediate position along an axial extent of the hub 2900, an annular ledge 3206 extends outward from the wall 3202. The hub flange 2904 of the resilient element 2902 attaches to the hub 2900 at the circumferential skirt 3206. At an upper end of the axial extent of the hub 2900, the body 3200 further includes a coupling interface 3208. The coupling interface 3208 includes an annular protrusion 3210 extending outward from the wall 3202, which as shown in FIG. 32, may be have a rounded profile.

Figure 33:
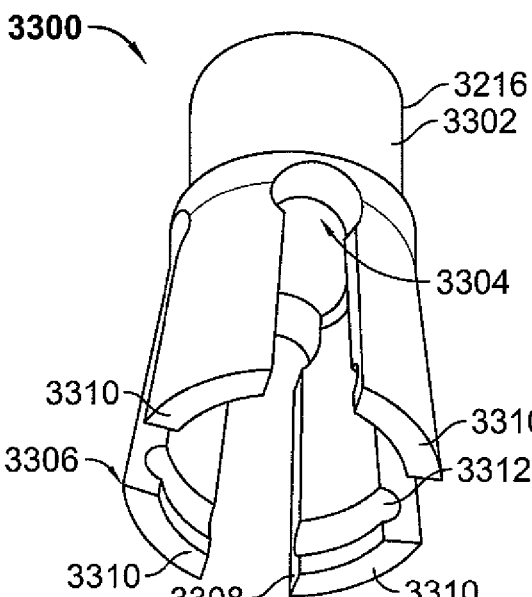
FIG. 33 is a perspective view of a resilient element in the valve prosthesis illustrated in FIG. 32.

Still referring to FIG. 32, the delivery structure 2804 further includes a guide wire sleeve 3212, a fitting 3214, and a resilient element 3216. The guide wire sleeve 3212 is disposed within the cable deployment tower 2812. The fitting 3214 joins, within the release tube 2806, the cable guide tube 2908 (on one side of the fitting 3214) with the cable deployment tower 2812 and the guide wire sleeve 3212 (on an opposite side of the fitting 3214). Referring now to FIG. 33, the resilient element 3216 includes a distal end 3300 that includes a collar 3302 that at least partially defines a central lumen 3304 through the resilient element 3216, and a proximal end 3306 featuring a coupling interface 3308. The coupling interface 3308 is peripherally segmented and includes multiple instances of an outwardly biased and inwardly deflectable spring finger 3310. Each such spring finger 3310 includes a depression 3312 having a segmented annular shape and sectional profile to match that of the annular protrusion 3210 (FIG. 32) of the coupling interface 3208 of the hub 2900.

Referring again to FIG. 32, the resilient element 3216 may be affixed to the cable deployment tower 2812 such that the latter is lodged within the central lumen 3304 of the former. The locking sleeve 2810 includes an axially narrowed distal end 3218 near which the locking sleeve 2810 is lodged within the proximal end 2808 of the release tube 2806, and an axially expanded proximal end 3220 extending toward the valve prosthesis 2802. The proximal end 3220 of the locking sleeve 2810 is of a large enough interior diameter to surround and extend over the proximal end 3306 (FIG. 33) of the resilient element 3216. The relative dimensions of the resilient element 3216 and the locking sleeve 2810 are such that the locking sleeve 2810 is capable of deflecting the spring fingers 3310 (FIG. 33) of the resilient element 3216 inward. If at this time the coupling interface 3308 (FIG. 33) of the resilient element 3216 and the coupling interface 3208 of the hub 2900 overlap each other (e.g., axially), the hub 2900 and the resilient element 3216 will become axially coupled, and may be moved axially within an outside catheter (not shown) together as a unit. Additionally, upon the valve prosthesis 2802 being properly positioned and oriented with respect to a patient's diseased heart valve, such an arrangement enables a surgeon/clinician to release the valve prosthesis 2802 by causing the release tube 2806 to retract away from the valve prosthesis 2802 and the resilient element 3216 such that the spring fingers 3310 deflect radially outward and lose their grip on the annular protrusion 3210 of the hub 2900. At this time, and as described in greater detail above, the cable deployment tower 2812 can be smoothly withdrawn from within the hub 2900, and the delivery structure 2804 completely withdrawn from the patient via the external catheter (not shown).

Figure 35:
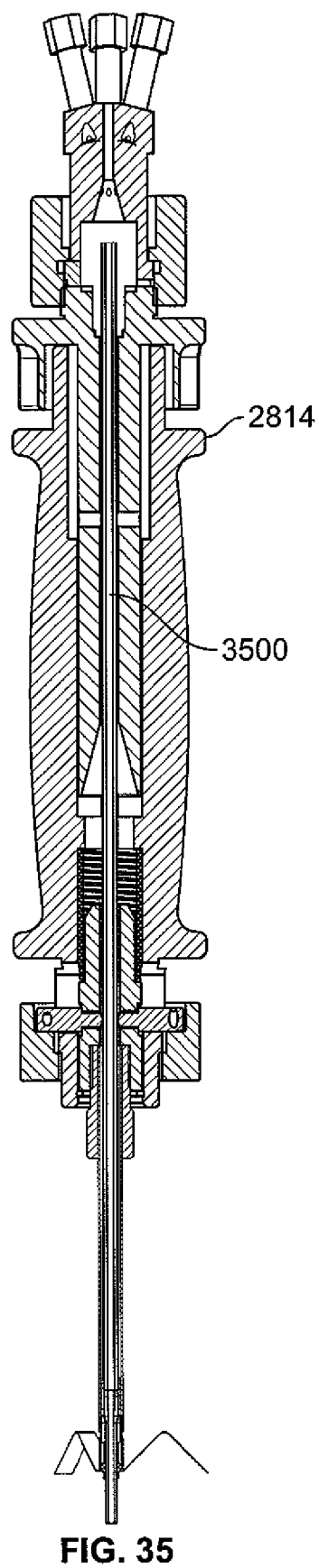
FIG. 35 is a sectional side view of a tool of the valve prosthesis system of FIG. 28 taken along section line 35-35 appearing in FIG. 34.

Turning now to FIG. 35, the tool 2814 includes a central lumen 3500 extending through an entire axial length of the tool 2814. The central lumen 3500 is adapted to accommodate, at least, a guide wire (not shown).

Figure 36:
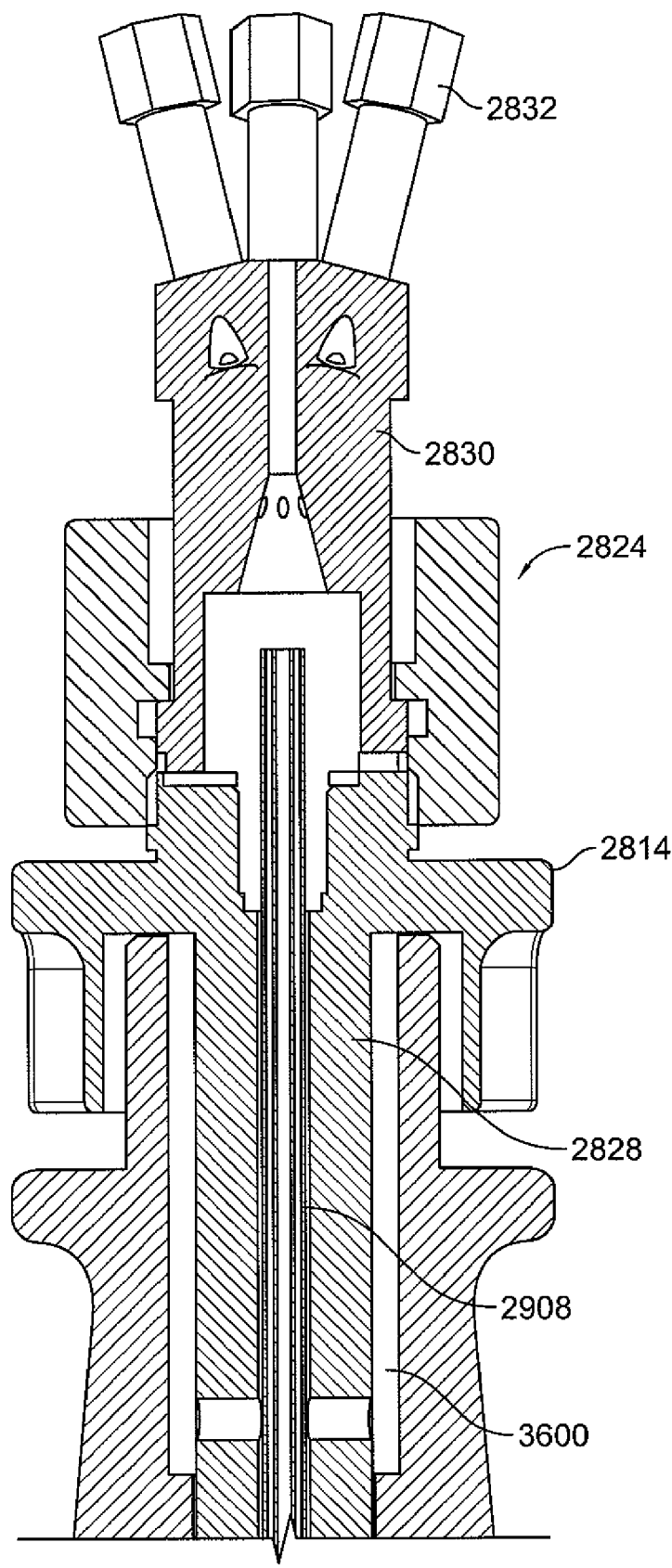
FIG. 36 is a sectional side view of part of the tool of the valve prosthesis system of FIG. 28 taken along section line 35-35 appearing in FIG. 35.

Referring now to FIG. 36, the body 2816 of the tool 2814 includes a central cavity 3600, and the actuation arm 2828 of the prosthesis deployment mechanism 2824 is disposed within and moves relative to the central cavity 3600. Cables (not shown) passing through the actuation arm 2828 may pass into the cable mount 2830 and extend into one or more passages in communication therewith and terminating in an attachment fitting 2832, at which the cable (not shown) may be axially secured to the cable mount 2830, and by extension, to the actuation arm 2828. In the specific example of FIG. 28, up to six separate cables may be so accommodated and axially coupled to the cable mount 2830. Other numbers of cables accommodated by a cable mount with more or fewer attachment fittings are possible.

In some embodiments of the present disclosure, the cable guide tube 2908 may extend through the tool 2814, e.g., at least to an extent of the prosthesis deployment mechanism 2824. In at least some circumstances in accordance with embodiments of the present disclosure, a surgeon/clinician may not necessarily require the cable guide tube 2908 to be or remain axially fixed with respect to the tool 2814. In such circumstances, the tool 2814 may include no particular securing mechanism with respect to the cable guide tube 2908, in which case a proximal end of the cable guide tube 2908 may extend into the tool 2814, wherein neither the proximal end nor any other portion of the cable guide tube 2908 will necessarily be lodged in a corresponding fitting, or terminated in any particular way, facilitating axial relative motion between the cable guide tube 2908 and the tool 2814. By contrast, and in at least some circumstances in accordance with the present disclosure, a surgeon/clinician requiring the cable guide tube 2908 to at least temporarily be or remain axially fixed with respect to the tool 2814. In such circumstances, the surgeon/clinician may rely on an overall or locally substantial static or dynamic friction within the delivery structure 2804 (e.g., between the cable guide tube 2908 and other portions of the delivery structure 2804, such as the release tube 2806). Alternatively, and/or in addition, the tool 2814 may further include a clamp or fitting (not shown) or other similar mechanism or securing means to at least temporarily secure (e.g., axially fix) the cable guide tube 2908 with respect to the tool 2814, e.g., with respect to the body 2816 of the tool 2814, and/or to the prosthesis deployment mechanism 2824 thereof. Other configurations are possible.

Referring again to FIG. 28, once the required cables (not shown) are secured to the cable block 2830, and provided the locking sleeve 2810 is in place over the spring fingers 3310 (FIG. 33) of the resilient element 3216 (FIG. 32) and the annular protrusion 3210 of the hub 2900 (FIG. 32), and the valve prosthesis 2802 is free of the outer catheter (not shown) and is positioned adjacent a patient's diseased heart valve, a surgeon/clinician may grasp the gripping handle 2822 with one hand, grasp the actuation arm 2828 with the other hand, and pull the actuation arm 2828 outward of the body 2816 to move the cables outward of the valve prosthesis 2802 to cause the valve prosthesis to assume the proper shape for insertion into the valve (e.g., see, e.g., FIGS. 4F and 20). In some embodiments of the present disclosure, once the valve prosthesis 2802 assumes such proper valve insertion shape, the actuation arm 2828 may be rotated relative to the body 2830 to engage a catch (not separately shown) that preserves the existing axial positions of the actuation arm 2828 and the body 2830 relative to each other, enabling the surgeon/clinician to focus on proper placement of the valve prosthesis 2802 relative to the diseased valve without being concerned that the valve prosthesis 2802 will abruptly revert to a previously held shape or assume any other shape that is not intended.

Figure 37:
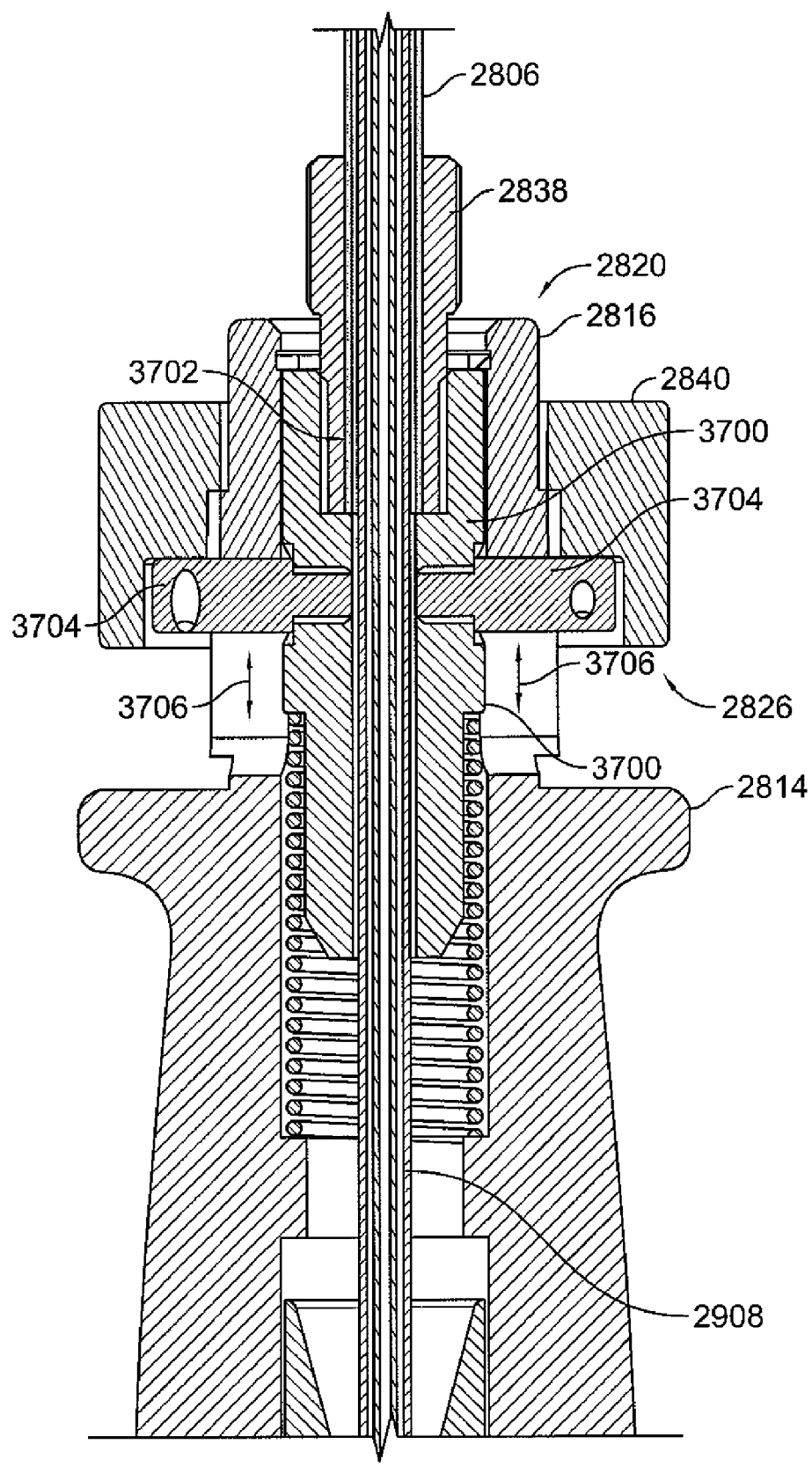
FIG. 37 is a sectional side view of another part of the tool of the valve prosthesis system of FIG. 28 taken along section line 35-35 appearing in FIG. 35.

Referring to FIG. 37, the prosthesis release mechanism 2826 may further include an attachment sleeve 3700 that is spring biased outward of the proximal end 2820 of the tool 2814 but is moveable axially relative to the body 2816. The attachment sleeve 3700 receives the release tube 2806 and the attachment fitting 2838, wherein the attachment fitting 2838 cooperates with the attachment sleeve 3700 to axially secure a distal end 3702 of the release tube 2806 relative to the attachment sleeve 3700. The prosthesis release mechanism 2826 further includes one or more anti-rotation pins 3704 emerging from the attachment sleeve 3700 and interacting with an axially-extending channel 3706 formed in the body 2816 of the tool 2814 so as to prevent rotation of the attachment sleeve 3700 relative to the body 2816 but permit the attachment sleeve 3700 to translate axially relative thereto. The actuation wheel 2840 may be coupled to the body 2816 of the tool 2814 via screw threads and may be adapted to contact the pins 3704 and urge the pins 3704 axially inward relative to the body 2816. This may cause the release tube 2806 to retract away from the valve prosthesis 2802, such that the resilient element 3216 (FIG. 32) is uncovered by the locking sleeve 2810, the spring fingers 3310 separate from the hub 2900, and the delivery structure 2804 is no longer capable of axially urging the valve prosthesis 2802. As described above, in such circumstances, the delivery structure 2804 may be withdrawn from the patient, leaving the valve prosthesis 2802 in place relative to the diseased heart valve.

Although implementations of the invention have been described in detail above, those skilled in the art will readily appreciate that many additional modifications are possible without materially departing from the novel teachings and advantages of the invention. Any such modifications are intended to be included within the scope of the invention as defined in the following claims.

The invention claimed is:

1. A valve prosthesis, comprising:
   a. a resilient ring defining an annular opening;
   b. a plurality of leaflet membranes mounted with respect to the resilient ring; and
   c. a plurality of positioning elements movably mounted with respect to the resilient ring, each of the positioning elements defining a first tissue engaging region, a connecting region, and a second tissue engaging region spaced from the first tissue engaging region, wherein the connecting region connects the first and second tissue engaging regions;
   wherein each positioning element of the plurality of positioning elements is inverted by rotating relative to the resilient ring between a first position in which each of the first and second tissue engaging regions is inwardly directed towards the annular opening for facilitating positioning of the valve prosthesis within a delivery catheter, and a second position in which each of the first and second tissue engaging regions is outwardly directed towards an anatomical wall for engaging tissue; and
   wherein each positioning element of the plurality of positioning elements is inverted by rotating in a first direction away from the first position and toward and into the second position to define an inversion plane.

2. The valve prosthesis according to claim 1, wherein each of the first and second tissue engaging regions defines a tissue engaging arc.

3. The valve prosthesis according to claim 1, wherein each of the first and second tissue engaging regions defines a plurality of tissue engaging spikes.

4. The valve prosthesis according to claim 1, wherein each of the first and second tissue engaging regions defines a plurality of tissue engaging teeth.

5. The valve prosthesis according to claim 1, wherein the positioning elements are resilient and are adapted to resiliently deflect to engage tissue disposed between the first and second tissue engaging regions.

6. The valve prosthesis according to claim 5, wherein each of the positioning elements defines a V shape, and the first and second tissue engaging regions form respective opposing flexible arms of the V shape for engaging a tissue disposed between the opposing flexible arms.

7. The valve prosthesis according to claim 5, wherein each of the positioning elements defines a set of spaced jaws adapted to move with respect to each other, and the first and second tissue engaging regions are defined by respective opposing jaw portions directed toward each other for engaging tissue disposed therebetween.

8. The valve prosthesis according to claim 1, wherein at least one of the first and second tissue engaging regions defines a resilient coil, wherein the resilient coil is adapted to be uncoiled as against a coiling bias to permit an outwardly directed end of the uncoiled coil to engage tissue.

9. The valve prosthesis according to claim 1, wherein each of the positioning elements includes a third tissue engaging region disposed between the first and second tissue engaging region thereof that is outwardly facing in the second position.

10. The valve prosthesis according to claim 9, wherein the third tissue engaging region defines a plurality of tissue engaging holes.

11. The valve prosthesis according to claim 9, wherein the third tissue engaging region defines a plurality of tissue engaging spikes.

12. The valve prosthesis according to claim 9, wherein the third tissue engaging region defines a plurality of tissue engaging holes and a plurality of tissue engaging spikes.

13. The valve prosthesis according to claim 1, wherein the resilient ring includes multiple instances of a hoop segment defining a hoop plane and separated by a corresponding number of instances of a gap within the hoop plane.

14. The valve prosthesis according to claim 1, wherein the resilient ring includes multiple instances of a hoop segment defining a hoop plane and a corresponding number of instances of a coupling segment extending vertically relative to the hoop plane.

15. The valve prosthesis according to claim 1, wherein the resilient ring includes multiple instances of a hoop segment defining a hoop plane and a corresponding number of instances of a coupling segment, wherein each coupling segment includes a spring having two leaves joined at a bend region for imparting an elastic force on the hoop segments.

16. The valve prosthesis according to claim 1, wherein the resilient ring includes a plurality of suture-accommodating notches for use in securing a corresponding leaflet membrane of the plurality of leaflet membranes with respect thereto.

17. The valve prosthesis according to claim 1, wherein the resilient ring defines a circular or elliptical peripheral geometry.

18. The valve prosthesis according to claim 1, wherein each positioning element of the plurality thereof is biased in favor of rotating away from the first position and toward the second position.

19. The valve prosthesis according to claim 1, wherein each positioning element of the plurality thereof is further adapted to be rotated further within the inversion plane in the first direction from the second position to a third position in which a distal one of the first and second tissue engaging elements is directed substantially downward for dilating obstructing tissue during a process of advancing the valve prosthesis downward into an anatomical annulus for implantation with respect thereto.

20. The valve prosthesis according to claim 19, wherein each positioning element of the plurality thereof is biased in favor of rotating away from the third position and toward the second position within the inversion plane when the positioning element is in the third position.

21. The valve prosthesis according to claim 19, further comprising a hub disposed substantially centrally with respect to a peripheral geometry of the resilient ring and a plurality of legs directed radially with respect to the resilient ring and mounted with respect to (i) the hub and (ii) a corresponding positioning element of the plurality thereof, wherein each leg includes an intermediate joint and corresponding leg lengths extending from the joint for forming a spring to bias the positioning element away from the third position and back toward the second position when the positioning element is in the second position.

22. The valve prosthesis according to claim 21, further comprising a joint between the hub and each leg for forming an additional spring to bias the positioning element away from the third position and back toward the second position when the positioning element is in the second position.

23. The valve prosthesis according to claim 1, wherein each positioning element of the plurality thereof includes a pair of apertures for permitting the positioning element to be releasably engaged by a corresponding filament looped through the apertures of the pair thereof for urging the positioning element to rotate within a plane defined by the inversion.

24. The valve prosthesis according to claim 1, wherein the plurality of leaflet membranes are fabricated from a xenographic material.

25. The valve prosthesis according to claim 1, wherein the resilient ring is adapted to be implanted with respect to an anatomical annulus such that the first tissue engaging region engages tissue associated with a proximal portion of the anatomical annulus, and the second tissue engaging portion engages tissue associated with a distal portion of the anatomical annulus.

26. The valve prosthesis according to claim 1, further comprising a valve skirt mounted with respect to the resilient ring.

27. The valve prosthesis according to claim 26, wherein the valve skirt extends to an elevation below that of the resilient ring.

28. The valve prosthesis according to claim 27, wherein the valve skirt further extends to an elevation above that of the resilient ring.

29. The valve prosthesis according to claim 26, wherein the valve skirt defines a variable thickness.

30. The valve prosthesis according to claim 26, wherein the valve skirt defines a tapered thickness.

31. A valve prosthesis, comprising:
   a. a resilient ring defining an annular opening;
   b. a plurality of leaflet membranes mounted with respect to the resilient ring; and
   c. a plurality of positioning elements movably mounted with respect to the resilient ring, each of the positioning elements defining a first tissue engaging region, a connecting region, and a second tissue engaging region spaced from the first tissue engaging region, wherein the connecting region connects the first and second tissue engaging regions;
   wherein each positioning element of the plurality of positioning elements is inverted by rotating relative to the resilient ring between a first position in which each of the first and second tissue engaging regions is inwardly directed towards the annular opening for facilitating positioning of the valve prosthesis within a delivery catheter, and a second position in which each of the first and second tissue engaging regions is outwardly directed towards an anatomical wall for engaging tissue; and
   wherein each positioning element of the plurality thereof is inverted at least in part by rotating outward and away from the first position, and toward and into the second position, in an overturning motion with respect to the resilient ring.

32. The valve prosthesis according to claim 31, further comprising a hub disposed substantially centrally with respect to a peripheral geometry of the resilient ring, and a plurality of legs directed radially with respect to the resilient ring and mounted with respect to (i) the hub and (ii) a corresponding positioning element of the plurality thereof.

33. The valve prosthesis according to claim 32, wherein the leg is mounted with respect to the positioning element such that the positioning element is substantially rotationally fixed with respect to the leg.

34. The valve prosthesis according to claim 32, wherein the leg includes an intermediate joint and corresponding leg lengths extending from the joint for allowing the leg to collapse against itself to facilitate the positioning element assuming the first position.

35. The valve prosthesis according to claim 32, wherein the leg includes an intermediate joint and corresponding leg lengths extending from the joint for forming a spring to bias the positioning element outward and away from the first position and toward the second position when the positioning element is in the first position.

36. The valve prosthesis according to claim 35, wherein the hub is disposed at an elevation below that of the resilient ring when the positioning element is in the first position and, upon the positioning element rotating away from the first position and into the second position, the hub shifts upward to an elevation even with or above that of the resilient ring.

37. The valve prosthesis according to claim 32, wherein the leg includes an intermediate joint and corresponding leg lengths extending from the joint for forming a spring to bias the positioning element away from the second position and back toward the first position when the positioning element is in the second position.

38. The valve prosthesis according to claim 37, further comprising a joint between the hub and the leg for forming a second spring to bias the positioning element away from the second position and back toward the first position when the positioning element is in the second position.

39. The valve prosthesis according to claim 32, wherein the leg includes an intermediate joint and corresponding leg lengths extending from the joint for forming a spring to bias the positioning element either outward and away from the first position and toward the second position, or away from the second position and back toward the first position, depending on whether the positioning element is in the first position or the second position, respectively.

40. A valve prosthesis, comprising:
   a. a resilient ring defining an annular opening;
   b. a plurality of leaflet membranes mounted with respect to the resilient ring; and
   c. a plurality of positioning elements movably mounted with respect to the resilient ring, each of the positioning elements defining a first tissue engaging region, a connecting region, and a second tissue engaging region spaced from the first tissue engaging region, wherein the connecting region connects the first and second tissue engaging regions;
   wherein each positioning element of the plurality of positioning elements is inverted by rotating relative to the resilient ring between a first position in which each of the first and second tissue engaging regions is inwardly directed towards the annular opening for facilitating positioning of the valve prosthesis within a delivery catheter, and a second position in which each of the first and second tissue engaging regions is outwardly directed towards an anatomical wall for engaging tissue; and
   wherein at least the resilient ring and each positioning element of the plurality thereof are adapted to be collapsed to an extent sufficient to permit the same to be lodged together in a catheter lumen of 26 French or less.

* * * * *